United States Patent [19]

Hatfield

[11] 4,144,391

[45] Mar. 13, 1979

[54] CEPHALOSPORIN DISPLACEMENT REACTION

[75] Inventor: Lowell D. Hatfield, Bargersville, Ind.

[73] Assignee: Eli Lilly and Company, Indianapolis, Ind.

[21] Appl. No.: 862,871

[22] Filed: Dec. 27, 1977

Related U.S. Application Data

[63] Continuation-in-part of Ser. No. 775,018, Mar. 7, 1977, abandoned.

[51] Int. Cl.$^2$ ............................................ C07D 501/36
[52] U.S. Cl. ........................................ 544/21; 544/27; 544/29; 544/30
[58] Field of Search ........................ 544/29, 30, 27, 21

[56] References Cited

U.S. PATENT DOCUMENTS

| | | | |
|---|---|---|---|
| 3,278,531 | 10/1966 | Cox et al. | 260/243 C |
| 3,641,021 | 2/1972 | Ryan | 260/243 C |
| 3,658,799 | 4/1972 | Fardley et al. | 260/243 C |
| 3,668,203 | 6/1972 | Clark et al. | 260/243 C |
| 3,776,907 | 12/1973 | Essery et al. | 260/243 C |

OTHER PUBLICATIONS

Cocker et al., J. Chem. Soc., pp. 5015–5031 (1966).
Taylor, J. Chem. Soc., pp. 7020–7029 (1965).

*Primary Examiner*—Nicholas S. Rizzo
*Attorney, Agent, or Firm*—Steven R. Lammert; Kathleen R. S. Page; Arthur R. Whale

[57] ABSTRACT

The present invention is directed to a process for the displacement of the acetoxy group of a cephalosporanic acid by a sulfur nucleophile, in an organic solvent and under essentially anhydrous conditions.

115 Claims, No Drawings

CEPHALOSPORIN DISPLACEMENT REACTION

CROSS-REFERENCE TO RELATED APPLICATION

This application is a continuation-in-part of U.S. application Ser. No. 775,018, filed Mar. 7, 1977, now abandoned.

BACKGROUND OF THE INVENTION

The displacement of the acetoxy group of a cephalosporin by a sulfur nucleophile is a known reaction (U.S. Pat. No. 3,278,531). This patent and other publications (J. D. Cocker, J. Chem. Soc., 1965, 5015) teach that the reaction occurs only in an aqueous medium. Practical displacements have utilized a salt of the cephalosporanic acid in water along with the sulfur nucleophile or its salt at pH 5-8. The combination of aqueous medium, elevated temperature (35°-70° C.), and near neutral to basic pH are generally destructive of much of the cephalosporin nucleus, and products prepared in this manner often require extensive purification. Attempts to conduct the displacement on cephalosporanic acids in water at lower pH (pH 2-3) lead to substantial lactone formation, a side-reaction that dramatically lowers the yield of desired product.

SUMMARY

It has now been discovered that the displacement of the acetoxy group (as well as other 3-acyloxy groups) of cephalosporanic acids by sulfur nucleophiles can be achieved in organic solvents under essentially anhydrous conditions. Reactions under these conditions are not complicated by lactone formation; yields are generally higher; and products are more easily isolated. Some of the products spontaneously precipitate from the reaction mixture. The present process is believed to be general in nature, and applicable to essentially any sulfur nucleophile and any cephalosporanic acid.

However, more particularly, the present invention is a process for the displacement of the 3-acyloxy of a 3-(acyloxymethyl)cephalosporin by a sulfur nucleophile, which comprises reacting, in an organic solvent and under essentially anhydrous conditions, a 3-(acyloxymethyl)cephalosporin compound of the formula

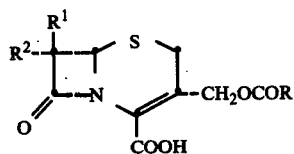

with a sulfur nucleophile of the formula:

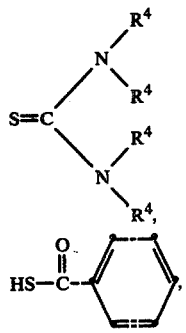
(1)

(2)

$HS\text{—}C_1\text{—}C_4$ alkyl, (3)

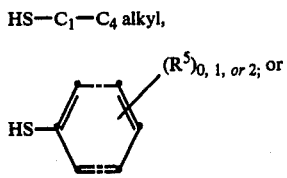 (4)

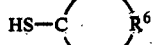 (5)

and obtaining a reaction product of the formula

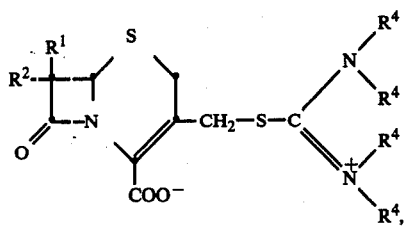

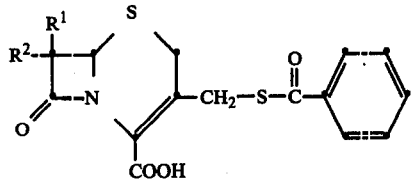

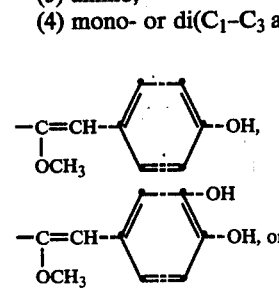, respectively

In the above and succeeding formulae throughout the present specification and claims, R through $R^6$ have the following meanings: R is
(1) $C_1$–$C_3$ alkyl,
(2) $C_4$–$C_6$ cycloalkyl,
(3) amino,
(4) mono- or di($C_1$–$C_3$ alkyl) amino,

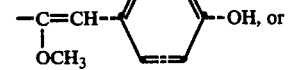 (5)

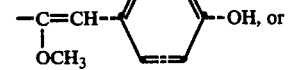 (6)

-continued

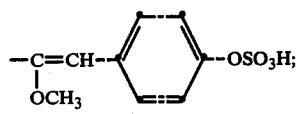 (7)

R¹ is hydrogen or methoxy;

R² is phthalimido, succinimido, a radical of the formula

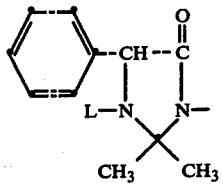

wherein L is hydrogen or nitroso, or a radical of the formula

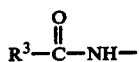

wherein R³ is
(1) hydrogen,
(2) $C_1$-$C_6$ alkyl,
(3) —$CH_2$—($C_1$-$C_3$ chloroalkyl),
(4) —$CH_2$—($C_1$-$C_3$ fluoroalkyl),
(5) $C_1$-$C_4$ cyanoalkyl,
(6) $C_1$-$C_4$ hydroxyalkyl,
(7) p-nitrobenzyloxy,
(8) tert-butoxy,
(9) (2,2,2-trichloroethoxy),
(10) a protected 4-amino-4-carboxybutyl radical of the formula

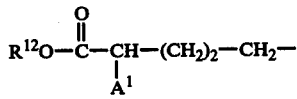

wherein A¹ is a protected amino group and R¹² is hydrogen or $C_1$-$C_4$ alkyl;
(11) 4-oxo-4-carboxybutyl;
(12) 3-carboxypropyl;
(13) a radical of the formula

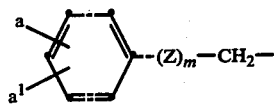

in which each of a and a¹ is independently hydrogen, $C_1$-$C_4$ alkyl, $C_1$-$C_4$ alkoxy, halogen, hydroxy, or A¹C$H_2$— wherein A¹ is, as above, protected amino; Z is 0 or S; and m is 0 or 1;
(14) a radical of the formula

wherein P is
(a) 2-thienyl,
(b) 3-thienyl, or (c) a phenyl group of the formula

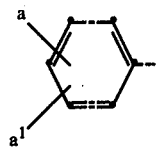

in which a and a¹ are as defined above; and wherein Q is
(a) hydroxy,
(b) formyloxy,
(c) acetoxy,
(d) carboxy of the formula

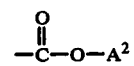

wherein A² is diphenylmethyl, p-nitrobenzyl, benzyl, 2,2,2-trichloroethyl, tert-butyl, or p-methoxybenzyl;
(e) (alkali metal oxysulfonyl),
(f) a protected amino group,
(g) an acylated amino group of the formula

wherein T is, for example, amino,

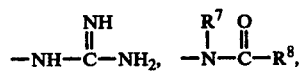

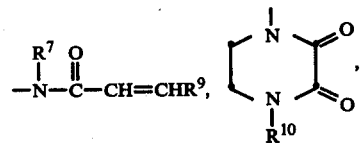

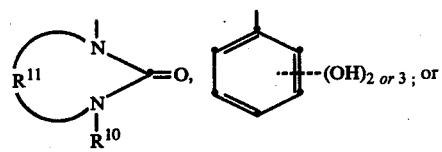

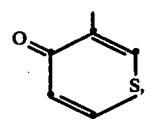

wherein R⁷ is hydrogen or $C_1$-$C_3$ alkyl; R⁸ is phenyl, halophenyl, furyl, monomethylamino, dimethylamino, monoethylamino, diethylamino, methylethylamino, propylamino, dipropylamino, diisopropylamino, phenylamino, or diphenylamino; R⁹ is hydrogen, $C_1$-$C_4$ alkyl, or phenyl; R¹⁰ is hydrogen, $C_1$-$C_3$ alkyl, or methylsulfonyl; and R¹¹ is ethylene, trimethylene, or vinylene;
(15) a radical of the formula

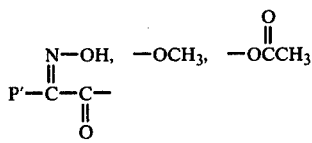

wherein P' is P as defined above, protected 2-amino-4-thiazolyl, or 2-furyl;

(16) a radical of the formula V—S(O)$_n$—CH$_2$— wherein V represents —CF$_3$ or —CH$_2$—X wherein X represents hydrogen, methyl, CF$_3$, CN, or N$_3$, and n represents 0, 1, or 2; or

(17) a radical of the formula Y—CH$_2$— in which Y is
(a) 2-thienyl,
(b) 3-thienyl,
(c) 2-furyl,
(d) 2-oxazolyl,
(e) 2-thiazolyl,
(f) 1-tetrazolyl,
(g) 1-benzotriazolyl,
(h) 2-oxazolylthio,
(i) 2-thiazolylthio,
(j) 1,2,3-triazol-5-ylthio,
(k) 1,3,4-triazol-2-ylthio,
(l) 1,3,4-thiadiazol-2-ylthio,
(m) protected 5-amino-1,3,4-thiadiazol-2-ylthio,
(n) 5-methyl-1,3,4-thiadiazol-2-ylthio,
(o) 1,2,4-thiadiazol-5-ylthio,
(p) 3-methyl-1,2,4-thiadiazol-5-ylthio,
(q) 1,2,5-thiadiazol-3-ylthio,
(r) 1,3,4-oxadiazol-2-ylthio,
(s) 5-methyl-1,3,4-oxadiazol-2-ylthio,
(t) 1-methyl-5-tetrazolylthio,
(u) pyridylthio,
(v) 4-cyano-1,2,3-triazol-1-yl,
(w) 3-cyano-1,2,4-triazol-1-yl, or
(x) protected 2-amino-4-thiazolyl.

each R$^4$ is independently
(1) hydrogen,
(2) C$_1$-C$_3$ alkyl,
(3) C$_2$-C$_3$ alkenyl,
(4) cyclohexyl, or
(5) phenyl;

each R$^5$ is independently C$_1$-C$_4$ alkyl, C$_1$-C$_4$ alkoxy, halo, hydroxy, nitro, cyano, methanesulfonamido, or trifluoromethyl; and R$^6$ is (1) a unit which with the

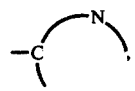

comprises an unsubstituted or substituted, five or six-membered, heteroaromatic ring having a total of from 1 to 4 hetero atoms selected from the following combinations:

1 nitrogen and 0 or 1 oxygen or sulfur,
2 nitrogens and 0 or 1 oxygen or sulfur,
3 nitrogens, and 0 or 1 oxygen, or
4 nitrogens, all other ring atoms being carbon; or (2) a unit which with the

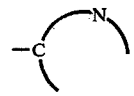

comprises 2-benzimidazolyl, 2-benzothiazolyl, 2-benzoxazolyl, or a radical of the formula

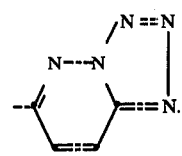

The products of the present process exhibit antibacterial activity; in addition, many of them serve as intermediates to yet other cephalosporin products which also exhibit antibacterial activity, see, e.g. U.S. Pat. No. 3,932,393.

DETAILED DESCRIPTION OF THE INVENTION

Cephalosporin Reactant

As set forth above, the 3-(acyloxymethyl)cephalosporin reactant is of the formula

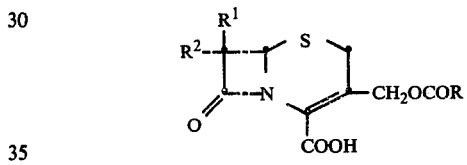

wherein R, R$^1$ and R$^2$ are as defined above.

In the foregoing definitions, the various "alkyl" terms refer to both straight and branched chain alkyl groups. In the definition of R$^3$ as "C$_1$-C$_6$ alkyl," alkyl refers to group such as methyl, ethyl, propyl, isopropyl, butyl, sec-butyl, amyl, isoamyl, hexyl, 2,3-dimethylbutyl, and the like. The terms "—CH$_2$—(C$_1$-C$_3$ chloroalkyl)" and "—CH$_2$—(C$_1$-C$_3$ fluoroalkyl)" refer to such groups as chloroethyl, fluoroethyl, 2-chloroethyl, 2-chloropropyl, 3-fluoropropyl, 4-chlorobutyl, and the like. The term "C$_1$-C$_4$ cyanoalkyl" refers to such groups as cyanomethyl, 2-cyanoethyl, 3-cyanopropyl, 2-cyanopropyl, and the like. The term "C$_1$-C$_4$ hydroxyalkyl" refers to such groups as hydroxymethyl, 2-hydroxyethyl, 3-hydroxypropyl, 2-hydroxypropyl and the like.

In both the 3-(acyloxymethyl)cephalosporin and the sulfur nucleophile, amino groups are desirably protected. The practice of protecting amino groups is well known. See Protective Groups In Organic Chemistry, edited J. T. W. McOmie (Plenum Press, London and New York, 1973). In general, protection of an amino group implies removability of the protection group; but that is not necessary as, for example, in a 7-acylamido radical of the formula

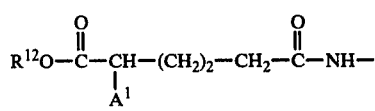

which is subsequently to be cleaved off of the cephalosporin. Suitable protecting groups for this radical include $C_2$-$C_4$ alkanoyl, $C_3$-$C_4$ chloro- or fluoroalkanoyl, benzoyl, and substituted benzoyl. The term "$C_2$-$C_4$ alkanoyl" refers to acetyl, propionyl, butyryl, and the like. The term "$C_3$-$C_4$ chloro- or fluoroalkanoyl" refers to 3-chloropropionyl, 3-fluoropropionyl, and the like. The term "substituted benzoyl" includes halo substituted benzoyl groups such as 4-chlorobenzoyl, 4-bromobenzoyl, and 2,4-dichlorobenzoyl. Such groups can also be employed for the protection of amino groups at other locations in the 3-(acyloxymethyl)cephalosporin, and in the sulfur nucleophile. However, when it is desired to regain a free amino, the protecting group should be one which is readily removable. See McOmie, supra. Suitable protecting groups which are readily removable are benzyloxycarbonyl, p-nitrobenzyloxycarbonyl, 2,2,2-trichloroethoxycarbonyl, tert-butoxycarbonyl, p-methoxybenzyloxycarbonyl, and diphenylmethoxycarbonyl. The amino group of the formula

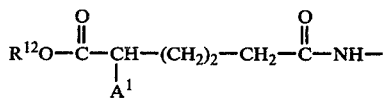

can also be protected as described in Belgian Pat. No. 771,694.

As used herein, the term "halogen" and the term "halo" each refers to fluoro, chloro, bromo, or iodo. The term "$C_1$-$C_4$ alkoxy" refers to methoxy, ethoxy, isopropoxy, n-butoxy, and the like. The term "alkali metal" preferably designates sodium, potassium, and lithium.

The following are illustrative of the group

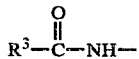

wherein $R^3$ is any of moieties (1) through (12): formamido, acetamido, propionamido, butyramido, α-methylpropionamido, valeramido, α-methylbutyramido, trimethylacetamido, hexanamido, heptanamido, 3-chloropropionamido, 3-chlorobutyramido, 4-fluorobutyramido, 5-chlorovaleramido, cyanoacetamido, 2-cyanopropionamido, 3-cyanopropionamido, 4-cyanobutyramido, hydroxyacetamido, 2-hydroxypropionamido, 3-hydroxybutyramido, p-nitrobenzyloxycarbonylamino, tert-butoxycarbonylamino, (2,2,2-trichloroethoxy)carbonylamino, 5-(2,5-dichlorobenzamido)-5-carboxyvaleramido, 5-acetamido-5-carboxyvaleramido, 5-carbomethoxy-5-(2,4-dichlorobenzamido)valeramido, 5-carbo-n-butoxy-5-(2,4-dichlorobenzamido)valeramido, 5-carboxy-5-(2,4-dichlorobenzamido)valeramido, 5-(p-chlorobenzamido)-5-carboxyvaleramido, 5-propionamido-5-carboxyvaleramido, 5-(3-chloropropionamido)-5-carboxyvaleramido, 5-benzamido-5-carboxyvaleramido, 5-oxo-5-carboxyvaleramido, 4-carboxybutyramido, and the like.

The following are illustrative of the groups

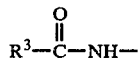

in the above definition in which $R^3$ is

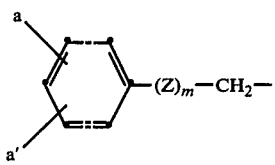

(moiety (13))

and in which m is O: phenylacetamido, 2-(p-methylphenyl)acetamido, 2-(m-ethylphenyl)acetamido, 2-(p-isopropylphenyl)acetamido, 2-(o-methylphenyl)acetamido, 2-(p-chlorophenyl)acetamido, 2-(p-bromophenyl)acetamido, 2-(2,4-dichlorophenyl)acetamido, 2-(m-bromophenyl)acetamido, 2-(p-fluorophenyl)acetamido, 2-(o-fluorophenyl)acetamido, 2-(3,4-dihydroxyphenyl)acetamido, 2-(p-hydroxyphenyl)acetamido, 2-(m-hydroxyphenyl)acetamido, 2-(2,6-dimethoxyphenyl)acetamido, 2-(m-methoxyphenyl)acetamido, 2-(p-isopropoxyphenyl)acetamido, 2-(m-ethoxyphenyl)acetamido, 2-(p-methoxyphenyl)acetamido, 2-(3,4-dimethoxyphenyl)acetamido, 2-(p-tert-butoxyphenyl)acetamido, 2-(p-(acetamidomethyl)phenyl)acetamido, 2-(p-(tert-butoxycarbonylaminomethyl)phenyl)acetamido, 2-(o-(tert-butoxycarbonylaminomethyl)phenyl)acetamido, 2-(m-butoxyphenyl)acetamido, 2-(3-chloro-4-methylphenyl)acetamido and the like. When, in the above formula, m = 1 and Z represents —O—, illustrative groups include the following: phenoxyacetamido, 2-(p-methylphenoxy)acetamido, 2-(m-ethylphenoxy)acetamido, 2-(p-isopropylphenoxy)acetamido, 2-(o-methylphenoxy)acetamido, 2-(p-chlorophenoxy)acetamido, 2-(p-bromophenoxy)acetamido, 2-(2,4-dichlorophenoxy)acetamido, 2-(m-bromophenoxy)acetamido, 2-(p-fluorophenoxy)acetamido, 2-(o-fluorophenoxy)acetamido, 2-(2,6-dimethoxyphenoxy)acetamido, 2-(m-ethoxyphenoxy)acetamido, 2-(p-methoxyphenoxy)acetamido, 2-(3,4-dimethoxyphenoxy)acetamido, 2-(p-tert-butoxyphenoxy)acetamido, 2-(o-butoxyphenoxy)acetamido, 2-(3-chloro-4-methylphenoxy)acetamido, 2-(3-hydroxy-4-methylphenoxy)acetamido, 2-(o-chlorophenoxy)acetamido, 2-(3-hydroxy-4-methylphenoxy)acetamido, 2-(o-chlorophenoxy)acetamido, 2-(p-isopropoxyphenoxy)acetamido, 2-(o-acetamidomethyl)phenoxy)acetamido, 2-(p-(tert-butoxycarbonylaminomethyl)phenoxy)acetamido, and the like. When in the foregoing formula, m = 1 and Z represents —S—, illustrative groups include the following: 2-(phenylthio)acetamido, 2-(p-methylphenylthio)acetamido, 2-(m-ethylphenylthio)acetamido, 2-(p-isopropylphenylthio)acetamido, 2-(o-methylphenylthio)acetamido, 2-(p-chlorophenylthio)acetamido, 2-(p-bromophenylthio)acetamido, 2-(2,4-dichlorophenylthio)acetamido, 2-(m-bromophenylthio)acetamido, 2-(p-fluorophenylthio)acetamido, 2-(o-fluorophenylthio)acetamido, 2-(3,4-dihydroxyphenylthio)acetamido, 2-(p-hydroxyphenylthio)acetamido, 2-(m-hydroxyphenylthio)acetamido, 2-(2,6-dimethoxyphenylthio)acetamido, 2-(m-ethoxyphenylthio)acetamido, 2-(p-methoxyphenylthio)acetamido, 2-(3,4-dimethylphenylthio)acetamido, 2-(p-tert-butoxyphenylthio)acetamido, 2-(m-butoxyphenylthio)acetamido, 2-(3-chloro-4-methylphenylthio)acetamido, 2-(3,4-dimethylphenylthio)acetamido, 2-(3,4-dichlorophenylthio)acetamido, 2-(2,5-dichlorophenylthio)acetamido, 2-(3-fluoro-4-chlorophenylthio)acetamido, 2-(3-chloro-4-fluorophenylthio)acetamido, 2-(2,6-difluorophenylthio)acetamido, 2-(m-fluorophenylthio)acetamido, 2-(o-(acetamidomethyl)phenylthio)acetamido, 2-(p-(tert-butoxycarbonylaminomethyl)phenylthio)acetamido, and such like groups.

When $R^3$ represents a group of the formula

(moiety (14)) illustrative groups having the overall formula

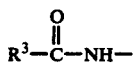

include the mandelamido group of the formula

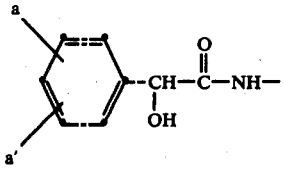

the O-formyl and O-acetyl derivatives thereof represented by the general formula

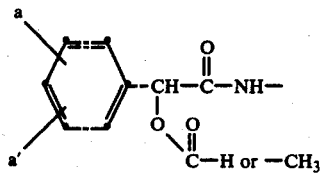

the 2-carboxy-2-phenylacetamido group represented by the formula

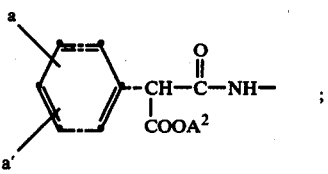

the 2-sulfo-2-phenylacetamido group represented by the formula

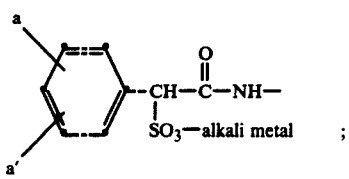

the protected 2-amino-2-phenylacetamido group represented by the formula

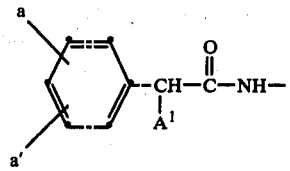

in which $A^1$ is a protected amino group such as benzyloxycarbonylamino, tert-butyloxycarbonylamino, trichloroethoxycarbonylamino, or p-nitrobenzyloxycarbonylamino; and the 2-(acylated amino)-2-phenylacetamido group represented by the formula

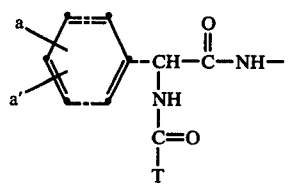

Also included are those 2-substituted 2-thienylacetamido and 3-thienylacetamido groups in which, in the above formulae, the phenyl group is replaced by a 2-thienyl or a 3-thienyl ring.

Illustrative of the foregoing acetamido groups are mandelamido, p-methylmandelamido, p-hydroxymandelamido, m-hydroxymandelamido, p-methoxymandelamido, m-bromomandelamido, p-chloromandelamido, 3-methyl-4-fluoromandelamido, o-fluoromandelamido, p-fluoromandelamido, p-isopropylmandelamido, 3,4-dimethyl-O-formylmandelamido, p-chloro-O-formylmandelamido, m-isopropoxy-O-formylmandelamido, m-bromo-O-formylmandelamido, O-formylmandelamido, 3,4-dimethoxy-O-formylmandelamido, O-acetylmandelamido, p-hydroxy-O-acetylmandelamido, p-(acetamidomethyl)mandelamido, p-hydroxy-O-formylmandelamido, 2-hydroxy-2-(2-thienyl)acetamido, 2-hydroxy-2-(3-thienyl)acetamido, 2-formyloxy-2-(2-thienyl)acetamido, 2-acetoxy-2-(2-thienyl)acetamido, 2-formyloxy-2-(3-thienyl)acetamido, 2-acetoxy-2-(3-thienyl)acetamido, 2-(tertbutoxycarbonyl)-2-phenylacetamido, 2-(2,2,2-trichloroethoxycarbonyl)-2-(p-methylphenyl)acetamido, 2-(benzyloxycarbonyl)-2-(p-hydroxyphenyl)acetamido, 2-(tert-butoxycarbonyl)-2-(p-hydroxyphenyl)acetamido, 2-(p-nitrobenzyloxycarbonyl)-2-(m-hydroxyphenyl)acetamido, 2-(p-metoxybenzyloxycarbonyl)-2-(p-methoxyphenyl)acetamido, 2-(diphenylmethoxycarbonyl)-2-(m-bromophenyl)acetamido, 2-(tert-butoxycarbonyl)-2-(p-chlorophenyl)acetamido, 2-(2,2,2-trichloroethoxycarbonyl)-2-(3-methyl-4-fluorophenyl)acetamido, 2-(benzyloxycarbonyl)-2-(o-fluorophenyl)acetamido, 2-(p-nitrobenzyloxycarbonyl)-2-(p-fluorophenyl)acetamido, 2-(p-metoxybenzyloxycarbonyl)-2-(p-isopropylphenyl)acetamido, 2-(tert-butoxycarbonyl)-2-(3,4-dimethylphenyl)acetamido, 2-(tert-butoxycarbonyl)-2-(m-isopropoxyphenyl)acetamido, 2-(diphenylmethoxycarbonyl)-2-(3,4-dimethoxyphenyl)acetamido, 2-(tert-butoxycarbonyl)-2-(p-(2,5-dichlorobenzamidomethyl)phenyl)acetamido, 2-(tert-butoxycarbonyl)-2-(2-thienyl)acetamido, 2-(tert-butoxycarbonyl)-2-(3-thienyl)acetamido, 2-(sodiooxysulfonyl)-2-phenylacetamido, 2-(sodiooxysulfonyl)2-(p-methylphenyl)acetamido, 2-(potassiooxysulfonyl)-2-(p-hydroxyphenyl)acetamido, 2-(lithiooxysulfonyl)-2-(m- hydroxyphenyl)acetamido, 2-(sodiooxysulfonyl)-2-(p-methoxyphenyl)acetamido, 2-(sodiooxysulfonyl)-2-(m-bromophenyl)acetamido, 2-(sodiooxysulfonyl)-2-(p-chlorophenyl)acetamido, 2-(sodiooxysulfonyl)-2-(3-methyl-4-fluorophenyl)acetamido, 2-(sodiooxysulfonyl)-2-(o-fluorophenyl)acetamido, 2-(sodiooxysulfonyl)2-(p-fluorophenyl)acetamido, 2-(sodiooxysulfonyl)-2-(p-acetamidomethylphenyl)acetamido, 2-(sodiooxysulfonyl)-2-(p-isopropylphenyl)acetamido, 2-(sodiooxysulfonyl)-2-(3,4-dimethylphenyl)acetamido, 2-(sodiooxysulfonyl)-2-(m-isopropoxyphenyl)acetamido, 2-(sodiooxysulfonyl)- 2-(3,4-dimethoxyphenyl)acetamido, 2-(sodiooxysulfonyl)-2-(2-thienyl)acetamido, 2-(potassiooxysulfonyl)-2-(3-thienyl)acetamido, 2-(p-nitrobenzyloxycarbonylamino)-2-phenylacetamido, 2-(tert-butoxycarbonylamino)-2-(2-thienyl)acetamido, 2-(benzyloxycarbonylamino)-2-(m-hydroxyphenyl)acetamido, 2-(tert-butoxycarbonylamino)-2-(p-hydroxyphenyl)acetamido, 2-ureido-2-phenylacetamido, 2-ureido-2-(2-thienyl)acetamido, 2-(3-guanyl-1-ureido)-2-phenylacetamido, 2-(3-methylaminocarbonyl-1-ureido)-2-phenylacetamido, 2-(3-dimethylaminocarbonyl-3-methyl-1-ureido)-2-phenylacetamido, 2-[N-(imidazolidine-2-one-1-ylcarbonyl)amino]-2-phenylacetamido, 2-[N-(3-methylimidazolidine-2-one-1ylcarbonyl)amino]-2-phenylacetamido; 2-[N-(hexahydropyrimidine-2-one-1-ylcarbonyl)amino]-2-phenylacetamido; 2-[N-(3-methylhexahydropyrimidine-2-one-1-ylcarbonyl)amino]-2-phenylacetamido; 2-[N-(3-methanesulfonylhexahydropyrimidine-2-one-1-ylcarbonyl)amino]-2-phenylacetamido; 2-(3-di-n-propylaminocarbonyl-1-ureido)-2-phenylacetamido, 2-((4-ethyl-2,3-dioxo-1-piperazinyl)carbonylamino)-2-phenylacetamido, 2-(3-(methylsulfonyl)-2-oxo-1-imidazolidinyl)carbonylamino)-2-phenylacetamido, 2-(2-oxo-4-imidazolin-1-yl)carbonylamino)-2-phenylacetamido, 2-((4-oxo-4H-thiopyran-3-yl)-carbonylamino)-2-phenylacetamido, 2-(3-methyl-3-(methylcarbamoyl)ureido)-2-phenylacetamido, 2-(3-methyl-3-(cinnamoylureido))-2-phenylacetamido, 2-(3-methyl-3-(acryloylureido))-2-phenylacetamido, 2-((4-ethyl-2,3-dioxo-1-piperazinyl)carbonylamino)-2-thienylacetamido, 2-((4-ethyl-2,3-dioxo-1-piperazinyl)carbonylamino)-2-(p-hydroxyphenyl)acetamido, 2-((4-ethyl-2,3-dioxo-1-piperazinyl)carbonylamino)-2-phenylacetamido, 2-((2-oxoimidazolidin-1-yl)carbonylamino)-3-thienylacetamido, 2-((2-oxo-3-(methylsulfonyl)-4-imidazolin-1-yl)carbonylamino)-2-(p-hydroxyphenyl)acetamido, and the like.

The following are illustrative of the group

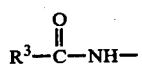

wherein $R^3$ is moiety (15): 2-(hydroxyimino)-2-phenylacetamido, 2-(methoxyimino)-2-phenylacetamido, 2-(acetoxyimino)-2-phenylacetamido, 2-(hydroxyimino)-2-(2-thienyl)acetamido, 2-(hydroxyimino)-2-(2-furyl)acetamido, 2-(methoxyimino)-2-(3-thienyl)acetamido, 2-(methoxyimino)-2-(2-furyl)acetamido, 2-(methoxyimino)-2-(p-hydroxyphenyl)-acetamido, 2-(hydroxyimino)-2-(2-(2,2,2-trichloroethoxycarbonylamino)-4-thiazolyl)acetamido, (tautomeric with 2-(hydroxyimino)-2-(2-(2,2,2-trichloroethoxycarbonylimino)-4-thiazolin-4-yl)acetamido), 2-(methoxyimino)-2-(2-(p-nitrobenzyloxycarbonylamino)-4-thiazolyl)acetamido (tautomeric with 2-(methoxyimino)-2-(2-(p-nitrobenzyloxycarbonylimino)-4-thiazolin-4-yl)acetamido), 2-(methoxyimino)-2-(4-chlorophenyl)acetamido, and the like.

The following are illustrative of the group

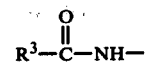

wherein $R^3$ is moiety (16): 2-(trifluoromethylthio)acetamido, 2-(methylsulfonyl)acetamido, 2-(cyanomethylthio)acetamido, 2-(azidomethylthio)acetamido, 2-(ethylsulfonyl)acetamido, 2-(2,2,2-trifluoroethylthio)acetamido, 2-(methylsulfinyl)acetamido, 2-(cyanomethylsulfinyl)acetamido, and the like.

Illustrative of the group

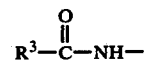

in the above definition in which $R^3$ is Y —CH$_2$— (moiety (17)) are the following: 2-(2-thienyl)acetamido, 2-(3-thienyl)acetamido, 2-(2-furyl)acetamido, 2-(2-oxazolyl)acetamido, 2-(2-thiazolyl)acetamido, 2-(1-tetrazolyl)acetamido, 2-(1-benzotriazolyl)acetamido, 2-(2-oxazolylthio)acetamido, 2-(2-thiazolylthio)acetamido, 2-(1,2,3-triazol-5-ylthio)-acetamido, 2-(1,3,4-triazol-2-yl-thio)acetamido, (1,3,4-thiadiazol-2-ylthio)acetamido, 2-(5-(protected amino)-1,3,4-thiadiazol-2-ylthio)acetamido, 2-(5-methyl-1,3,4-thiadiazol-2-ylthio)acetamido, 2-(1,2,4-thiadiazol-5-ylthio)acetamido, 2-(3-methyl-1,2,4-thiadiazol-5-ylthio)acetamido), 2-(1,2,5-thiadiazol-3-ylthio)acetamido, 2-(1,3,4-oxadiazol-2-ylthio)acetamido, 2-(5-methyl-1,3,4-oxadiazol-2-ylthio)acetamido, 2-(1-methyl-5-tetrazolylthio)acetamido, 2-(pyridylthio)acetamido, 2-(4-cyano-1,2,3-triazol-1-yl)acetamido, 2-(3-cyano-1,2,4-triazol-1-yl)acetamido, and 2-(2-protected amino)-4-thiazolyl)acetamido(tautomeric with 2-(2-imino-4-thiazolin-4yl)acetamido).

Many of the cephalosporanic acids to be employed as starting material in the present process are known compounds, and all are prepared by methods known to those skilled in the art. Attention is directed to "Cephalosporins And Pencillins, Chemistry and Biology", edited by Edwin H. Flynn (Academic Press, New York, 1972). See especially Chapters 3, 4, and 15, and the references there cited. See also U.S. 3,914,157 and South African Patent 71/3229.

Detailed Description of the Invention

Sulfur Nucleophile

The sulfur nucleophile to be employed in accordance with the present process is of the following formulae:

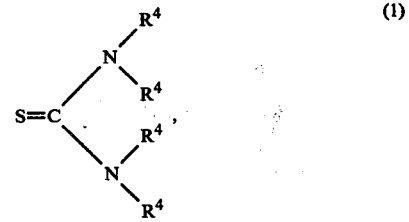

(1)

wherein each $R^4$ is independently
(a) hydrogen, (b) $C_1$-$C_4$ alkyl,
(c) $C_2$-$C_3$ alkenyl,
(d) cyclohexyl, or
(e) phenyl;

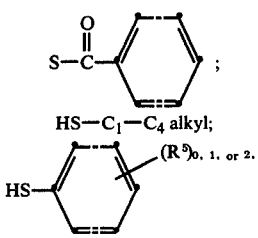 (2)

HS—$C_1$—$C_4$ alkyl; (3)

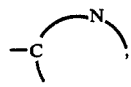 (4)

wherein each $R^5$ is independently $C_1$-$C_4$ alkyl, $C_1$-$C_4$ alkoxy, halo, hydroxy, nitro, cyano, methanesulfonamido, or trifluoromethyl;

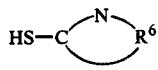 (5)

wherein $R^6$ is
(1) a unit which with the

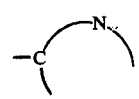

comprises an unsubstituted or substituted, five- or six-membered, heteroaromatic ring having a total of from 1 to 4 hetero atoms selected from the following combinations:
1 nitrogen and 0 or 1 oxygen or sulfur,
2 nitrogens and 0 or 1 oxygen or sulfur,
3 nitrogens and 0 or 1 oxygen,
4 nitrogens,
all other ring atoms being carbon; or
(2) a unit which with the

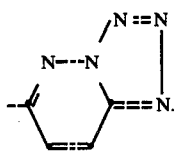

comprises 2-benzimidazolyl, 2-benzothiazolyl, 2-benzoxazolyl, or a radical of the formula

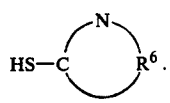

The term "heteroarylthiol" is employed herein to refer to a thiol of the formula

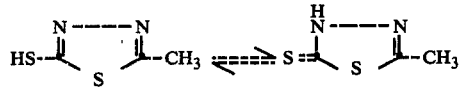

Suitable five-membered heteroaromatic rings in accordance with the foregoing definition of heteroarylthiol include the following
pyrrole
oxazole
isoxazole
thiazole
isothiazole
pyrazole
imidazole
1,2,3-oxadiazole
1,2,4-oxadiazole
1,2,5-oxadiazole
1,3,4-oxadiazole
1,2,3-thiadiazole
1,2,4-thiadiazole
1,2,5-thiadiazole
1,3,4-thiadiazole
1,2,3-triazole
1,2,4-triazole
oxatriazole
tetrazole
Suitable six-membered rings include the following:
pyridine
pyridazine
pyrimidine
pyrazine
1,2,3-triazine
1,2,4-triazine
1,3,5-triazine
1,2,3,4-tetrazine
1,2,4,5-tetrazine Certain of the heteroarylthiols, as well as certain of the alkylthiols and phenylthiols, actually exist as thiones or as tautomeric mixtures of thiol and thione. As an example, the compound 2-methyl-1,3,4-thiadiazole-5-thiol exists as a tautomer:

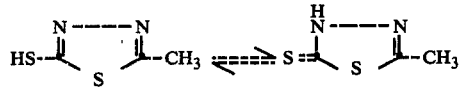

However, the present reaction proceeds with the designated classes of sulfur nucleophiles regardless of whether the reactant is in the thiol or in the thione form. Accordingly, it is within the scope of the present invention to conduct the reaction employing a thione or thiol-thione tautomer of a designated reactant.

The heteroarylthiol can be unsubstituted or can be substituted by one or more substituents. In general, the identity of substituents is not critical. For best results, any primary or secondary amino group should be protected. Where a heteroarylthiol contains more than one thiol group, the one which is desired not to undergo reaction should be protected. Methods for protection of thiols are well known; see McOmie, supra. Assuming the protection of such groups, the reaction goes forward regardless of the identity of substituent.

It is preferred to avoid excessively bulky substitution; generally, substitution not exceeding a molecular weight of about 500 is preferred. Most common substituted heteroaromatic rings contain substitution of a total molecular weight less than about 250.

Suitable substituents include $C_1$-$C_4$ alkyl, $C_2$-$C_4$ alkenyl, $C_2$-$C_4$ alkynyl, $C_5$-$C_6$ cycloalkyl, benzyl, phenethyl, aryl including phenyl and substituted phenyl as defined hereinabove, halo —$CF_3$, =O, —OH, protected amino or $C_1$-$C_4$ alkylamino, —COOH, —COOA$^2$, —CONH$_2$, protected aminomethyl or $C_1$-$C_4$ alkylaminomethyl, —$CH_2SO_3$-alkali metal, —$CH_2COOH$, —$CH_2COOA^2$, or —$(CH_2)_2N(CH_3)_2$.

Representative sulfur nucleophiles to be employed in accordance with the present invention, include the following:

Thioureas
allylthiourea
N,N'-di-n-butylthiourea
N,N'-di-tert-butylthiourea
N,N'-dicyclohexylthiourea
N,N'-diisopropylthiourea
N,N'-dimethylthiourea
N-methylthiourea
N,N,N',N'-tetraethylthiourea
N,N,N',N'-tetramethylthiourea
thiourea
N-phenylthiourea
N,N'-diphenylthiourea
N,N-dimethylthiourea
  Thiobenzoic acid
  Alkylthiols
methanethiol
ethanethiol
1- or 2-propanethiol
1- or 2-butanethiol
2-methyl-1-propanethiol
  Benzenethiols
benzenethiol
4-bromo-3-methylbenzenethiol
p-bromobenzenethiol
p-chlorobenzenethiol
2,5-dichlorobenzenethiol
3,4-dichlorobenzenethiol
4-fluorobenzenethiol
m-methoxybenzenethiol
p-methoxybenzenethiol
p-nitrobenzenethiol
p-methylbenzenethiol
  Heteroarylthiols
2-pyrrolethiol
3-pyrazolethiol
2-methyl-3-pyrazolethiol
2-methyl-4-imidazolethiol
2-imidazolethiol
4-oxazolethiol
3-isoxazolethiol
2-thiazolethiol
3-isothiazolethiol
1-methyl-1,2,3-triazole-5-thiol
1-benzyl-1,2,3-triazole-4-thiol
2-methyl-1,2,3-triazole-4-thiol
3,5-dimethyl-1,2,3-triazole-4-thiol
1,2,4-triazole-3-thiol
4-methyl-1,2,4-triazole-5-thiol
3-methyl-1,2,4-triazole-5-thiol
3,4-dimethyl-1,2,4-triazole-5-thiol
2-methyl-1,2,4-triazole-5-thiol
2-benzyl-1,2,4-triazole-5-thiol
2,3-dimethyl-1,2,4-triazole-5-thiol
4-methyl-3-(trifluoromethyl)-1,2,4-triazole-5-thiol
3-carbamoyl-4-methyl-1,2,4-triazole-5-thiol
3-(carboxymethyl)-4-methyl-1,2,4-triazole-5-thiol
3-(carboethoxymethyl)-4-methyl-1,2,4-triazole-5-thiol
protected 3-amino-4-methyl-1,2,4-triazole-5-thiol
3-hydroxy-4-methyl-1,2,4-triazole-5-thiol
5-methyl-1,2,3-oxadiazole-4-thiol
1,2,4-oxadiazole-3-thiol
3-methyl-1,2,4-oxadiazole-5-thiol
3-methyl-1,2,5-oxadiazole-4-thiol
2-methyl-1,3,4-oxadiazole-5-thiol
3-methyl-1,2,4-thiadiazole-5-thiol
1,3,4-thiadiazole-5-thiol
2-methyl-1,3,4-thiadiazole-5-thiol
2-(N-methylacetamido)-1,3,4-thiadiazole-5-thiol
5-tetrazolethiol
1-methyltetrazole-5-thiol
1-benzyltetrazole-5-thiol
1-(carboxymethyl)tetrazole-5-thiol
1-((sodiooxysulfonyl)methyl)tetrazole-5-thiol
1-(2-dimethylaminoethyl)tetrazole-5-thiol
1,2,3,4-oxatriazole-5-thiol
2-pyridinethiol
2-pyridinethiol, 1-oxide
3pyridazinethiol
2-pyrimidinethiol
2-pyrazinethiol
1,2,3-triazine-4-thiol
1,2,4-triazine-3-thiol
4,5-dihydro-6-hydroxy-4-methyl-5-oxo-1,2,4-triazine-3-thiol
1,3,5-triazine-2-thiol
1,2,4,5-tetrazine-3-thiol
2-benzimidazolethiol
2-benzothiazolethiol
2-benzoxazolethiol
tetrazolo(1,5-b)pyridazine-6-thiol.

Most of the sulfur nucleophiles to be employed in the present process are known compounds, and all can be prepared in accordance with prior art procedures. In the case of the heteroarylthiols, attention is directed to the numerous volumes of "Heterocyclic Compounds", edited by Robert C. Elderfield (John Wiley and Sons, Inc., N.Y.), as well as the various volumes on the particular heterocyclic systems in the series "The Chemistry of Heterocyclic Compounds," edited by Weissberger et al. (John Wiley and Sons, N.Y.).

Detailed Description of the Invention

Reaction Conditions

It is critical to the present invention that the reaction be carried out in an organic solvent. However, the identity of the solvent is not critical, since a great variety of organic solvents has proven satisfactory. In general, members of the following classes of solvents have been found satisfactory: hydrocarbons, both aliphatic and aromatic, alcohols, amides, ethers, ketones, carboxylic acids, carboxylic acid esters, halogenated hydrocarbons, nitro compounds, nitriles, and thioethers. Of these, alcohols, amides, and ethers have generally been found to be less suitable than the remaining classes. Since certain of the nucleophiles are liquids, an excess of such reactant can also be employed as solvent.

The solvent should be inert, in the sense that it does not undergo a competing reaction with either reactant. For example, solvents comprising an aliphatic bromine are disfavored because of their potential for reacting with the sulfur nucleophile.

Particular solvents which are suitable in carrying out the present practice include pentane, cyclopentane, hexane, heptane, octane, benzene, toluene, o-, m-, or p-xylene, cumene, mesitylene, p-cymene, 1-pentene, diethyl ether, butyl ethyl ether, diamyl ether, benzyl ethyl ether, acetone, methyl ethyl ketone, 2-butanone, 3-pentanone, methyl isobutyl ketone, cyclohexanone, acetic acid, propionic acid, butyric acid, isobutyric acid, valeric acid, methyl acetate, ethyl acetate, propyl acetate, isopropyl acetate, ethyl propionate, butyl acetate, isobutyl acetate, secbutyl acetate, amyl acetate, isoamyl acetate, ethyl isovalerate, methyl benzoate, benzyl acetate, methyl butyrate, diethyl carbonate, dimethyl maleate, diethyl oxalate, ethylene glycol diacetate, diethyl malonate, fluorobenzene, chlorobenzene, bromobenzene, o-, m- or p-fluorotoluene, o-, m-, or p-chlorotoluene, o-, m-, or p-bromotoluene, 2-chloroethane, 1- or 2-chloropropane, 1- or 2-chlorobutane, 1-chloro-2-methylpropane, 1, 2, or 3-chloropentane, 1-chloronaphthalene, methylene chloride, chloroform, carbon tetrachloride, 1,1-dichloroethane, 1,2-dichloroethane, 1,1,1-trichloroethane, 1,1,2-trichloroethane, 1,1,2,2-tetrachloroethane, o-, m-, or p-dichlorobenzene, nitromethane, nitroethane, 1- or 2-nitropropane, nitrobenzene, acetonitrile, propionitrile, butyronitrile, isobutyronitrile, valeronitrile, benzonitrile, phenylacetonitrile, and thiophene.

Preferred solvents are:
Hydrocarbons
benzene
toluene
o-, m-, or p-xylene
cumene
mesitylene
Halogenated Hydrocarbons
chloroethane
1- or 2-chloropropane
1- or 2-chlorobutane
isobutyl chloride
1,2, or 3-chloropentane
methylene chloride
chloroform
1,2-dichloroethane
carbon tetrachloride
1,1,1-trichloroethane
1,1,2-trichloroethane
1,1,2,2-tetrachloroethane
fluorobenzene
chlorobenzene
bromobenzene
o-, m-, or p-fluorotoluene
o-, m-, or p-chlorotoluene
o-, m-, or p-bromotoluene
o-, m-, or p-dichlorobenzene
Acids
acetic acid
propionic acid
butyric acid
isobutyric acid
valeric acid
Esters
methyl acetate
ethylene glycol diacetate
ethyl acetate
propyl acetate
isopropyl acetate
butyl acetate
isobutyl acetate
sec-butyl acetate
pentyl acetate
ethyl propionate
methyl butyrate
n-butyl formate
propylene carbonate
ethylene carbonate
Nitro Compounds
nitrobenzene
nitromethane
nitroethane
nitropropane
Nitriles
acetonitrile
propionitrile
butyronitrile
isobutyronitrile
valeronitrile
benzonitrile
phenylacetonitrile
Ketones
methyl isobutyl ketone
methyl ethyl ketone Especially preferred solvents are acetonitrile, 1,2-dichloroethane, methylene chloride, propionitrile, nitromethane, nitroethane, acetic acid, isopropyl acetate, butyl acetate, and methyl isobutyl ketone.

The 3-(acyloxymethyl)cephalosporin reactant has been defined as the acid. It is believed to be the acid which undergoes reaction, since cephalosporin salts are generally not soluble in organic solvents. The exception is the solubility of cephalosporin salts in carboxylic acid solvents, such as acetic acid. Therefore, the present reaction can be accomplished by dissolving a 3-(acyloxymethyl)cephalosporin salt, such as a metal salt, in a carboxylic acid solvent.

Regardless of the identity of the solvent, it is necessary that the present process be conducted under essentially anhydrous conditions. In general, the reaction mixture should contain less than about 5 percent of water, and preferably less than about 1 percent of water. It is even more preferred that the amount of water be less than 0.5 percent. Where commercial sources of reactants and solvents are not dry enough, removal of water can be carried out in accordance with known procedures, including azeotroping and the use of drying agents such as alumina, silica gel, anhydrous calcium sulfate, and the like.

The present reaction goes forward under a wide range of temperatures. In general, reaction temperatures of 50°–140° C. can be used; but better results are usually achieved at temperatures of 70°–120° C. The reaction can be conducted at elevated pressures, but no advantages have been observed. Hence atmospheric pressure is generally preferred because of its simplicity.

The amounts of the reactants are not critical. In general, an excess of the sulfur nucleophile is preferred, such as 1.0 to 5.0 molar equivalents of sulfur nucleophile per molar equivalent of the 3-(acyloxymethyl)cephalosporin reactant.

The present process is particularly useful for the introduction into cephalosporins of the following 3-heteroarylthio groups:

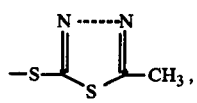

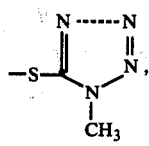

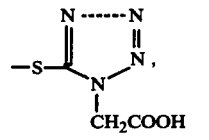
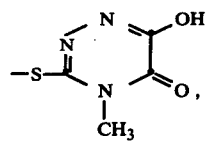
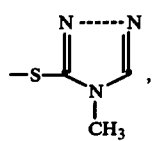
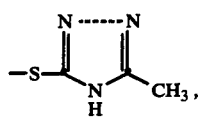
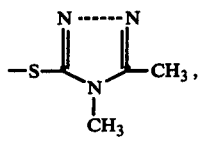
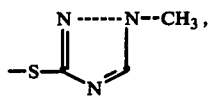
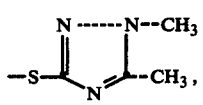
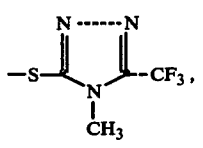
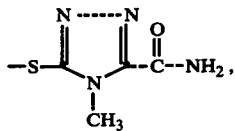
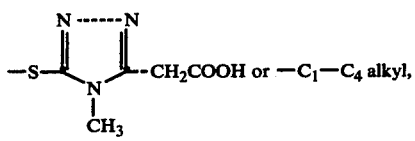
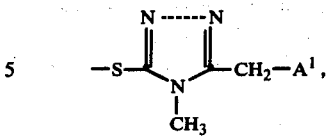
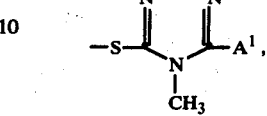
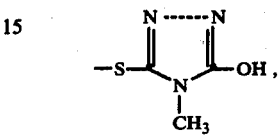
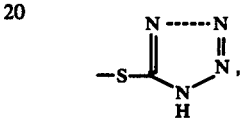
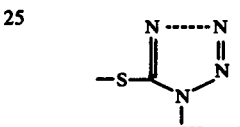
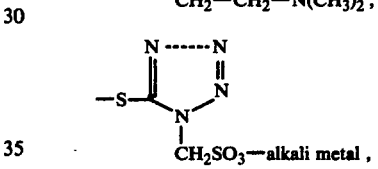
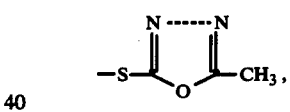
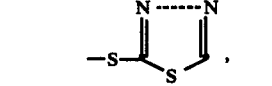
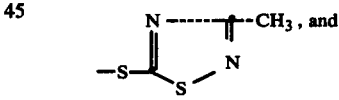
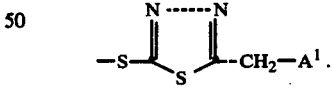
Among the known cephalosporin compounds which can be prepared by synthetic routes incorporating the present process are the following:
cefamandole: 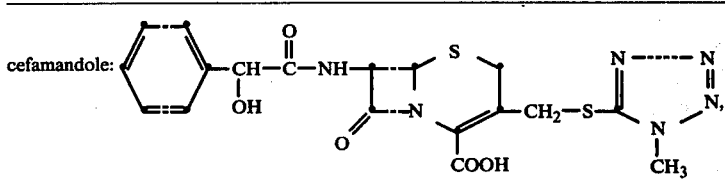

-continued
cefamandole nafate: 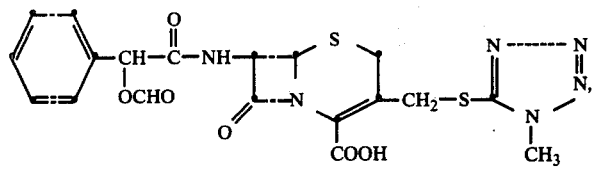
cefazolin: 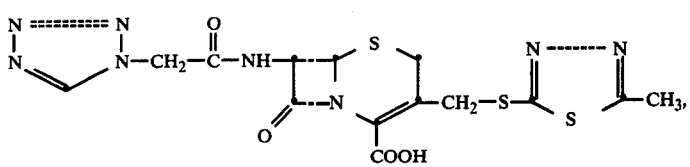
ceftezole: 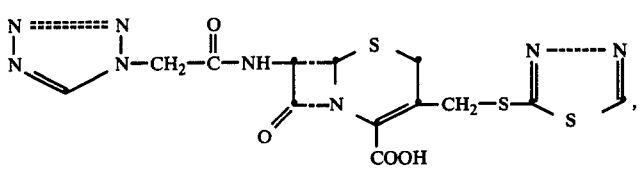
cefazaflur: 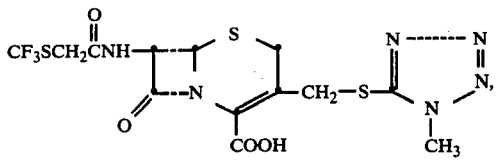
SCE-963: 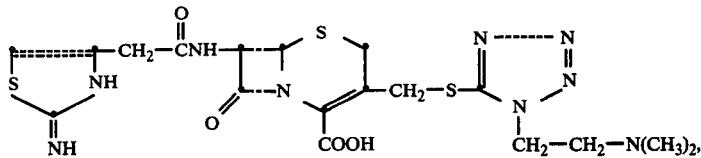
BLS-786: 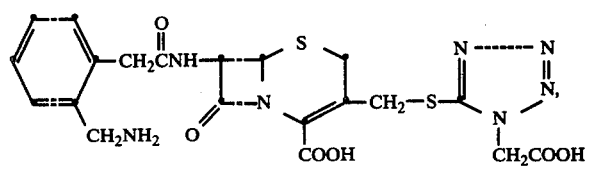
CS-1170: 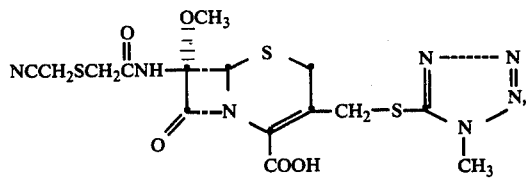
SQ-67,590: 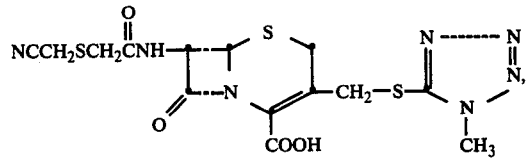
SKF-75073: 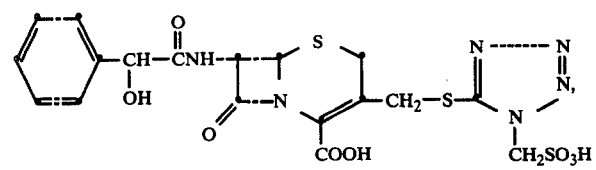
BBS-226: 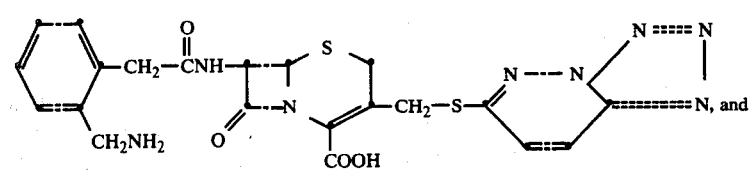

SQ-14,359:

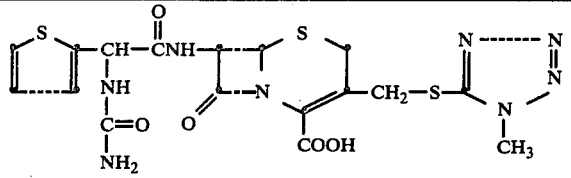

The products of the present invention, their deblocked derivatives, and the pharmaceutically acceptable salts of the same are useful in combating infections in warm-blooded mammals when administered parenterally in non-toxic doses between about 10 and 500 mg./kg. of body weight. The compounds are formulated in conventional procedures.

The following examples illustrate the present invention and will enable those skilled in the art to practice the same.

EXAMPLE 1

PREPARATION OF
3-(((1-METHYL-1H-TETRAZOL-5-YL)THIO)METHYL)-7-(2-(2-THIENYL)ACETAMIDO)-3-CEPHEM-4-CARBOXYLIC ACID IN ACETONITRILE 7-(2-(2-Thienyl)acetamido)cephalosporanic acid (2.2 grams; 5.5 mmole) and 1-methyl-1H-tetrazole-5-thiol (1.0 gram; 8.6 mmole) were added to 25 ml. of acetonitrile in a flask equipped with a condenser with a drying tube containing anhydrous calcium sulfate sold under the trademark Drierite. The reaction mixture was refluxed, with stirring, and the progress of the reaction was monitored by TLC. After 90 minutes at reflux, TLC showed about two-thirds cephalosporanic acid starting material and one-third of the desired product. After 3 hours of reflux, TLC showed about one-third cephalosporanic acid starting material and two-thirds product. After 6 hours, at which time TLC showed the reaction essentially complete, the reaction mixture was cooled to room temperature and allowed to stand overnight. Solvent was removed on a rotary evaporator, leaving as a residue a foam which was dissolved in 10 ml. of ethanol. Dropwise addition of 1 ml. of dicyclohexylamine in 10 ml. of ethanol resulted in the precipitation of product as the dicyclohexylamine salt which, after 15 minutes of stirring, was separated by filtration. The isolated product was washed with 15 ml. of ethanol, and the product was vacuum dried at 40° C. for 2 hours, 2.50 grams (76.1 percent yield), m.p., 183°–4° C. (dec). The product was subjected to NMR, IR, and TLC, and all of these analyses were identical with analyses of an authentic sample of the product prepared by the prior art aqueous displacement. NMR(DMSO-$d_6$) δ 3.52 (m, 2, 2—C$\underline{H}_2$), 3.76 (s, 2, —C$\underline{H}_2$CONH—), 3.92 (s, 3, —C$\underline{H}_3$ of tetrazole), 4.35 (s, 2, 3—C$\underline{H}_2$S), 5.00 (d, 1, C$_6$-$\underline{H}$, J=5 Hz), 5.55 (q, 1, C$_7$-$\underline{H}$, J=5 Hz, $\underline{J}$=9 Hz), 6.95 (d, 2, thiophene 3 and 4-$\underline{H}$, J=3 Hz), 7.35 (t, 1, thiophene 5-$\underline{H}$, $\underline{J}$=3 Hz), and 8.75 (d, 1, —CH$_2$CON$\underline{H}$—, $\underline{J}$=9 Hz).

EXAMPLE 2

PREPARATION OF
3-(((1-METHYL-1H-TETRAZOL-5-YL)THIO)METHYL)-7-(2-(2-THIENYL)ACETAMIDO)-3-CEPHEM-4-CARBOXYLIC ACID IN ACETONITRILE 7-(2-(2-Thienyl)acetamido)cephalosporanic acid (4.0 grams; 10 mmole) and 1-methyl-1H-tetrazole-5-thiol (5.8 grams; 50 mmole) were refluxed in 50 ml. of dry acetonitrile (treated over a anhydrous sulfonic acid resin sold under the trademark Amberlite 15), under a dry atmosphere, for 8¾ hours. The reaction was followed by TLC and was nearly complete at the end of 8¾ hours.

Solvent was removed by evaporation and the residue added to 125 ml. of ethanol. Dicyclohexylamine (6 ml.) in 75 ml. of ethanol was added and the product precipitated as the dicyclohexylamine salt. It was separated by filtration, washed, and dried, 4.50 grams (71.0 percent yield). IR, NMR, and TLC were identical to an authentic sample prepared by aqueous displacement. The NMR was also identical with the NMR on the product of Example 1.

EXAMPLE 3

PREPARATION OF
3-(((1-METHYL-1H-TETRAZOL-5-YL)THIO)METHYL)-7-(2-(2-THIENYL)ACETAMIDO)-3-CEPHEM-4-CARBOXYLIC ACID IN 1,2-DICHLOROETHANE 7-(2-(2-Thienyl)acetamido)cephalosporanic acid (2.0 grams; 5 mmole) and 1-methyl-1H-tetrazole-5-thiol (1.2 grams; 10 mmole) in 25 ml. of 1,2-dichloroethane were refluxed under a dry atmosphere for a total of 5.5 hours. Solvent was then removed on a rotary evaporator, and 25 ml. of ethanol was added to the filtrate followed by dropwise addition of a solution of 2 ml. of dicyclohexaylamine in 25 ml. of ethanol. The product crystallized as the dicyclohexylamine salt and was stirred for 20 minutes at room temperature, then filtered, washed with 25 ml. of ethanol, and dried at 40° C. under vacuum, 2.34 grams of off-white solid (73.8 percent yield). IR and NMR were identical with an authentic sample prepared by aqueous displacement. The NMR was also identical with the NMR on the product of Example 1.

EXAMPLE 4

PREPARATION OF
3-(((1-METHYL-1H-TETRAZOL-5-YL)THIO)METHYL)-7-AMINO-3-CEPHEM-4-CARBOXYLIC ACID IN 1,2-DICHLOROETHANE

7-Formamidocephalosporanic acid (3.0 grams; 10 mmole) and 1-methyl-1H-tetrazole-5-thiol (2.4 grams; 20 mmole) in 50 ml. of 1,2-dichloroethane were stirred and refluxed for 7 hours. The reaction mixture was then cooled to room temperature and allowed to stand overnight at room temperature. A red gummy solid precipitated.

Solvent was removed on a rotary evaporator and the residue was dissolved in 25 ml. of methanol and 2.8 ml. of concentrated HCl and permitted to stand overnight at room temperature. The solution was then diluted to 50 ml. with water, and the pH, initially 0.9, was raised to 3.6 by dropwise addition of triethylamine. Light brown crystals were filtered, washed with water, and dried, 2.10 grams (64 percent yield). The NMR was identical with the same product made by aqueous displacement. NMR(D$_2$O, NaHCO$_3$) δ 3.65 (q, 2, 2—C$\underline{H}_2$, $J_{AB}$=16.5 Hz), 4.08 (s, 3, —CH$_3$ on tetrazole), 4.16 (q, 2, 3—C$\underline{H}_2$S—, $J_{AB}$=12.5 Hz), 5.05 (d, 1, C$_6$-$\underline{H}$, J=5 Hz), and 5.45 (d, 1, C$_7$-$\underline{H}$, J=5 Hz).

EXAMPLE 5

PREPARATION OF 3-(((1-METHYL-1H-TETRAZOL-5-YL)THIO)METHYL)-7-(2-(2-THIENYL)ACETAMIDO)-3-CEPHEM-4-CARBOXYLIC ACID IN ISOPROPYL ACETATE 7-(2-(2-Thienyl)acetamido)cephalosporanic acid (2.0 grams; 5 mmole) and 1-methyl-1H-tetrazole-5-thiol (1.2 grams: 10 mmole) in 25 ml. of ispropyl acetate were refluxed (90° C.) with stirring for 23 hours.

The reaction mixture was then cooled to room temperature. TLC showed some of the cephalosporanic acid starting material remaining. The light cream colored solid was separated by filtration, washed with isopropyl acetate and dried, 1.60 grams (70.8 percent yield). NMR confirmed the identity of the product and showed less than 1 percent of the cephalosporanic acid starting material present. NMR (DMSO-d$_6$) δ 3.72 (s, 2, 2—C$\underline{H}_2$), 3.80 (s, 2, —C$\underline{H}_2$CONH—), 3.95 (s, 3, —CH$_3$ of tetrazole), 4.30 (s, 2, 3—C$\underline{H}_2$S—), 5.10 (d, 1, C$_6$-$\underline{H}$, J=5 Hz), 5.70 (q, 1, C$_7$-$\underline{H}$, J=5 Hz, $\underline{J}$=8 Hz), 6.92 (d, 2, thiophene 3- and 4-H, $\underline{J}$=3 Hz), 7.35 (t, 1, thiophene 5-H, $\underline{J}$=3 Hz), and 8.78 (d, 1, —CH$_2$CON$\underline{H}$—, $\underline{J}$=8 Hz).

EXAMPLE 6

PREPARATION OF 3-(((1-METHYL-1H-TETRAZOL-5-YL)THIO)METHYL)-7-(2-(2-THIENYL)ACETAMIDO)-3-CEPHEM-4-CARBOXYLIC ACID IN PROPIONITRILE 7-(2-(2-Thienyl)acetamido)cephalosporanic acid (2.0 grams; 5 mmole) and 1-methyl-1H-tetrazole-5-thiol (1.2 grams; 10 mmole) were refluxed in 25 ml. of dry propionitrile (97° C.) until TLC showed the complete disappearance of cephalosporanic acid starting material (4.5 hours). The reaction mixture was then cooled to room temperature, and solvent was removed on a rotary evaporator, during which process some of the solution was lost due to bumping. The residue was dissolved in 35 ml. of warm ethanol and a solution of 2 ml. of dicyclohexylamine in 10 ml. of ethanol was added. The product precipitated as the dicyclohexylamine salt and was stirred 10 minutes at room temperature, then filtered, washed with ethanol and dried, 1.24 grams (39.0 percent yield, not including product lost on the rotary evaporator). The NMR of the product was identical with the NMR on the Example 1 product.

EXAMPLE 7

PREPARATION OF 3-(((1-METHYL-1H-TETRAZOL-5-YL)THIO)METHYL)-7-(2-(2-THIENYL)ACETAMIDO)-3-CEPHEM-4-CARBOXYLIC ACID IN ACETONITRILE, 3,5-DICHLOROPHENYL DIHYDROGEN PHOSPHATE ADDED 7-(2-(2-Thienyl)acetamido)cephalosporanic acid (2.0 grams; 5 mmole), 1-methyl-1H-tetrazole-5-thiol (0.87 gram; 7.5 mmole), and 3,5-dichlorophenyl dihydrogen phosphate (0.122 grams; 0.5 mmole) were heated overnight in 25 ml. of dry acetonitrile at about 70° C. Solvent was then removed on a rotary evaporator to about 8-10 ml. The product began to crystallize. After stirring for ½ hour, isopropyl acetate (25 ml.) was added dropwise during ½ hour to effect further crystallization. After an additional ½ hour of stirring, the product was separated by filtration, washed with isopropyl acetate and dried, 0.98 gram (43.4 percent yield). The NMR of the product was identical with the NMR on the Example 5 product.

EXAMPLE 8

PREPARATION OF 3-(((1H-TETRAZOL-5-YL)THIO)METHYL)-7-(2-(2-THIENYL)ACETAMIDO)-3-CEPHEM-4-CARBOXYLIC ACID IN ACETIC ACID 7-(2-(2-Thienyl)acetamido)cephalosporanic acid (2.0 grams; 5 mmole) and 1-methyl-1H-tetrazole-5-thiol (0.87 grams; 7.5 mmole) were added to glacial acetic acid (25 ml.). The reaction mixture was heated to 60° C. and held at this temperature for an hour. Only a trace of product was evident on TLC. The reaction mixture was heated to 80° C. and held at this temperature for 5 hours. The reaction mixture was then allowed to stand overnight, and the product was separated by filtration, washed with acetic acid, and dried, 0.71 gram (31 percent yield). The NMR of the product was identical with the NMR on the Example 5 product.

EXAMPLE 9

PREPARATION OF 3-(((4,5-DIHYDRO-6-HYDROXY-4-METHYL-5-OXO-1,2,4-TRIAZIN-3-YL)THIO)METHYL)-7-(2-(2-THIENYL)ACETAMIDO)-3-CEPHEM-4-CARBOXYLIC ACID IN ACETONITRILE 7-(2-(2-Thienyl)acetamido)cephalosporanic acid (2.0 grams; 5 mmole) and 4,5-dihydro-6-hydroxy-4-methyl-5-oxo-1,2,4-triazine-3-thiol (1.2 grams; 7.5 mmole) were added to 25 ml. of dry acetonitrile in a reaction flask immersed in an oil bath at 84°-85° C. The flask was equipped with a condenser with a drying tube containing anhydrous calcium sulfate sold under the trademark Drierite. The reaction mixture was maintained for 16 hours in this condition, with slow magnetic agitation.

The product crystallized from the hot solution. The reaction mixture was cooled to room temperature, filtered, washed with acetonitrile, washed with acetone, and vacuum dried, 1.81 grams (72.6 percent yield). The product was off-white crystals, m.p. 161° C. (dec).

On standing, the filtrate deposited a second crop of crystals. This crop was separated by filtration, washed with acetonitrile, and dried, 0.26 gram (10.5 percent yield). This second crop also melted at 161° C. (dec).

Total yield was therefore 83.1 percent.

EXAMPLE 10

PREPARATION OF 3-(((5-METHYL-1,3,4-OXADIAZOL-2-YL)THIO)METHYL)-7-(2-(2-THIENYL)ACETAMIDO)-3-CEPHEM-4-CARBOXYLIC ACID IN 1,2-DICHLOROETHANE 7-(2-(2-Thienyl)acetamido)cephalosporanic acid (2.0 grams; 5 mmole) and 5-methyl-1,3,4-oxadiazole-2-thiol (0.87 gram; 7.5 mmole) in 25 ml. of 1,2-dichloroethane were placed in a flask equipped with magnetic stirring bar and condensor with a drying tube containing anhydrous calcium sulfate sold under the trademark Drierite.

The flask was immersed in an oil bath at 84°–85° C. and held of 8 hours, then refrigerated for two days.

A portion of product had crystallized; it was separated by filtration, washed with 1,2-dichloroethane, and dried, 1.10 grams (48.7 percent yield). It was dissolved in 15 ml. of acetone and filtered to remove an insoluble product. Then 75 ml. of deionized water was added dropwise and the product was separated by filtration and dried, 0.61 gram, m.p. >114° C. (dec.).

Evaporation of solvent from the filtrate yielded 0.23 gram of a mixture of product and both starting materials.

EXAMPLE 11

PREPARATION OF 3-(((1-METHYL-1H-TETRAZOL-5-YL)THIO)METHYL)-7-(2-(2-THIENYL)ACETAMIDO)-3-CEPHEM-4-CARBOXYLIC ACID IN NITROMETHANE 7-(2-(2-Thienyl)acetamido)cephalosporanic acid (2.0 grams; 5 mmole) and 1-methyl-1H-tetrazole-5-thiol (0.87 gram; 7.5 mmole) were added to 25 ml. of dry nitromethane in a flask; the flask was immersed in an oil bath at 100°–101° C. for 4.5 hours, then cooled to room temperature. TLC showed that the reaction was complete.

Solvent was removed on a rotary evaporator, and the residue was dissolved in 75 ml. of warm ethyl acetate. The solution was filtered to remove a small amount of insolubles, then extracted with two 25-ml. portions of 5 percent aqueous sodium bicarbonate. The combined extracts were layered with 50 ml. of ethyl acetate and acidified to pH about 1.0 with 70 percent aqueous methanesulfonic acid. The ethyl acetate layer was separated and the water layer was extracted with 25 ml. of ethyl acetate. The ethyl acetate layers were combined, dried over anhydrous sodium sulfate, and concentrated to 25 ml. on a rotary evaporator. Dropwise addition of 50 ml. of diethyl ether resulted in crystallization of the product. It was separated by filtration, washed with diethyl ether, and dried, 1.27 gram (56.2 percent yield), off-white crystals, m.p. 156°–159° C. (dec.). The identity of the product was confirmed by NMR.

EXAMPLE 12

PREPARATION OF 3-(((1-METHYL-1H-TETRAZOL-5-YL)THIO)METHYL)-7-(2-(2-THIENYL)ACETAMIDO)-3-CEPHEM-4-CARBOXYLIC ACID IN METHYLENE CHLORIDE 7-(2-(2-Thienyl)acetamido)cephalosporanic acid (11.9 grams; 30 mmole) and 1-methyl-1H-tetrazole-5-thiol (7.0 grams; 60 mmole) in 300 ml. of methylene chloride (cyclohexane stabilized) were placed in a one-liter stainless steel autoclave equipped with heater. The reaction mixture was stirred and heated to 83°–86° C., developing a pressure of 42 p.s.i., for 16 hours. The reaction mixture was then cooled to room temperature. TLC showed conversion to product, with only a trace of the starting cephalosporanic acid remaining. The reaction mixture was permitted to stand at room temperature, which resulted in crystallization of the product, and then concentrated to about 200 ml. The crystals were filtered off and washed with methylene chloride, 7.37 grams (54.3 percent yield), white crystals, m.p. 163.5°–164° C. (dec.).

A second crop of light tan crystals was obtained by diluting the filtrate with 100 ml. of diethyl ether, filtering, washing with diethyl ether, and drying, 1.40 grams (10.3 percent yield).

A third crop was obtained by diluting the filtrate with isopropyl acetate, 1.18 grams (8.7 percent yield).

Total yield was therefore 73.3 percent.

EXAMPLE 13

PREPARATION OF 3-(((1-METHYL-1H-TETRAZOL-5-YL)THIO)METHYL)-7-(2-(2-THIENYL)ACETAMIDO)-3-CEPHAM-4-CARBOXYLIC ACID IN FLUOROBENZENE 7-(2-(2-Thienyl)acetamido)cephalosporanic acid (2.0 grams; 5.04 mmole) of 1-methyl-1H-tetrazole-5-thiol (1.2 grams; 10 mmole) in 75 ml. of fluorobenzene (b.p. 85.1° C.) were mixed in a flask equipped with a condenser with a drying tube containing anhydrous calcium sulfate sold under the trademark Drierite. The mixture was heated to reflux and progress of the reaction was followed by TLC in 7/1 ethyl acetate/acetic acid. The reaction, which remained heterogeneous throughout, was essentially complete in 72 hours.

The reaction mixture was then cooled to room temperature and filtered to separate the precipitated product. The product was washed with fluorobenzene and vacuum dried at 40° C. for five hours, 2.13 grams (93.4 percent yield), off-white crystals, 161°–162° C. (dec). Identity of the product was confirmed by NMR.

EXAMPLE 14

PREPARATION OF 3-(((1-METHYL-1H-TETRAZOL-5-YL)THIO)METHYL)-7-(2-(2-THIENYL)ACETAMIDO)-3-CEPHEM-4-CARBOXYLIC ACID IN THIOPHENE 7-(2-(2-Thienyl)acetamido)cephalosporanic acid (2.0 grams; 5 mmole) and 1-methyl-1H-tetrazole-5-thiol (0.87 gram: 7.5 mmole) in 25 ml. of thiophene were refluxed for 7 hours, during which time the product crystallized. The reaction mixture was cooled to room temperature, stirred for 30 minutes to complete crystallization, and filtered. The separated product was washed with 0.5 ml. of thiophene, then vacuum dried for 2 hours, 1.82 grams (80.2 percent yield), white crystals, m.p. 162°–163° C. (dec). TLC showed that the filtrate contained additional product.

EXAMPLE 15

PREPARATION OF 3-(((5-METHYL-1,3,4-THIADIAZOL-2-YL)THIO)-METHYL)-7-(2-(1H-TETRAZOL-1-YL)ACETAMIDO)-3-CEPHEM-4-CARBOXYLIC ACID IN ACETONITRILE 7-(2-(1H-Tetrazol-1-yl)acetamido)cephalosporanic acid (0.76 gram; 2 mmole) and 5-methyl-1,3,4-thiadiazole-2-thiol (0.33 gram; 2.5 mmole) in 10 ml. of reagent grade acetonitrile were refluxed for two hours and forty minutes. The product crystallized. The reaction mixture was cooled in an ice bath and filtered to separate the product, which was washed with three ml. of acetonitrile and dried at 40° under vacuum, 0.61 gram (67 percent yield). The identity of the product was confirmed by NMR, δ 2.68 (s, 3, —CH$_3$ of tetrazole), 3.72 (s, 2, 2—CH$_2$), 4.40 (q, 2, 3—CH$_2$S—, J$_{AB}$=13 Hz), 5.12 (d, 1, C$_6$—H, J=5 Hz), 5.38 (s, 2, —CH$_2$CONH—), 5.72 (q, 1, C$_7$—H, J=5 Hz, J=9 Hz), 9.00 (s, 1, tetrazole 5—H), and 9.17 (d, 1, —CH$_2$CONH—).

EXAMPLE 16

PREPARATION OF 3-(((1-METHYL-1H-TETRAZOL-5-YL)THIO)ME-THYL)-7-(2-FORMYLOXY-2-PHENYLACETAMIDO)-3-CEPHEM-4-CARBOXYLIC ACID IN 1,2-DICHLOROETHANE 7-(2-Formyloxy-2-phenylacetamido)cephalosporanic acid (2.17 grams; 5 mmole) and 1-methyl-1H-tetrazole-5-thiol (0.87 grams; 7.5 mmole) were added to 25 ml. of 1,2-dichloroethane, and the resulting reaction mixture refluxed for six hours. Samples were taken for TLC at 3 and 6 hours. The reaction mixture was heated for an additional hour, then allowed to cool overnight.

Solvent was removed by evaporation. Diethyl ether was added to the residue, which turned gummy and then solid. The product was separated by filtration, washed with diethyl ether, and dried, 1.90 grams (77.0 percent yield). NMR(DMSO-$d_6$) δ 3.52 (s, 2, 2—C$\underline{H}_2$), 3.88 (s, 3, —C$\underline{H}_3$ of tetrazole), 4.10 (s, 2, 3—C$\underline{H}_2$S—), 4.92 (d, 1, C$_6$—$\underline{H}$), 5.62 (q, 1, C$_7$-$\underline{H}$, J=5 Hz, J=9 Hz), 6.06 (s, 1,

7.26 (s, 5, phenyl-$\underline{H}$), and 8.28 (s, 1,

EXAMPLE 17

PREPARATION OF 3-(((1-METHYL-1H-TETRAZOL-5-YL)THIO)ME-THYL)-7-(5-CARBOXY-5-(2,4-DICHLOROBEN-ZAMIDO)-VALERAMIDO)-3-CEPHEM-4-CARBOXYLIC ACID IN (A) ACETONITRILE AND (B) 1,2-DICHLOROETHANE (A) 7-(5-Carboxy-5-(2,4-dichlorobenzamido)-valeramido)cephalosporanic acid (2.9 grams; 5 mmole), 1-methyl-1H-tetrazole-5-thiol (1.2 grams; 10 mmole), and 50 ml. of acetonitrile were refluxed overnight (about 18 hours). TLC showed reaction had taken place, estimated to be about 90 percent complete. The reaction mixture was evaporated and the residue slurried in ethyl acetate and filtered, 1.51 grams (48.3 percent yield).

(B) 7-(5-(Carboxy-5-(2,4-dichlorobenzamido)-valeramido)cephalosporanic acid (2.9 grams; 5 mmole), 1-methyl-1H-tetrazole-5-thiol (1.2 grams; 10 mmole) and 50 ml. of 1,2-dichloroethane were refluxed for five and one-half hours. TLC showed that reaction was about 90 percent complete.

Solvent was decanted from the reaction mixture, leaving a plastic-like solid which was triturated under refluxing ether. The product was separated by filtration, 2.83 grams (89.3 percent yield), tan crystals. NMR corroborated the identity of the product but showed ether. NMR (DMSO-$d_6$) δ 1.78 and 2.26 (each m, adipoyl side chain), 3.66 (m, 2, 2—C$\underline{H}_2$), 3.95 (s, 3, —C$\underline{H}_3$ of tetrazole), 4.30 (m, 2, 3—C$\underline{H}_2$S—), 5.08 (d, 1, C$_6$-$\underline{H}$, J=5 Hz), 5.68 (q, 1, C$_7$-$\underline{H}$, J=5 Hz), 7.50 and 7.62 (each s, 2,4-dichlorophenyl), and 9.00 (m, 2, two —CON$\underline{H}$).

EXAMPLE 18

PREPARATION OF 3-(((1-METHYL-1H-TETRAZOL-5-YL)THIO)ME-THYL)-7-(2-(2-THIENYL)ACETAMIDO)-3-CEPHEM-4-CARBOXYLIC ACID IN 1,2-DICHLOROETHANE 7-(2-(2-Thienyl)acetamido)cephalosporanic acid (0.99 gram; 2.5 mmole) and 1-methyl-1H-tetrazole-5-thiol (0.58 gram; 5 mmole) were added to 12.5 ml. of 1,2-dichloroethane and the reaction mixture was refluxed. The reflux was conducted to permit removal of the acetic acid by-product; this was accomplished by returning the 1,2-dichloroethane reflux through calcium oxide.

After 5 ¾ hours of reflux, the reaction mixture was cooled to room temperature and filtered. The fluffy needles were washed in 10 ml. of 1,2-dichloroethane and dried, 0.77 grams (68.1 percent yield).

Evaporation of the filtrate gave another 0.04 gram of product (about 3.5 percent yield).

The identity of the product was confirmed by TLC and, in the case of the main product, by NMR. The NMR was identical with the NMR on the Example 5 product.

EXAMPLE 19

PREPARATION OF 3-(((5-METHYL-1,3,4-THIADIAZOL-2-YL)THIO)-METHYL)-7-(2-(2-THIENYL)ACETAMIDO)-3-CEPHEM-4-CARBOXYLIC ACID IN ACETONITRILE 7-(2-(2-Thienyl)acetamido)cephalosporanic acid (2.0 grams; 5 mmole) and 5-methyl-1,3,4-thiadiazole-2-thiol (2.64 grams; 20 mmole) in 25 ml. of acetonitrile were refluxed overnight at 79° C. TLC showed only a trace of cephalosporanic acid starting material. The reaction mixture was filtered, to remove an oily residue, and solvent was removed on a rotary evaporator. The residue was crystallized from 1:1 acetonitrile:isopropyl acetate, separated by filtration, washed and vacuum dried, 1.59 gram (33.9 percent yield) m.p. 166° C. The identity of the product was confirmed by IR, UV, NMR, MS, and elemental analyses. NMR (DMSO-$d_6$) δ 2.68 (s, 3, —C$\underline{H}_3$ of tetrazole), 3.68 (s, 2, 2—C$\underline{H}_2$), 3.76 (s, 2, —C$\underline{H}_2$CONH—), 4.38 (q, 2, 3—C$\underline{H}_2$S—, J=13 Hz), 5.10 (d, 1, C$_6$-$\underline{H}$, J=5 Hz), 5.70 (q, 1, C$_7$-$\underline{H}$, J=5 Hz, J=9 Hz), 6.92 (d, 2, thiophene 3- and 4-H), 7.37 (t, 1, thiophene 5-H), and 9.10 (d, 1, —CH$_2$CON$\underline{H}$, J=9 Hz).

EXAMPLE 20

PREPARATION OF 3-(((1-METHYL-1H-TETRAZOL-5-YL)THIO)ME-THYL)-7-(2-(2-THIENYL)ACETAMIDO)-3-CEPHEM-4-CARBOXYLIC ACID IN 1,1,2-TRICHLOROETHANE 7-(2-(2-Thienyl)acetamido)cephalosporanic acid (2.0 grams; 5 mmole) and 1-methyl-1H-tetrazole-5-thiol (1.2 grams; 10 mmole) were added to 25 ml. of 1,1,2-trichloroethane and heated to 100°-101° C. The reaction was followed by TLC; after 4 hours at 100°-101° C., with stirring, TLC showed no cephalosporanic acid starting material remaining. The reaction mixture was cooled to room temperature, with stirring. A seed was introduced and the reaction mixture was allowed to stir overnight. The product crystallized. Solvent was removed by evaporation and 25 ml. of 1,2-dichloroethane added. Solvent was again removed by filtration, and the product was washed and vacuum dried.

There was obtained 0.98 gram of 3-(((1-methyl-1H-tetrazol-5-yl)thio)methyl)-7-(2-(2-thienyl-)acetamido)3-cephem-4-carboxylic acid, m.p. 158° C. (dec) (43.4 percent yield).

EXAMPLE 21
PREPARATION OF 3-(((1-METHYL-1H-TETRAZOL-5-YL)THIO)METHYL)-7-(2-(2-THIENYL)ACETAMIDO)-3-CEPHEM-4-CARBOXYLIC ACID IN (A) METHYL ETHYL KETONE AND (B) 1,1,2-TRICHLOROETHANE (A) 7-(2-(2-Thienyl)acetamido)cephalosporanic acid (2.0 grams; 5 mmole) and 1-methyl-1H-tetrazole-5-thiol (1.2 grams; 10 mmole) were added to 25 ml. of methyl ethyl ketone and refluxed 48 hours. TLC showed that only a trace of cephalosporanic acid starting material remained. The reaction mixture was washed with a mixture of 2.5 grams of sodium bicarbonate in 50 ml. of water. The water layer was treated with 1 gram of carbon and 50 ml. of ethyl acetate was added. The pH was then lowered to pH 1.6 with 4 ml. of methanesulfonic acid in 30 ml. of water. The ethyl acetate layer was dried over sodium sulfate and evaporated to an oil on a rotary evaporator.

The product was crystallized by dropwise addition of 50 ml. of ether. The product was separated by filtration, washed, and vacuum dried, 0.94 gram (41.6 percent yield). The NMR was identical with the NMR of the product of Example 5.

(B) The reaction was repeated with the same starting materials and amounts as in part (A), except that 50 ml. of 1,1,2-trichloroethylene was used as solvent. The reaction mixture was refluxed for 16 hours, at which time TLC showed that no cephalosporanic acid starting material was present. The product was separated as described in part (A), 0.47 gram (20.8 percent yield). The NMR was identical with the NMR of the product of Example 5.

EXAMPLE 22
PREPARATION OF 3-(((1-METHYL-1H-TETRAZOL-5-YL)THIO)METHYL)-7-(2-PHENYLACETAMIDO)-7-METHOXY-3-CEPHEM-4-CARBOXYLIC ACID IN 1,2-DICHLOROETHANE 7-(2-Phenylacetamido)-7-methoxycephalosporanic acid (210 mg.; 0.5 mmole), 1-methyl-1H-tetrazole-5-thiol (87 mg.; 0.75 mmole) and 15 ml. of 1,2-dichloroethane were mixed and refluxed for 6 hours under nitrogen, at which time TLC showed only a trace of cephalosporanic acid starting material. Additional 1-methyl-1H-tetrazole-5-thiol (29 mg.; 0.25 mmole) was added and the reaction mixture refluxed for an additional three hours. TLC showed no appreciable change.

The reaction mixture was washed four times with saturated sodium bicarbonate, and the bicarbonate layer was washed three times with ethyl acetate, an amount of fresh ethyl acetate added, cooled to 0° C. and adjusted to pH 2.2 with 20 percent HCl. The layers were separated, and the aqueous layer washed with ethyl acetate. The acetate layers were combined, washed with saturated NaCl, dried over magnesium sulfate, filtered, and evaporated, leaving a pale green foam as a residue, 199 mg. (83.6 percent yield). The identity of the product was confirmed by TLC and NMR. NMR(CDCl$_3$ + 1d acetone-d$_6$) δ 3.45 (s, 3, —OCH$_3$), 3.55 (s, 2, 2—CH$_2$), 3.75 (s, 2, φCH$_2$CO—), 3.9 (s, 3, CH$_3$ on tetrazole), 4.4 (s, 2, 3—CH$_2$S—), 5.15 (s, 1, C$_6$-H), 7.35 (s, 5, φ), 8.0 (s, 1, —CH$_2$CONH—), and ~11.2 (s, 1, J=0 Hz, -COOH).

EXAMPLE 23
PREPARATION OF 3-(((2-BENZOTHIAZOLYL)THIOMETHYL)-7-(2-(2-THIENYL)ACETAMIDO)-3-CEPHEM-4-CARBOXYLIC ACID IN 1,2-DICHLOROETHANE 7-(2-(2-Thienyl)acetamido)cephalosporanic acid (1.0 gram; 2.5 mmole) and 2-mercaptobenzothiazole (0.625 gram; 3.75 mmole) were placed in a flask, the air displaced with a head of nitrogen, 25 ml. of 1,2-dichloroethane added, and the reaction mixture heated to reflux and refluxed for about 24 hours, with stirring. The reaction mixture was then cooled and filtered, yielding the product as an offwhite material, 1.1 grams (88 percent yield), m.p. 190.5°-191° C. (dec). It was dried overnight at 40° C., under vacuum, and submitted for analyses. The identity of the product was confirmed by NMR, UV Mass spectroscopy, IR, and elemental analysis. NMR(DMSO-d$_6$) δ 3.74 (s, 2, 2—CH$_2$), 3.80 (s, 2, —CH$_2$CONH—), 4.58 (q, 2, 3—CH$_2$S—, J=13 Hz), 5.14 (d, 1, C$_6$-H, J=5 Hz), 5.73 (q, 1, C$_7$-H, J=5 Hz, J=8 Hz), 6.96, 7.43, and 7.96 (each m, phenyl and thienyl rings), 9.10 (d, 1, —CH$_2$CONH—, J=8 Hz).

EXAMPLE 24
PREPARATION OF 3-(((5-(N-METHYLACETAMIDO) 1,3,4-THIADIAZOL-2-YL)THIO)METHYL)-7-(2-(2-THIENYL)ACETAMIDO)-3-CEPHEM-4-CARBOXYLIC ACID IN 1,2-DICHLOROETHANE 7-(2-(2-Thienylacetamido)cephalosporanic acid (2.0 grams; 5 mmole) and 5-(N-methylacetamido)-1,3,4-thiadiazole-2-thiol (1.42 grams; 7.5 mmole) were added to 50 ml. of 1,2-dichloroethane and the reaction mixture refluxed for 10 hours. The reaction mixture was cooled, filtered, washed with 1,2-dichloroethane, and vacuum dried, 2.06 grams (78.3 percent), m.p. 178°-179° C. The identity of the product was confirmed by IR, UV, NMR, mass spectroscopy, and elemental analysis. NMR(DMSO-d$_6$) δ 2.42 (s, 3, —COCH$_3$), 3.74 (m, 7, 2—CH$_2$, —CH$_3$ of tetrazole, and —CH$_2$CONH—), 4.35 (q, 2, 3—CH$_2$, J=13 Hz), 5.10 (d, 1, C$_6$-H, J=5 Hz), 5.70 (q, 1, C$_7$-H, J=5 Hz, J=9 Hz), 6.96 and 7.36 (each m, 3, thiophene H), and 9.10 (d, 1, —CH$_2$CONH—, J=9 Hz).

EXAMPLE 25
PREPARATION OF 3-(((1-METHYL-1H-TETRAZOL-5-YL)THIO)METHYL)-7-(N-tert-BUTOXYCARBONYL)-2-PHENYLGLYCYLAMIDO)-3-CEPHEM-4-CARBOXYLIC ACID IN 1,2-DICHLOROETHANE 1,2-Dichloroethane (45 ml.) was refluxed to remove water-solvent azeotropes, then distilled down to 30 ml., which was permitted to cool. 7(N-tert-Butoxycarbonyl-2-phenylglycylamido)cephalosporanic acid (253 mg.; 0.5 mmole) was added and the solution distilled further, down to 15 ml. and again cooled. 1-Methyl-1H-tetrazole-5-thiol (87 mg.; 0.75 mmole) was added and the reaction mixture refluxed under nitrogen and monitored by TLC. At 16 hours, TLC showed only a trace of starting material.

The reaction mixture was washed four times with saturated sodium bicarbonate and the bicarbonate layers combined and washed twice with ethyl acetate. To the washed bicarbonate layers, fresh ethyl acetate was added, and the solution was cooled to 0° C. and adjusted to pH 2.4 with 20 percent HCl. The layers were separated. The aqueous layer was washed with ethyl acetate.

The ethyl acetate layers were combined, washed with saturated NaCl, dried over magnesium sulfate, filtered and evaporated, yielding a white foam, 224 mg. (80 percent yield). The identity of the product was confirmed by TLC and NMR. NMR showed a small amount (≦0.10 percent) of the cephalosporanic acid starting material.

The product was suspended in 10 ml. of diethyl ether and triturated for 1 hours. The ether was decanted, and 10 ml. of fresh diethyl ether added and triturated for 1 hour. The ether was decanted and evaporated to dryness, yielding the product as a white powder. The identity of the product was confirmed by TLC and NMR. NMR (CDCl₃) δ 1.45 (s, 9, —COO tert C₄H₉), 3.6 (s, 2, 2—CH₂), 3.95 (s, 3, CH₃ on tetrazole), 4.3 (s, 2, 3—CH₂S—), 4.9 (d, 1, J=6 Hz, C₆-H), 5.4 (d, 1, J=8 Hz,

5.75 (q, 1, J=4 Hz, C₇-H), 6.2 (d, 1, J=8 Hz,

7.4 (s, 5, φ), 7.65 (d, 1, J=8 Hz, —CONH), and ~ 9.3 (s, 1, COOH).

EXAMPLE 26
PREPARATION OF 3-(((1-METHYL-1H-TETRAZOL-5-YL)THIO)METHYL)-7-(N-(tert-BUTOXYCARBONYL)-2-(p-HYDROXYPHENYL)GLYCYLAMIDO)-3-CEPHEM-4-CARBOXYLIC ACID IN 1,2-DICHLOROETHANE 1,2-Dichloroethane (45 ml.) was refluxed with a trap and 15 ml. solvent removed. The remaining 30 ml. was cooled. 7-(N-(tert-Butoxycarbonyl)-2-(p-hydroxyphenyl)glycylamido)cephalosporanic acid (260.5 mg.; 0.5 mmole) was added and the solution distilled further, down to 15 ml. and cooled again 1-methyl-1H-tetrazole-5-thiol (87 mg.; 0.75 mmole) was added and the reaction mixture heated to 65°–70° C. and followed by TLC. TLC showed almost no starting material after 3 hours, and the reaction mixture was worked up at the end of 4 hours.

The workup and purification was essentially the same as described in the preceding example. The yield was 189 mg. of crude product (65.5 percent) and 46 mg. of purified product (about 16 percent). NMR(CDCl₃ + 2d acetone d₆) δ 1.45 (s, 9, —COO tert C₄H₉), 3.35 (s, 2, 2—CH₂), 3.85 (s, 3, CH₃ on tetrazole), 4.31 (s, 2, 3—CH₂S—), 4.9 (d, 1, J=6 Hz, C₆-H), 5.3 (q, 1, J=3 Hz, C₇-H), 5.4 (s, 1,

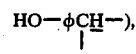

5.75 (d, 1, J=6 Hz,

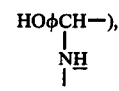

6.4 (s, 1, COOH), 6.8 (d, 2, J=8 Hz,

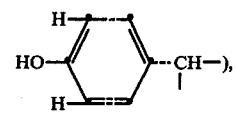

and 7.9 (d, 1, —CONH).

EXAMPLE 27
PREPARATION OF 3-(((1-METHYL-1H-TETRAZOL-5-YL)THIO)METHYL-7-(2-PHENOXYACETAMIDO)-3-CEPHAM-4-CARBOXYLIC ACID IN 1,2-DICHLOROETHANE 1,2-Dichloroethane (60 ml.) was refluxed with a trap and 15 ml. of solvent removed, leaving 45 ml., which was cooled. 7-(2-Phenoxyacetamido)cephalosporanic acid (406 mg.; 1 mmole) was added and the solution distilled further, down to 30 ml. and cooled again. 1-Methyl-1H-tetrazole-5-thiol (174 mg.; 1.5 mmole) was added and the reaction mixture was refluxed under nitrogen for 12 hours, at which time TLC in 10:3 diethyl ether/(3:1 acetic acid/water) showed product, excess thiol reactant, a little cephalosporanic acid reactant, and an unknown.

The reaction mixture was then worked up in essentially the same procedures reported in the preceding two examples. TLC of the final product showed it to be identical with an authentic sample of product prepared by prior art methods. NMR (CDCl₃) δ 3.65 (s, 2, 2—CH₂), 3.9 (s, 3, CH₃ of tetrazole), 4.35 (s, 2, 3—CH₂S—), 4.65 (s, 2, φOCH₂—), 5.1 (d, 1, J=4 Hz, C₆-H), 5.9 (q, 1, J=4 Hz, C₇-H), 7.1 (m, 5, φ-), 7.6 (d, 1, J=10 Hz, —CONH—), and ~ 9 (s, 1, —COOH).

EXAMPLE 28-31
PREPARATION OF 3-(((1-METHYL-1H-TETRAZOL-5-YL)THIO)METHYL)-7-(2-(2-THIENYL)ACETAMIDO)-3-CEPHEM-4-CARBOXYLIC ACID IN FLUOROBENZENE 3-(((1-Methyl-1H-tetrazol-5-yl)thio)methyl)-7-(2-(2-thienyl)acetamido)-3-cephem-4-carboxylic acid was prepared in four different reactions, each utilizing a different cephalosporanic acid starting material, as follows:

28: 3-(propionyloxymethyl)-7-(2-(2-thienyl)acetamido)-3-cephem-4-carboxylic acid (41 mg.; 0.1 mmole)

29: 3-(2-methylpropionyloxymethyl)-7-(2-(2-thienyl)acetamido)-3-cephem-4-carboxylic acid (42 mg.; 0.1 mmole)

30: 3-(n-butyryloxymethyl)-7-(2-(2-thienyl)acetamido)-3-cephem-4-carboxylic acid (42 ml.; 0.1 mmole)

31: 3-(cyclobutylcarbonyloxymethyl)-7-(2-(2-thienyl)acetamido)-3-cephem-4-carboxylic acid (43 mg.; 0.1 mmole)

In each instance the compound was suspended in 10 ml. of fluorobenzene (which had been dried over an aluminosilicate desiccant sold under the term 4-A Linde Molecular sieve). 1-Methyl-1H-tetrazole-5-thiol (in each reaction 18 mg.; 0.15 mmole) was added and the reaction mixture was refluxed for about 24 hours. In each reaction the product precipitated and was separated by filtration and dried. TLC of the product in ethyl acetate/acetic acid showed that each displacement had been quantitative. The NMR of each product was consistent with that of an authentic sample of the product prepared by aqueous displacement.

EXAMPLE 32

PREPARATION OF 3-(((3-METHYL-1,2,4-OXADIAZOL-5-YL)THIO)-METHYL)-7-(2-(2-THIENYL)ACETAMIDO)-3-CEPHEM-4-CARBOXYLIC ACID IN 1,1,2-TRICHLOROETHANE 7-(2-(2-Thienyl)acetamido)cephalosporanic acid (396 mg.; 1 mmole) was suspended in 40 ml. of 1,1,2-trichloroethane and 3-methyl-1,2,4-oxadiazole-5-thiol (116 mg.; 1 mmole) added. The reaction mixture was heated to 113° C. in an oil bath for about 3 hours, then allowed to cool overnight and evaporated to an oil. Ethyl acetate and saturated sodium bicarbonate were added. The ethyl acetate portion was rinsed again with saturated sodium bicarbonate, and the aqueous portions were combined and extracted again with ethyl acetate. The aqueous portion was layered with fresh ethyl acetate, cooled in an ice bath, and the pH adjusted to 2.5 with 20 percent HCl. The layers were separated and the aqueous layer extracted again. The ethyl acetate layer was washed, combined with saturated sodium chloride, dried over magnesium sulfate, filtered, and evaporated. 1,1,2-trichloroethane was added to the residue, whereupon the product formed a solid, 220 mg. (48 percent yield). Identity of the product was confirmed by NMR, IR, UV, and bioautogram. (NMR (DMSO-d$_6$) δ 2.35 (s, 3, C$\underline{H}_3$ on oxadiazole), 3.7 (q, 2, $\underline{J}$=18 Hz, 2—C$\underline{H}_2$), 3.8 (s, 2, —C$\underline{H}_2$CONH—), 4.4 (q, 2, $\underline{J}$=14 Hz, 3—C$\underline{H}_2$S—), 5.1 (d, 1, $\underline{J}$=5 Hz, C$_6$-$\underline{H}$), 5.6 (q, 1, $\underline{J}$=4 Hz, C$_7$-$\underline{H}$), 6.9, 7.3 (t, d, 3, thiophene $\underline{H}$), and 9.1 (d, 1, $\underline{J}$=8 Hz, —CH$_2$CON$\underline{H}$—).

EXAMPLE 33

PREPARATION OF 3-(((1H-1,3,4-TRIAZOL-5-YL)-THIO)METHYL)-7-(2-(2-THIENYL)ACETAMIDO)-3-CEPHEM-4-CARBOXYLIC ACID IN 1,1,2-TRICHLOROETHANE 7-(2-(2-Thienyl)acetamido)cephalosporanic acid (396 mg.; 1 mmole) was suspended in 30 ml. of 1,1,2-trichloroethane and 1H-1,3,4-triazole-5-thiol (100 mg.; about 1 mmole) added. The reaction mixture was heated to 105° C. Within 30 minutes, product was precipitating. Heating to about 100° C. was continued for about 6 hours, at which time the reaction mixture was cooled to room temperature. Product was collected by filtration and rinsed with 1,1,2-trichloroethane 380 mg. (87 percent yield). The identity of the product was confirmed by IR, NMR, UV, and bioautogram. Bioautogram also showed the presence of the cephalosporanic acid starting material, which high pressure liquid chromatography showed to be present in the amount of 6.8 percent. NMR (DMSO-d$_6$) δ 3.7 (s, 2, 2—C$\underline{H}_2$), 3.8 (s, 2, —C$\underline{H}_2$CONH—), 4.2 (q, 2, $\underline{J}$=5 Hz, 3—C$\underline{H}_2$S—), 5.1 (d, 1, $\underline{J}$=5 Hz, C$_6$-$\underline{H}$), 5.7 (q, 1, $\underline{J}$=4 Hz, C$_7$-$\underline{H}$), 7.0, 7.4 (t, d, 3, thiophene $\underline{H}$), 8.45 (s, 3, triazole >N$\underline{H}$), and 9.13 (d, 1, $\underline{J}$=8 Hz, —CH$_2$CON$\underline{H}$—).

EXAMPLE 34

PREPARATION OF 3-(((1-METHYL-1H-TETRAZOL-5-YL)THIO)ME-THYL)-7-(2-PHENYLACETAMIDO)-3-CEPHEM-4-CARBOXYLIC ACID IN CHLOROFORM 7-(2-Phenylacetamido)cephalosporanic acid (195 mg.; 0.5 mmole) was suspended in 75 ml. of chloroform and 1-methyl-1H-tetrazole-5-thiol (75 mg.; 0.65 mmole) added. The reaction mixture was heated in an oil bath at 80°–85° C. for about 3 hours and 60 ml. distilled off. TLC showed very little product, whereupon 20 ml. of 1,2-dichloroethane was added and heating continued overnight. TLC of the reaction mixture the following morning showed little cephalosporanic acid starting material. After a total reaction time of about 26 hours, the reaction mixture was cooled to room temperature. The product was worked up in essentially the same procedures as reported in Example 32, yielding 80 mg. of purified material (35 percent yield). Identity of the product was confirmed by NMR, IR, UV, and bioautogram. NMR (DMSO-d$_6$) δ 3.6 (s, 2, 2—C$\underline{H}_2$), 3.7 (s, 2, —C$\underline{H}_2$CONH—), 4.0 (s, 3, C$\underline{H}_3$ on tetrazole), 4.3 (s, 2, 3—C$\underline{H}_2$S—), 5.1 (d, 1, $\underline{J}$=5 Hz, C$_6$-$\underline{H}$), 5.7 (q, 1, $\underline{J}$=4 Hz, C$_7$-$\underline{H}$), 7.3 (s, 5, φ), and 9.13 (s, 1, $\underline{J}$=8 Hz, —CH$_2$CON$\underline{H}$—).

EXAMPLE 35

PREPARATION OF 3-(((1-METHYL-1H-TETRAZOL-5-YL)THIO)ME-THYL)-7-ACETAMIDO-3-CEPHEM-4-CARBOXYLIC ACID IN 1,2-DICHLOROETHANE

7-Acetamidocephalosporanic acid (314 mg.; 1 mmole) and 1-methyl-1H-tetrazole-5-thiol (98 mg.; 0.65 mmole) were mixed in 70 ml. of 1,2-dichloroethane; 50 ml. were distilled off and the reaction mixture than refluxed for about 24 hours.

The reaction mixture was worked up in essentially the procedures reported in Example 32 yielding 120 mg. of product (yield, 32 percent). Identity of the product was confirmed by NMR, IR, UV, and bioautogram. NMR (DMSO-d$_6$) δ 1.97 (s, 3, C$\underline{H}_3$CONH—), 3.7 (s, 2, 2—C$\underline{H}_2$), 4.0 (s, 3, C$\underline{H}_3$ on tetrazole), 4.35 (s, 2, 3—C$\underline{H}_2$S—), 5.1 (d, 1, $\underline{J}$=5 Hz, C$_6\underline{H}$), 5.7 (q, 1, $\underline{J}$=4 Hz, C$_7$-$\underline{H}$, and 8.8 (d, 1, $\underline{J}$=8 Hz, —CH$_2$CON$\underline{H}$).

EXAMPLE 36

PREPARATION OF 3-(((3-METHYL-1,2,4-THIADIAZOL-5-YL)THIO)-METHYL)-7-(2-(2-THIENYL)ACETAMIDO)-3-CEPHEM-4-CARBOXYLIC ACID IN 1,2-DICHLOROETHANE 7-(2-(2-Thienyl)acetamido)cephalosporanic acid (200 mg.; 0.5 mmole) and 3-methyl-1,2,4-thiadiazole-5-thiol (85 mg.; 0.65 mmole) were mixed in 50 ml. of 1,2-dichloroethane and heated to 95° C. on an oil bath. The bath temperature was maintained at about 90° C. for about 19 hours. The reaction mixture was then removed from the bath and allowed to cool and refrigerated for a day. Three volumes of ethyl acetate were then added and washed with two 50 ml. portions of saturated sodium bicarbonate. The combined aqueous portions were extracted with ethyl acetate, layered with fresh ethyl acetate, and cooled in an ice bath. The pH was adjusted to 2.0. The layers were separated and the aqueous layer extracted again with ethyl acetate. The combined ethyl acetate portions were washed with saturated sodium chloride, dried over magnesium, sulfate, filtered, and evaporated, yielding 252 mg. of a foam. It crystallized from acetone/diethyl ether, 153 mg. (65 percent yield). Identity of the product was confirmed by NMR, UV, IR, and bioautogram. NMR (DMSO-$d_6$) δ 3.7 (s, 2, 2—C$\underline{H}_2$), 3.8 (s, 2, —C$\underline{H}_2$CONH), 4.5 (q, 2, $\underline{J}$=15 Hz, 3—C$\underline{H}_2$S—), 5.1 (d, 1, $\underline{J}$=5 Hz, C$_6$-$\underline{H}$), 5.7 (q, 1, $\underline{J}$=4 Hz, C$_7$-$\underline{H}$), 6.96, 7.38 (t, d, 3, thiophene $\underline{H}$), and 9.13 (d, 1, $\underline{J}$=8 Hz, —CH$_2$CON$\underline{H}$).

EXAMPLE 37

PREPARATION OF 3-(((2-PYRIMIDINYL)THIO)METHYL)-7-(2-(2-THIENYL)ACETAMIDO)-3-CEPHEM-4-CARBOXYLIC ACID IN ACETONITRILE 7-(2-(2-Thienyl)acetamido)cephalosporanic acid (2.0 grams; 5 mmole) and 2-mercaptopyrimidine (0.62 grams; 5.5 mmole) were mixed in 25 ml. of dry acetonitrile and the mixture refluxed overnight (about 16 hours) with stirring. TLC showed complete conversion to product. The reaction mixture was cooled to room temperature and the product separated by filtration. It was then washed with about 50 ml. of acetonitrile and vacuum dried at 50° C. for 4 hours, 1.86 grams of off-white crystals (83.0 percent yield), m.p. 217° C. (dec). NMR in DMSO-$d_6$ showed neither starting material. The identity of the product was confirmed by IR, UV, and NMR. NMR (DMSO$_6$-$d_6$) δ 3.55 (q, 2, 2-C$\underline{H}_2$, $\underline{J}$=18 Hz), 3.74 (s, 2, —C$\underline{H}_2$CONH), 4.28 (q, 2, 3—C$\underline{H}_2$ S—, $\underline{J}$=13 Hz), 5.00 (d, 1, C$_6$-$\underline{H}$, $\underline{J}$=5 Hz), 5.64 (q, 1, C$_7$-$\underline{H}$, $\underline{J}$=5 Hz, $\underline{J}$=9 Hz), 7.08 (m) and 8.52 (d) (6, thiophene and pyrimidine $\underline{H}$), and 9.00 (d, 1, —CH$_2$CON$\underline{H}$—, $\underline{J}$=9 Hz).

EXAMPLE 38

PREPARATION OF 3-(((2-PYRIMIDINYL)THIO)METHYL)-7-(2-(2-THIENYL)ACETAMIDO)-3-CEPHEM-4-CARBOXYLIC ACID IN ACETIC ACID 7-(2-(2-Thienyl)acetamido)cephalosporanic acid (2.0 grams; 5 mmole), 2-mercaptopyrimidine (0.6 gram; 5.4 mmole), and sodium acetate (0.41 gram; 5 mmole) in 25 ml. of glacial acetic acid were heated to 85° C. for 4 hours. Product crystallized during the course of reaction. The reaction mixture was then cooled to room temperature and the product separated by filtration, washed in acetic acid, and dried, 1.58 grams (70.5 percent yield) of white crystals, m.p. 218° C. (dec.). Identity of the product was confirmed by IR, UV, NMR, and elemental analysis. The NMR was identical with the NMR of the product of Example 37.

EXAMPLE 39

PREPARATION OF 3-(((1-METHYL-1H-TETRAZOL-5-YL)THIO)METHYL)-7-(2-(2-THIENYL)ACETAMIDO)CEPHALOSPORANIC ACID IN ACETIC ACID 7-(2-(2-Thienyl)acetamido)cephalosporanic acid (2.0 grams; 5 mmole), 1-methyl-1H-tetrazole-5-thiol (0.81 gram; 7 mmole), and sodium acetate (0.41 gram; 5 mmole) in 25 ml. of glacial acetic acid were heated to 75°–77° C. and held there over 8 hours. TLC was run every hour and at eight hours, TLC showed that the reaction was complete. The reaction mixture was cooled to 40°–45° C. and the acetic acid removed under vacuum. To the residue was then added 50 ml. of ethyl acetate and 50 ml. of water. The aqueous layer was acidified to pH 1.5 with 1N H$_2$SO$_4$. The ethyl acetate layer was separated, dried over anhydrous sodium sulfate, and the ethyl acetate removed on a rotary evaporator. The residue, a light weight oil, was redissolved in 50 ml. of ethanol and a solution of 2 ml. of dicyclohexylamine (10.2 mmole) in 10 ml. of ethanol was added. The product precipitated almost immediately as the dicyclohexylamine salt but was stirred an additional 15 minutes; it was then separated by filtration, washed with ethanol and dried, 1.2 grams (37.8 percent yield), m.p. 185°–186° C. IR, NMR, and UV were identical with previously prepared samples of the same product.

EXAMPLE 40

PREPARATION OF 3-(((1-BENZYL-1H-TETRAZOL-5-YL)THIO)METHYL)-7-(2-(2-(THIENYL)ACETAMIDO)-3-CEPHEM-4-CARBOXYLIC ACID IN 1,2-DICHLOROETHANE 7-(2-(2-Thienyl)acetamido)cephalosporanic acid (2.0 grams; 5 mmole) and 1-benzyl-1H-tetrazole-5-thiol (1.44 grams; 7.5 mmole) were added to 25 ml. of 1,2-dichloroethane and the reaction mixture heated to 85° C. in an oil bath and maintained at that temperature overnight, with stirring. TLC showed no cephalosporanic acid starting material. Solvent was removed on a rotary evaporator, leaving a foam. To the foam, 25 ml. of methanol was added and the mixture warmed on a steam bath until the sample dissolved. Solvent was evaporated on a rotary evaporator and the product crystallized. It was stirred for 15 minutes, then separated by filtration, washed with methanol, and vacuum dried, 1.6 grams (60.6 percent yield), m.p. 171°–171.5° C.

EXAMPLE 41

PREPARATION OF 3-AMIDINOTHIOMETHYL-7-(2-(2-THIENYL)ACETAMIDO)-3-CEPHEM-4-CARBOXYLIC ACID IN ACETONITRILE 7-(2-(2-Thienyl)acetamido)cephalosporanic acid (3.12 grams; 8 mmole) and thiourea (912 mg.; 12 mmole) in 15 ml. of acetonitrile (which had been dried over an aluminosilicate desiccant sold under the term 4-A Linde molecular sieve) were heated at 87° C. with stirring for 24 hours. Within one hour, precipitate began forming in the reaction mixture.

At the end of 24 hours, the product was separated by filtration of the hot reaction mixture, and dried, 2.5 grams (76 percent yield). Elemental analysis showed Theory: C, 43.68; H, 3.91; N, 13.58.

Found: C, 43.50; H, 4.03; N, 13.29.

NMR confirmed the identity of the product.

EXAMPLE 42

PREPARATION OF 3-BENZOYLTHIOMETHYL-7-(2-(2-THIENYL)ACETAMIDO)-3-CEPHEM-4-CARBOXYLIC ACID IN ISOPROPYL ACETATE 7-(2-(2-Thienyl)acetamido)cephalosporanic acid (1.0 gram; 2.5 mmole) and thiobenzoic acid (510 mg.; 3.7 mmole) were suspended in 20 ml. of anhydrous isopropyl acetate and the suspension heated under reflux for 31 hours, by which time all reactants were in solution. Solvent was evaporated under vacuum, leaving a residue which TLC indicated was a 60-40 mixture of product and unreacted starting material.

Preparative thick-layer chromatography over silica plates using acetone: acetic acid (16:1) as eluent afforded a purified sample of product. NMR (DMSO-$d_6$/$D_2O$) $\delta$ 3.50 (ABq, 2H, 2—C$\underline{H}_2$, $\underline{J}$=6 Hz, $\underline{J}$=19 Hz), 3.82 (s, 2H, —C$\underline{H}_2$CONH—), 4.20 (d, 2H, 3—CH$_2$S—, $\underline{J}$=5 Hz), 5.03 (d, 1H, C$_6$-$\underline{H}$, $\underline{J}$=5 Hz), 5.69 (d, 1H, C$_7$-$\underline{H}$, $\underline{J}$=5 Hz), 6.89-8.0 (m, 8H, aromatic $\underline{H}$).

EXAMPLE 43

PREPARATION OF 3-((PHENYLTHIO)METHYL)-7-(2-(2-THIENYL)ACETAMIDO)-3-CEPHEM-4-CARBOXYLIC ACID IN 1,2-DICHLOROETHANE 7-(2-(2-Thienyl)acetamido)cephalosporanic acid (2.0 grams; 5 mmole) and benzenethiol (0.75 ml.; 7.5 mmole) were added to 25 ml. of 1,2-dichloroethane. The reaction mixture was refluxed overnight; TLC showed no cephalosporanic acid starting material remaining.

Solvent was evaporated on a rotary evaporator and 25 ml. of ethanol added to the residue and heated to get the residue into partial solution. To get the remainder into solution, 25 ml. of methanol was added and heated. The resulting solution was filtered through cotton, treated with 2.0 grams of carbon, stirred 5 minutes, and filtered through Hyflo brand of filter aid. Solvent was removed on a rotary evaporator. NMR of the residue showed some thiol starting material present.

The residue was slurried in 25 ml. of isopropyl acetate, filtered, and refrigerated overnight. The filtrate was then diluted with 25 ml. of ethyl acetate and washed with 25 ml. of dilute sodium bicarbonate to remove thiol. The ethyl acetate layer was added to 25 ml. of water and the pH at 8.5 was adjusted to pH 1.4 with $H_2SO_4$. The ethyl acetate layer was then dried over magnesium sulfate, filtered, and evaporated to a foam on a rotary evaporator, 0.92 gram (19.4 percent yield). NMR (DMSO-$d_6$) $\delta$ 3.58 (m, 2, 2—C$\underline{H}_2$), 3.75 (s, 2, —CH$_2$CONH—), 4.12 (q, 2, 3—C$\underline{H}_2$S—, $\underline{J}$=13 Hz), 5.08 (d, 1, C$_6$-$\underline{H}$, J=5 Hz), 5.66 (q, 1, C$_7$-$\underline{H}$, $\underline{J}$=5 Hz, $\underline{J}$=9 Hz), 7.15 (m, 8, thiophene $\underline{H}$ and phenyl $\underline{H}$), and 9.10 (d, 1, —CH$_2$CON$\underline{H}$—, $\underline{J}$=9 Hz).

EXAMPLE 44

PREPARATION OF 3-(((5-METHYL-1,3,4-THIADIAZOL-2-YL)THIO)METHYL)-7-(PHENYLACETAMIDO)-3-CEPHEM-4-CARBOXYLIC ACID IN 1,2-DICHLOROETHANE 7-(2-Phenylacetamido)cephalosporanic acid (1.95 grams; 5 mmole) and 5-methyl-1,3,4-thiadiazole-2-thiol (0.99 gram; 7.5 mmole) in 25 ml. of 1,2-dichloroethane were refluxed for 16 hours. TLC showed a trace of cephalosporanic acid starting material. Product crystallized during the reaction.

The reaction mixture was cooled to 0°-5° C. and filtered, and the product washed with cold 1,2-dichloroethane and vacuum dried, 1.82 grams (78.8 percent yield), m.p. 171°-172° C. NMR (DMSO-$d_6$) $\delta$ 2.70 (s, 3, —CH$_3$ of thiadiazolyl), 3.58 (s, 2, —C$\underline{H}_2$CONH—), 3.70 (broad s, 2, 2—C$\underline{H}_2$), 4.40 (q, 2, 3—C$\underline{H}_2$S—, $\underline{J}$=13 Hz), 5.12 (d, 1, C$_6$-$\underline{H}$, $\underline{J}$=5 Hz), 5.72 (q, 1, C$_7$-$\underline{H}$, $\underline{J}$=5 Hz, J=9 Hz), 7.28 (s, 5, phenyl $\underline{H}$), and 9.08 (d, 1, —CH$_2$CON$\underline{H}$—, $\underline{J}$=9 Hz).

EXAMPLE 45

PREPARATION OF 3-(METHYLTHIO)METHYL)-7-(2-(2-THIENYL)ACETAMIDO)-3-CEPHEM-4-CARBOXYLIC ACID IN METHYLENE CHLORIDE 7-(2-(2-Thienyl)acetamido)cephalosporanic acid (24 grams; 60 mmole), 7.0 ml. of methanethiol, and 600 ml. of methylene chloride were stirred and heated in a bomb for 18 hours at 84°-86° C. The reaction mixture was then cooled to room temperature and subjected to TLC. A small amount of insoluble material was filtered off and the filtrate was evaporated. The residue was taken up in ethyl acetate and filtered. The filtrate was layered with about 150 ml. of water and stirred; 1N NaOH was added dropwise to a pH 5.5. The aqueous phase was separated and concentrated to a volume of about 75 ml., then diluted to 700 ml. with water, and glacial acetic acid added to pH 3.8. An amorphous solid precipitated and was stirred for 3 hours on an ice bath, then refrigerated overnight.

The solid was then filtered. The filtrate was layered with 100 ml. of ethyl acetate and the pH adjusted to 2.0 with concentrated HCl. The organic phase was separated and extracted with one-100 ml. portion and one-150 ml. portion of ethyl acetate. The combined organic phases were dried over magnesium sulfate, then stripped of solvent, yielding an amber colored foam. It was dissolved in 50 ml. of ethyl acetate, seeded with the intended product, and held in a refrigerator overnight. Crystals had formed; they were separated by filtration, rinsed with cold isopropyl acetate, and vacuum dried at about 50° C., 3.2 grams (14 percent yield). NMR confirmed the identity of the product, $\delta$ 2.00 (s, 3, 3—CH$_2$SC$\underline{H}_3$), 3.74 (m, 3—C$\underline{H}_2$S-, 2—CH$_2$, and —CH$_2$CONH—), 5.14 (d, 1, C$_6$-$\underline{H}$, $\underline{J}$=5 Hz), 6.64 (q, 1, C$_7$=$\underline{H}$, $\underline{J}$=5 Hz, $\underline{J}$=9 Hz), 7.15 1 (m, 3, thiophene $\underline{H}$), and 9.12 (d, 1, —CH$_2$CON$\underline{H}$—, $\underline{J}$=9 Hz).

EXAMPLE 46

PREPARATION OF 7-(2-FORMYLOXY-2-PHENYLACETAMIDO)-3-(1-METHYL-1H-TETRAZOL-5-YL)THIO)METHYL)-3-CEPHEM-4-CARBOXYLIC ACID SODIUM SALT IN BENZENE 7-(2-Formyloxy-2-phenylacetamido)cephalosporanic acid (2.17 grams; 4.65 mmoles) and 1-methyl-1H-tetrazole-5-thiol (0.87 gram; 7.5 mmole) in 25 ml. of benzene were refluxed (about 80° C.) for 12 hours. A layer of soft plastic deposited on the glass vessel during the reaction. On cooling, the plastic hardened to a glassy solid. TLC showed that the solution contained only a trace of product and that the plastic was mostly product with some deformylated product. The reaction mixture was evaporated with added acetone to a foam which was dissolved in 35 ml. of dry acetone and treated with 10 ml. of a solution of 1.25 grams of sodium 2-ethylhexanoate (7.5 mmole) in acetone. The product crystallized as the sodium salt. After hour, the product was filtered, washed with 20 ml. of acetone and dried, 1.38 grams (58 percent yield). The identity of the product was confirmed by TLC and NMR. NMR (D$_2$O) δ 3.48 (q, 2, 2—C$\underline{H}_2$, J=18 Hz), 4.00 (s, 3, —C$\underline{H}_3$ of tetrazolyl), 4.10 (m, 2, 3—C$\underline{H}_2$S-), 5.05 (d, 1, C$_6$-$\underline{H}$, J=5 Hz), 5.70 (d, 1, C$_7$-$\underline{H}$, J=5 Hz), 6.24 (s, 1,

7.50 (m, 5, phenyl $\underline{H}$), and 8.33 (s, 1,

EXAMPLE 47
PREPARATION OF 7-(2-FORMYLOXY-2-PHENYLACETAMIDO)-3-(((1-METHYL-1H-TETRAZOL-1-YL)THIO)METHYL)-3-CEPHEM-4-CARBOXYLIC ACID IN CARBON TETRACHLORIDE 7-(2-Formyloxy-2-phenylacetamido)cephalosporanic acid (2.17 grams; 4.65 mmole) and 1-methyl-1H-tetrazole-5-thiol (0.87 gram; 7.5 mmoles) in 25 ml. of carbon tetrachloride were refluxed (about 77° C.) for 12 hours. The reaction mixture was then cooled to room temperature and the supernatant decanted from a hardened semi-solid. To the solid was added 25 ml. of 1,2-dichloroethane, with warming. The product crystallized. The mixture was cooled to room temperature and stirred for about an hour, then the product was separated by filtration, washed with 10 ml. of 1,2-dichloroethane, and vacuum dried overnight at 45° C., 1.54 grams of white crystals (65 percent yield). Identity of the product was confirmed by NMR and TLC, the latter of which showed a small trace of deformylated product. The NMR was identical with the NMR of the product of Example 16.

EXAMPLE 48
PREPARATION OF 3-METHYL-1,2,4-OXADIAZOLE-5-THIOL

Acetamide oxime (30 grams; 0.4 mole), carbon disulfide (100 ml.; 1.66 mole) and triethylamine (56 ml.; 0.4 mole) were mixed and stirred in 1 liter of pyridine. A stream of nitrogen gas was bubbled through a carbon disulfide solution and then passed over the reaction mixture. The mixture was heated in an oil bath at 70° C. for three days, then evaporated to an oil, to which ethyl acetate and saturated sodium carbonate were added. The layers were separated and the organic layer was again washed with saturated sodium bicarbonate. The combined sodium bicarbonate washes were extracted with ethyl acetate and the ethyl acetate extracts were discarded. The aqueous portion was layered with fresh ethyl acetate and cooled in an ice bath. The pH was adjusted to 2.5 with 20 percent HCl and sodium chloride was added to saturate the solution. It was then extracted with ethyl acetate, rinsed with saturated sodium chloride solution, and dried over anhydrous magnesium sulfate. The solution was filtered and evaporated to one-half its original volume. An equal volume of carbon tetrachloride was added and evaporation was continued until the product crystallized, 24.8 grams (52 percent yield).

EXAMPLE 49
PREPARATION OF 3-(((3-METHYL-1,2,4-OXADIAZOL-5-YL)THIO)METHYL)-7-(2-(2-THIENYL)ACETAMIDO)-3-CEPHEM-4-CARBOXYLIC ACID IN 1,2-DICHLOROETHANE 7-(2-(2-Thienyl)acetamido)-3-(carbamoyloxymethyl)-3-cephem-4-carboxylic acid (100 mg.; 0.25 mmole) was suspended in 25 ml. of 1,2-dichloroethane and stirred while 3-methyl-1,2,4-oxadiazole-5-thiol (35 mg.; 0.30 mmole) was added. The reaction mixture was heated on an oil bath at 110° C., to distill off 5 ml. of solvent including any trace amount of water. The oil bath temperature was lowered to 90°-95° C. and the reaction mixture maintained for 19 hours, then cooled to room temperature. Insoluble material was removed by filtration and rinsed with 1,2-dichloroethane and diethyl ether. It was determined by TLC to be unreacted starting material with only a trace amount of product.

The filtrate was evaporated and the residual oil partitioned between sodium bicarbonate solution and ethyl acetate. The aqueous solution was layered with fresh ethyl acetate, cooled in an ice bath, and the pH adjusted to 2.5 with 20 percent HCl. The organic layer was removed. The aqueous layer was extracted with fresh ethyl acetate and the combined ethyl acetate solutions were washed with saturated NaCl solution, dried over magnesium sulfate, filtered, and evaporated to an oil. Crystallization from a 1:1 solution containing hexane and diethyl ether gave 13 mg. of product, (11.5 percent yield). The identity of the product was confirmed by NMR and IR, which were identical with the same compound prepared as reported in Example 32.

EXAMPLE 50
PREPARATION OF 3-(((1-METHYL-1H-TETRAZOL-5-YL)THIO)METHYL)-7-(2-(tert-BUTOXYCARBONYL)-2-PHENYLACETAMIDO)-3-CEPHEM-4-CARBOXYLIC ACID IN NITROMETHANE 7-(2-(tert-Butoxycarbonyl)-2-phenylacetamido)cephalosporanic acid (490 mg.; 1 mmole) and 1-methyl-1H-tetrazole-5-thiol (145 mg.; 1.25 mmole) in 15 ml. of dry nitromethane were heated at 85°-90° C. for 8 hours under nitrogen. TLC showed product, excess thiol reactant, and decarboxycated product, but no cephalosporanic acid starting material. The nitromethane was removed by evaporation. The residual orange foam was dissolved in 10 ml. of saturated sodium bicarbonate, 20 ml. of water was added, and the mixture was washed successively with ethyl acetate until the washes were clear. The ethyl acetate washes were combined, 20 ml. of water was added, and the mixture cooled to 0° C. and adjusted to pH 2.2 with 20 percent HCl. The layers were separated and the aqueous layer washed with ethyl acetate. The ethyl acetate portions were combined, washed with saturated sodium chloride, dried over magnesium sulfate, filtered, and evaporated to a brown foam, 455 mg. (83 percent yield). TLC was excellent, showing the presence of product, a trace of thiol, and a trace of decarboxylated product.

The 455 mg. of product (0.833 mmole) were dissolved in 7 ml. of ethyl acetate and lithium acetate (0.833 ml.) was added dropwise with stirring, resulting in a brown precipitate, the lithium salt. It was separated by filtration, washed with ethyl acetate, and dried overnight under vacuum at room temperature, 368 mg. (80 percent yield). The identity of the product was confirmed by TLC, NMR, bioautogram, elemental analysis, IR, and UV. TLC showed a trace of decarboxylated material. NMR (CDCl$_3$) δ 1.4 (s, 9, —COO tert C$_4$H$_9$), 3.6 (s, 2, 2—C$\underline{H}_2$), 3.85 (s, 3, C$\underline{H}_3$ of tetrazole), 4.3 (s, 2, 3—C$\underline{H}_2$S—), 4.44 and 4.45 (2s, 1,

4.9 (d, 1, J=6 Hz, C$_6$-$\underline{H}$), 5.8 (q, 1, J=6 Hz, C$_7$-$\underline{H}$), 7.35 (s, 5, $\phi$), 8.2 and 7.8 (2d, 1, J=9 Hz, —CON$\underline{H}$—), and 9.3 (s, 1, —COO$\underline{H}$).

EXAMPLE 51

PREPARATION OF 3-(((1-METHYL-1H-TETRAZOL-5-YL)THIO)METHYL)-7-(N-((1,3-DIMETHYLUREIDO)CARBONYL)-2-PHENYLGLYCYLAMIDO)-3-CEPHEM-4-CARBOXYLIC ACID IN NITROMETHANE 7-(N-((1,3-Dimethylureido)carbonyl)-2-phenylglycylamido)cephalosporanic acid (130 mg.; 0.25 mmole) was suspended in 5 ml. of nitromethane and 1-methyl-1H-tetrazol-5-thiol (43.5 mg.; 0.375 mmole) was added. The reaction mixture was heated at 85° under nitrogen for 12 hours, then held at room temperature over a weekend. The reaction mixture was then filtered and the solid washed with a small amount of nitromethane and dried in a vacuum oven at 35°, 83 mg. (58 percent yield) The identity of the product was confirmed by TLC, NMR, IR, UV, elemental analysis and bioautogram. NMR (DMSO-d$_6$) δ 2.65 (d, 3, J=4 Hz, —CONHC$\underline{H}_3$), 3.15 (s, 3, CONC$\underline{H}_3$CO—), 3.6 (s, 2, 2—C$\underline{H}_2$), 3.9 (s, 3, C$\underline{H}_3$ on tetrazole), 4.3 (s, 2, 3—C$\underline{H}_2$S—), 5.0 (d, 1, J=5 Hz, C6-H), 5.5 (d, 1, J=7 Hz,

5.7 (q, 1, C$_7$-$\underline{H}$), 5.8 (q, 1, —CON$\underline{H}$CH$_3$), 7.4 (s, 5, $\phi$), 9.3 (d, 1, J=8 Hz, $\phi$CHCON$\underline{H}$—), and 10 (d, 1, J=8 Hz,

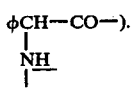

EXAMPLE 52

PREPARATION OF 3-(((1-METHYL-1H-TETRAZOL-5-YL)-THIO)METHYL)-7-(2-THIENYLACETAMIDO)-3-CEPHEM-4-CARBOXYLIC ACID IN ACETONITRILE, TETRABUTYLAMMONIUM IODIDE ADDED 7-(2-Thienylacetamido)cephalosporanic acid (2.0 grams; 5 mmole), 1-methyl-1H-tetrazole-5-thiol (1.2 grams; 10 mmole), and tetrabutylammonium iodide (0.2 gram) were mixed in 25 ml. of dry acetonitrile, heated to reflux, and refluxed for 8 hours. The reaction mixture was then cooled to room temperature and solvent removed on a rotary evaporator. The residue was treated with a hot mixture of 25 ml. of isopropyl acetate and 5 ml. of acetonitrile, filtered, and allowed to cool slowly. The product precipitated as light cream colored crystals and was filtered, washed with isopropyl acetate, and dried, 1.30 grams (57.5 percent yield). The NMR was identical with the NMR on the product of Example 5.

EXAMPLE 53

PREPARATION OF 3-(((1-METHYL-1H-TETRAZOL-5-YL)THIO)METHYL)-7-(2-THIENYLACETAMIDO)-3-CEPHEM-4-CARBOXYLIC ACID IN 1,2-DICHLOROETHANE (TETRABUTYLAMMONIUM IODIDE ADDED)

The reaction reported in Example 52 was repeated except that 1,2-dichloroethane was employed as solvent. Dicyclohexylamine (2 ml.) was added to obtain the product as the dicyclohexylamine salt, 1.55 grams (48.9 percent yield). The NMR was identical with the NMR on the product of Example 1.

EXAMPLE 54

PREPARATION OF 3-((PHENYLTHIO)METHYL)-7-(2-(2-THIENYL)ACETAMIDO)-3-CEPHEM-4-CARBOXYLIC ACID IN 1,2-DICHLOROETHANE, 1-METHYL-5-(METHYLTHIO)-1H-TETRAZOLE ADDED 7-(2-(2-Thienyl)acetamido)cephalosporanic acid (2.0 grams; 5 mmole), benzenethiol (0.75 ml.; 7.5 mmole), and 0.65 gram of 1-methyl-5-(methylthio)-1H-tetrazole were mixed in 25 ml. of 1,2-dichloroethane and heated to reflux. The reaction was followed by TLC and appeared to be complete in about 14 hours. Solvent was removed on a rotary evaporator and the residue was extracted repeatedly with diethyl ether. Exhaustive removal of solvent left 1.66 grams of tan solid product (74 percent yield). IR and NMR were identical with the same product prepared as described in preceding examples.

EXAMPLE 55

PREPARATION OF 3-(((1-METHYL-1H-TETRAZOL-5-YL)THIO)METHYL)-7-(2-(2-(THIENYLACETAMIDO)-3-CEPHEM-4-CARBOXYLIC ACID IN ISOPROPANOL 7-(2-(2-Thienyl)acetamido)cephalosporanic acid (2.0 grams; 5 mmole) and 1-methyl-1H-tetrazole-5-thiol (0.87 grams; 7.5 mmole) in 25 ml. of isopropanol were placed in a flask (equipped with a condenser, with a drying tube containing anhydrous calcium sulfate sold under the trademark Drierite). The flask was immersed in an oil bath at 84°-85° C. The reaction was followed by TLC. After 40 hours at 82°-83° C. only half of the cephalosporanic acid had reacted.

EXAMPLE 56

PREPARATION OF 3-((2-OXAZOLYLTHIO)METHYL)-7-(2-(1H-TETRAZOL-1-YL)ACETAMIDO)-3CEPHEM-4-CARBOXYLIC ACID IN NITROMETHANE

A suspension of 7-(2-(1H-tetrazol-1-yl)acetamido)-cephalosporanic acid (0.38 gram; 1.0 mmole) and 2-oxazolethiol (0.11 gram; 1.1 mmole) in 5 ml. of nitromethane was immersed in an oil bath at 90°–91° C. An atmosphere of dry nitrogen was maintained over the reaction mixture. After 20 minutes, all of the reactants had dissolved, and after 35 minutes, product began to crystallize. After 6 hours the reaction mixture was cooled to room temperature and the product was filtered, washed with 7 ml. of nitromethane, air dried, and vacuum dried for 3 hours at 40° C., yielding 0.36 gram (85.7 percent yield of off white crystals, m.p. 196° C. (dec). NMR showed the product to be 70 percent of the desired product and 30 percent of the cephalosporanic acid starting material.

The product was recrystallized from 5 ml. of DMSO-$d_6$ and 10 ml. of water, separated by filtration washed with 5 ml. of 2:1 water:DMSO-$d_6$, air dried, and vacuum dried at 50° C. for 6 hours, yielding 0.26 gram. NMR showed that the product contained 87 percent of the desired product and 13 percent of starting cephalosporanic acid. The recrystallization was repeated with 3 ml. of DMSO-$d_6$ and 6 ml. of water, stirring for 1 hour, resulting in 0.21 gram. NMR (DMSO-$d_6$) indicated that the starting cephalosporanic acid had been reduced to 5 percent, and confirmed the identity of the desired product: δ 3.75 (s, 2, 2—C$\underline{H}_2$), 4.34 (q, 2, 3—C$\underline{H}_2$S—, $J$=14 Hz), 5.16 (d, 1, C$_6$-$\underline{H}$, $J$=5 Hz), 5.76 (q, 1, C$_7$-$\underline{H}$, $J$=5 Hz, $J$=9 Hz), 5.44 (s, 2, —C$\underline{H}_2$CONH—), 7.28 (s, 1, oxazole C$_4$-$\underline{H}$), 8.14 (s, 1, oxazole C$_5$-$\underline{H}$), 9.37 (s, 1, tetrazole $\underline{H}$), and 9.53 (d, 1, —CON$\underline{H}$—, $J$=9 Hz).

EXAMPLE 57

PREPARATION OF 3-((2-OXAZOLYLTHIO)METHYL)-7-(2-FORMYLOXY-2-PHENYLACETAMIDO)-3-CEPHEM-4-CARBOXYLIC ACID IN 1,2-DICHLOROETHANE

A solution of 7-(2-formyloxy-2-phenylacetamido)-cephalosporanic acid methylene chloride solvate (0.52 gram; 1 mmole) and 2-oxazolethiole (0.12 gram; 1.1 mmole) in 20 ml. of 1,2-dichloroethane was refluxed for about 16 hours and then cooled to room temperature. TLC showed clear conversion to product. The reaction mixture was concentrated on a rotary evaporator to about 10 ml.; and upon standing, somewhat gelatinous crystals formed. They were filtered, washed with 1,2-dichloroethane, and dried, yielding 0.12 gram of gray solid.

Exhaustive removal of solvent from filtrate left 0.45 gram of light yellow foam. It was triturated with 25 ml. of diethyl ether, filtered, washed with diethyl ether, and dried yielding 0.21 gram of light yellow powder. The identity of the product was confirmed by NMR, δ 3.56 (m, 2, 2—C$\underline{H}_2$), 4.24 (q, 2, 3—C$\underline{H}_2$S—), $J$=13 Hz), 5.00 (d, 1, C$_6$-$\underline{H}$, $J$=5 Hz), 5.70 (q, 1, C$_7$-$\underline{H}$, $J$=5 Hz, $J$=9 Hz), 6.14 (s, 1,

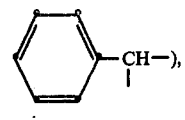

7.25 (s, 1, oxazole C$_4$-$\underline{H}$), 7.45 (m, 5, phenyl $\underline{H}$), 8.12 (s, 1, oxazole C$_5$-$\underline{H}$), 8.35 (s, 1, —C$\underline{H}$O), and 9.40 (d, 1, —CON$\underline{H}$—, $J$=9 Hz).

EXAMPLE 58

PREPARATION OF 3-(((4-PHENYL-2-THIAZOLYL)THIO)METHYL)-7-(2-(2-THIENYL)ACETAMIDO)-3-CEPHEM-4-CARBOXYLIC ACID IN ACETONITRILE

A mixture of 7-(2-(2-thienyl)acetamido)cephalosporanic acid (2.0 grams; 5 mmole) and 4-phenyl-2-thiazolethiol (1.44 grams; 7.5 mmole) in 35 ml. of acetonitrile was refluxed for about 16 hours, protected from atmospheric moisture with a drying tube containing anhydrous calcium sulfate sold under the trademark Drierite. TLC should clean conversion to a new spot.

Upon cooling the reaction mixture to room temperature and stirring it for 2 hours, the product crystallized and was filtered, washed with acetonitrile, and dried, 2.25 gram (85.6 percent yield, m.p. 180° C. (dec.). NMR confirmed the identity of the product.

EXAMPLE 59

PREPARATION OF 3-(((5-METHYL-1,3,4-THIADIAZOL-2-YL)THIO)-METHYL)-7-(2-(1H-TETRAZOL-1-YL)ACETAMIDO)-3-CEPHEM-4-CARBOXYLIC ACID IN NITROMETHANE 7-(2-(1H-Tetrazol-1-yl)acetamido)cephalosporanic acid (1.92 grams; 5 mmole) and 5 methyl-1,3,4-thiadiazole-2-thiol (0.79 gram; 6 mmole) were added to 25 ml. of alumina-treated nitromethane and the reaction mixture heated to 95° C. in an oil bath and allowed to stir for a total of 4 hours. TLC showed conversion except for a trace of cephalosporanic acid starting material (less than 2 percent). The reaction mixture was cooled to room temperature filtered, washed with nitromethane, and vacuum dried, 2.11 grams (92.5 percent yield), m.p. 183.5° C. (dec.). NMR confirmed the identity of the of the product.

EXAMPLE 60

PREPARATION OF 3-(((5-METHYL-1,3,4-THIADIAZOL-2-YL)THIO)-METHYL)-7-(2-(1H-TETRAZOL-1-YL)ACETAMIDO)-3-CEPHEM-4-CARBOXYLIC ACID IN PROPIONITRILE 7-(2-(1H-Tetrazol-1-yl)acetamido)cephalosporanic acid (1.92 grams; 5 mmole) and 5- methyl-1,3,4-thiadiazole-2-thiol (0.99 grams; 7.5 mmole) were added to 25 ml. of propionitrile (treated over neutral alumina) and heated to reflux (97° C.). The reaction mixture was refluxed with stirring for 9 hours. TLC showed only a trace of cephalosporanic acid starting material. The reaction mixture was cooled to room temperature, filtered, washed with propionitrile, and vacuum dried, 2.04 grams (89.5 percent yield), m.p. 186.5° C. (dec.). NMR confirmed the identity of the product.

EXAMPLE 61

PREPARATION OF 3-(((1-METHYL-1H-TETRAZOL-5-YL)THIO)METHYL)-7-(2-FORMYLOXY-2-PHENYLACETAMIDO)-3-CEPHEM-4-CARBOXYLIC ACID FROM 7-ACA IN 1,2-DICHLOROETHANE

7-ACA (7-aminocephalosporanic acid) (13.62 grams; 0.05 mole) was suspended in 100 ml. of 1,2-dichloroethane and trimethylsilyl acetamide (26.25 grams; 0.200 mole) was added. The reaction mixture was heated to 40° C. and the solid dissolved to yield a cloudy solution, which was cooled to 20° C.

A solution of 2-formyloxy-2-phenylacetyl chloride (10.92 grams; 0.055 mole) in 25 ml. of 1,2-dichloroethane was added dropwise over 20 minutes, with a temperature rise to 30° C. The reaction mixture was stirred for 2 hours, 100 ml. of 1,2-dichloroethane were added, and the reaction mixture was washed with three 100-ml. portions of water. The water washes were combined and extracted with two 50-ml. portions of 1,2-dichloroethane, which were back washed with 40 ml. of water. The 1,2-dichloroethane layers were combined, stirred 20 minutes with 2.0 grams of activated carbon sold under the trademark Darco G-60, and filtered through a diatomaceous earth sold under the trademark Hyflo. Total volume was 375 ml. Super-Cel of solution containing the desired 7-(2-formyloxy-2-phenylacetamido)cephalosporanic acid.

This solution was evaporated at about 30° C. to 336 grams, estimated to be 250 ml. of 1,2-dichloroethane and 22 grams of the 7-(2-formyloxy-2-phenylacetamido)cephalosporanic acid. 1-Methyl-1H-tetrazole-5-thiol (6.39 grams; 55 mmole) in 250 ml. of 1,2-dichloroethane was added and the reaction mixture heated to reflux. Water (apparently remaining from earlier washes) was azeotroped into the condensor and began returning into the vessel; a trap was employed to intercept water. TLC after 12 hours of reflux showed near normal reaction. The reaction mixture was cooled to room temperature and seeded to precipitate the product, 3-(((1-methyl-1H-tetrazol-5-yl)thio)methyl)-7-(2-formyloxy)-2-phenylacetamido)-3-cephem-4-carboxylic acid. After about two hours, the product was filtered and washed with 63 ml. of 1,2-dichloroethane, 13.90 grams (56.7 percent yield based on 7-ACA). TLC of the product was clean. The NMR confirmed the identity of the product and was identical with the NMR of the product prepared as reported in Example 16.

EXAMPLE 62

PREPARATION OF 3-(((1-METHYL-1H-TETRAZOL-5-YL)THIO)METHYL)-7-(2-FORMYLOXY-2-PHENYLACETAMIDO)-3-CEPHEM-4-CARBOXYLIC ACID IN 1,2-DICHLOROETHANE 7-(2-Formyloxy-2-phenylacetamido)cephalosporanic acid (2.33 grams; 5 mmole) and 1-methyl-1H-tetrazole-5-thiol (0.64 gram; 5.5 mmole) were added to 25 ml. of 1,2-dichloroethane and the mixture refluxed for 12 hours. The reaction mixture was cooled to room temperature, then reheated to reflux and 10 ml. of solvent distilled off. Then 10 ml. of carbon tetrachloride was added dropwise near the reflux temperature (77° C.). The resulting mixture was allowed to cool to room temperature and stirred for 1 hour. The product was separated by filtration, washed with 14 ml. of 40 percent carbon tetrachloride in 1,2-dichloroethane, and dried at 50° C. under vacuum, 2.12 grams of light colored solid (86.5 percent yield). The NMR was identical with the NMR on the product prepared as reported in Example 16.

EXAMPLE 63

PREPARATION OF 3-(((3-BENZYLOXYCARBONYLAMINOMETHYL)-1,2,4-TRIAZOL-5-YL)THIO)METHYL)-7-(2-(2-THIENYL)ACETAMIDO)-3-CEPHEM-4-CARBOXYLIC ACID IN NITROMETHANE 7-(2-(2-Thienyl)acetamido)cephalosporanic acid (2 grams; 5 mmole) and 3-(benzyloxycarbonylaminomethyl)-1,2,4-triazole-5-thiol (2 grams; 7.6 mmole) in 35 ml. of nitromethane were heated at 80°–90° C. for 6 hours, with stirring. The reaction mixture was cooled and filtered to separate the product. It was recrystallized twice from aqueous acetone, 1.2 grams of cream colored crystals, m.p. 174°–178° C. (dec.) (40 percent yield).

Anal., Calc. for $C_{25}H_{24}N_6O_6S_3$: C, 49.99; H, 4.03; N, 13.99; S, 16.01. Found: C, 50.20; H, 4.03; N, 13.76; S, 15.68.

EXAMPLE 64

PREPARATION OF 3-(((1-(CARBOXYMETHYL)-1H-TETRAZOL-5-YL)THIO)METHYL)-7-(2-(2-THIENYL)ACETAMIDO)-3-CEPHEM-4-CARBOXYLIC ACID IN ACETONITRILE 7-(2-(2-Thienyl)acetamido)cephalosporanic acid (1.0 gram; 2.5 mmole) and 1-(carboxymethyl)-1-H-tetrazole-5-thiol (0.61 gram; 3.8 mmole) in 75 ml. of acetonitrile was heated to boiling and 35 ml. of the solvent distilled off. The reaction mixture was then refluxed for 13 hours, cooled, filtered, and concentrated under reduced pressure. The residue was dissolved in ethyl acetate, washed with 1N HCl and brine, and dried over sodium sulfate. Hexane was added, resulting in a precipitate which was separated and triturated with ether, 0.475 gram of tan solid (38 percent yield). The identity of the product was established by comparison with an authentic sample prepared by another synthetic route.

EXAMPLE 65

PREPARATION OF 3-(((5-METHYL-1,3,4-THIADIAZOL-2-YL)THIO)METHYL)-7-(3-CHLOROPROPIONAMIDO)-3-CEPHEM-4-CARBOXYLIC ACID IN NITROMETHANE

A stirred suspension of 7-(3-chloropropionamido)cephalosporanic acid (1.0 gram; 2.5 mmole) and 5-methyl-1,3,4-thiadiazole-2-thiol (0.4 gram; 3 mmole) in 20 ml. of nitromethane was immersed in an oil bath at 95°–96° C. According to TLC, reaction was complete in 3 hours. The reaction mixture was cooled to room temperature, filtered, and evaporated under vacuum, leaving a light red oil which crystallized on standing at room temperature for 2 hours. It was then triturated with 15 ml. of ethyl acetate, filtered, washed with ethyl acetate, and dried, 0.64 gram (55.2 percent yield). Identity of the product was confirmed by IR, UV, titration, microanalysis, and NMR.

Anal., Calc. for $C_{16}H_{19}ClN_4O_4S_3$: C, 41.51; H, 4.14; N, 12.10; S, 20.78; Cl, 7.66. Found: C, 41.70; H, 4.23; N, 11.84; S, 20.51; Cl, 7.88.

EXAMPLE 66

PREPARATION OF 3-(((1-BENZYL-1H-1,2,3-TRIAZOL-5-YL)THIO)-METHYL)-7-(2-(2-THIENYL)ACETAMIDO)-3-CEPHEM-4-CARBOXYLIC ACID IN 1,2-DICHLOROETHANE 7-(2-(2-Thienyl)acetamido)cephalosporanic acid (200 mg.; 0.5 mmole) and 1-benzyl-1H-trazole-5-thiol (140 mg.; 0.7 mmole) were mixed in 15 ml. of 1,2-dichloroethane and heated at 65°–70° C. for 21 hours. Solvent was removed under reduced pressure, 25 ml of a saturated sodium bicarbonate solution was added, and the mixture was extracted with two portions of ethyl acetate. Fresh ethyl acetate was added to the remaining aqueous solution which was cooled in an ice bath and the pH adjusted to 2.5 with 20 percent HCl solution. The acidic product was extracted with two portions of ethyl acetate, and the combined ethyl acetate was washed with saturated NaCl solution and dried over anhydrous magnesium sulfate. The magnesium sulfate was filtered and ethyl acetate removed under reduced pressure, 76 mg. Thin layer chromatography showed it to be a mixture of starting material and product by comparison with an authentic sample of product and starting materials.

EXAMPLES 67–72

DISPLACEMENT BY VARIOUS THIOLS OF 7-METHOXY-7-(2-(1H-TETRAZOL-1-YL)ACETAMIDO)CEPHALOSPORANIC ACID IN NITROMETHANE

7-Methoxy-7-(2-(1H-tetrazol-1-yl)acetamido)cephalosporanic acid was reacted with various thiols in nitromethane. The procedures were essentially the same as reported above, except that high pressure liquid chromatography was employed to purify the products from unreacted starting material. The products and identification were as follows:

3-(((1-methyl-1H-tetrazol-5-yl)thio)methyl)-7-methoxy-7-(2-(1H-tetrazol-1yl)acetamido)-3-cephem-4-carboxylic acid, uv max (ethanol) 273 mμ (ε 9,082).

3-(((5-methyl-1,3,4-thiadiazol-2-yl)thio)methyl-7-methoxy-7-(2-(1H-tetrazol-1-yl)acetamido)-3-cephem-4-carboxylic acid, uv max (ethanol) 273 mμ (ε 12,785).

Anal., Calc. for $C_{15}H_{16}N_8O_5S_3$: C, 37.18; H, 3.33; N, 23.13. Found: C, 36.99; H, 3.31; N, 22.86.

3-(((5-methyl-1,3,4-oxadiazol-2-yl)thio)methyl)-7-methoxy-7-(2-(1H-tetrazol-1-yl)acetamido)-3-cephem-4-carboxylic acid, uv max (ethanol) 269 mμ (ε 8,910).

Anal., Calc. for $C_{15}H_{16}N_8O_6S_2$: C, 38.46; H, 3.44; N, 23.92. Found: C, 38.58; H, 3.69; N, 23.91.

3-(((1-(carboxymethyl)-1H-tetrazol-5-yl)thio)methyl)-7-methoxy-7-(2-(1H-tetrazol-1-yl)acetamido)-3-cephem-4-carboxylic acid, uv max (ethanol) 269 mμ (ε 7669).

Anal., Calc. for $C_{15}H_{16}N_{10}O_7S_2$: C, 35.16; H, 3.15; N, 27.33. Found: C, 35.42; H, 3.38; N, 27.39.

3-(((4,5-dihydro-6-hydroxy-4-methyl-5-oxo-1,2,4-triazin-3-yl)thio)methyl)-7-methoxy-7-(2-(1H-tetrazol-1-yl)acetamido)-3-cephem-4-carboxylic acid, uv max (ethanol) 274 (ε 11,967).

Anal., Calc. for $C_{16}H_{17}N_9O_7S_2$: C, 37.57; H, 3.35; N, 24.65. Found: C, 36.96; H, 3.80; N, 27.63.

3-(((1,3,4-triazol-5-yl)thio)methyl)-7-methoxy-7-(2-(1H-tetrazol-1-yl)acetamido)-3-cephem-4-carboxylic acid Anal., Calc. for $C_{14}H_{15}N_9O_5S_2$: C, 37.08; H, 3.33; N, 27.80. Found: C, 36.98; H, 3.43; N, 27.79.

EXAMPLE 73

PREPARATION OF 3-(((1-METHYL-1H-TETRAZOL-5-YL)THIO)METHYL)-7-(2-(4-ETHYL-2,3-DIOXO-1-PIPERAZINYLCARBONYLAMINO)-2-PHENYLACETAMIDO)-3-CEPHEM-4-CARBOXYLIC ACID IN NITROMETHANE 7-(2-(4-Ethyl-2,3-dioxopiperazinylcarbonylamino)-2-phenylacetamido)cephalosporanic acid hydrate (0.3 gram; 0.5 mmole) and 1-methyl-1H-tetrazole-5-thiol (0.0725 gram; 0.625 mmole) were added to 6 ml. of nitromethane which had been dried over alumina and the mixture was heated at 85° C., under nitrogen, for about 12 hours. The nitromethane was then evaporated and the residual brown foam redissolved in sodium bicarbonate solution and washed twice with ethyl acetate. Fresh ethyl acetate was added and the mixture cooled to 0° C. and adjusted to pH of 2.3. The layers were separated and the aqueous layer was washed with ethyl acetate. The ethyl acetate portions were combined, washed with saturated NaCl solution, dried over anhydrous magnesium sulfate, filtered, and evaporated, yielding a pale yellow powder, 130 mg. (about 40% of theoretical). Identity of the product was confirmed by NMR δ 1.2 (t, 3, —NCH$_2$C$\underline{H}_3$, $\underline{J}$ = 7 Hz), 3.65 (m, 6, >N—C$\underline{H}_2$CH$_3$ and piperazinyl $\underline{H}$), 4.0 (s, 3, —C$\underline{H}_3$ of tetrazole), 4.4 (s, 2, 3—C$\underline{H}_2$S—), 5.1 (d, 1, C$_6$-$\underline{H}$, $\underline{J}$ = 6 Hz), 5.8 (d, 1, C$_7$-$\underline{H}$, $\underline{J}$ = 8 Hz), 6.0 (d, 1,

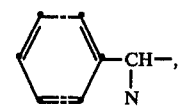

J=6 Hz), 7.4 (m, 5, phenyl-H), 8.4 (d, 1, —CHCON$\underline{H}$—, $\underline{J}$ = 8 Hz), and 10.0 (d, 1,

$\underline{J}$ = 6 Hz).

EXAMPLE 74

PREPARATION OF 3-(((1-CARBOXYMETHYL)-1H-TETRAZOL-5-YL)THIO)METHYL)-7-(2-(4-ETHYL-2,3-DIOXO-1-PIPERAZINYLCARBONYLAMINO)-2-PHENYLACETAMIDO)-3-CEPHEM-4-CARBOXYLIC ACID IN 1,2-DICHLOROETHANE 7-(2-(4-Ethyl-2,3-dioxopiperazinylcarbonylamino)-2-phenylacetamido)cephalosporanic acid hydrate (0.3 gram; 0.5 mmole) was dissolved in 45 ml. of 1,2-dichloroethane which had been dried over alumina and the solution was heated to 95° to azeotrope off water. After 40 ml. of solvent had been collected, nitromethane (10 ml.) and 1-(carboxymethyl)-1H-tetrazole-5-thiol (0.160 gram; 1 mmole) were added and the reaction mixture maintained at 90° C. for 12 hours under nitrogen. The reaction mixture was then filtered and solvent evaporated, yielding a gum to which ethyl acetate and saturated sodium bicarbonate solution were added. The mixture was washed twice with ethyl acetate, then fresh ethyl acetate was added and the mixture cooled to 0° C. and adjusted to pH 2.3 with 20% HCl. The layers were separated and the aqueous layer was washed with ethyl acetate. The ethyl acetate layers were combined and washed with saturated HCl, dried over anhydrous magnesium sulfate, filtered, evaporated, and dried at room temperature, 123 mg. The identity of the product was confirmed by NMR, δ 1.2 (t, 3, —NCH$_2$CH$_3$, J = 7 Hz), 3.6 (m, 4, >N—CH$_2$CH$_3$ and piperazinyl 5-H), 4.1 (m, 2, piperazinyl 4-H), 4.4 (s, 2, 3—CH$_2$S—), 5.1 (d, 1, C$_6$-H, J = 5 Hz), 5.3 (s, 2, tetrazole 1—CH$_2$COOH), 5.75 (d, 1, C$_7$-H, J = 6 Hz), 5.9

(d, 1, 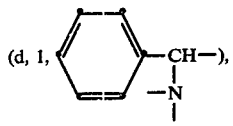), 7.4 (m, 5, phenyl H), and 9.9 (d, 1,

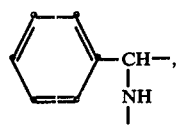

J = 7 Hz).

EXAMPLE 75

PREPARATION OF 3-(((4-METHYL-5,6-DIOXO-1,2,4-TRIAZIN-3-YL)THIO)METHYL)-7-(2-(4-ETHYL-2,3-DIOXO-1-PIPERAZINYLCARBONYLAMINO)-2-PHENYLACETAMIDO)-3-CEPHEM-4-CARBOXYLIC ACID IN NITROMETHANE 7-(2-(4-Ethyl-2,3-dioxo-1-piperazinylcarbonylamino)-2-phenylacetamido)cephalosporanic acid hydrate (0.3 gram; 0.5 mmole) and 4-methyl-5,6-dioxo-1,2,4-triazine-3-thiol (0.111 gram; 0.625 mmole) were dissolved in 10 ml. of nitromethane under nitrogen at room temperature, and the reaction mixture heated at 85° C. for about 12 hours. A brown gummy precipitate formed and was discarded. Solvent was evaporated slowly, and a yellow precipitate formed. The residue was cooled, filtered, and washed with diethyl ether, yielding two crops, identical on TLC, of off-white solid. Total yield was 80 mg. (24 percent yield). Identity of the product was confirmed by NMR δ 1.1 (t, 3, —NCH$_2$CH$_3$, J = 6 Hz), 3.3 (s, 3, triazine—CH$_3$), 3.65 (m, 4, >N—CH$_2$CH$_3$ and piperazinyl 5-H), 4.0 (m, 2, piperazinyl 6-H), 4.6 (s, 2, 3—CH$_2$S—), 5.1 (d, 1, C$_6$-H, J = 5 Hz), 5.75 (m, 2,

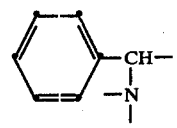

and C$_7$-H), 7.45 (m, 5, phenyl H), 9.5 (d, 1, —CH-CONH—, J = 8 Hz) and 10.0 (d, 1,

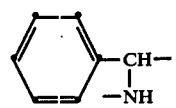

J = Hz).

EXAMPLE 76

PREPARATION OF 3-(((5-METHYLTHIO)-1,3,4-THIADIAZOL-2-YL)THIO)METHYL)-7-(2-(1H-TETRAZOL-1-YL)ACETAMIDO)-3-CEPHEM-4-CARBOXYLIC ACID IN NITROMETHANE 7-(2-(1H-Tetrazol-1-yl)acetamido)cephalosporanic acid (15.0 grams; 39.2 mmole) and 5-(methylthio)-1,3,4-thiadiazole-2-thiol (6.43 grams; 39.2 mmole) were suspended in 500 ml. of nitromethane which had been passed through a column of neutral alumina. The mixture was heated to 95° C. and the reaction mixture was maintained at 95° C. for 6 hours, then cooled overnight, filtered, washed with 250 ml. of nitromethane, and dried at 45° C. for 4 hours, 18.08 gram (94.9% yield).

This product was added to 150 ml. of water and 4.0 ml. of acetic acid. The pH was adjusted to 6.3 with 1N NaOH (required 107 ml.) and the mixture was stirred for 1 hour. A solution of 257 ml. of 60% sodium lactate and 65 ml. of ethanol was then added, and the resulting mixture allowed to stand for 45 minutes. It was then stirred for 45 minutes, filtered, washed three times with ethanol and dried, 18.1 grams.

The product was reslurried in 300 ml. of ethanol for 3 hours, filtered, washed with ethanol, and dried, 14.85 grams. The identity of the product was confirmed by HPLC.

EXAMPLES 77–84

PREPARATION OF 3-(((5-METHYL-1,3,4-THIADIAZOL-2-YL)THIO)-METHYL)-7-(2-(1H-TETRAZOL-1-YL)ACETAMIDO)-3-CEPHEM-4-CARBOXYLIC ACID IN VARIOUS SOLVENTS 7-(2-(1H-Tetrazol-1-yl)acetamido)cephalosporanic acid was reacted with 5-methyl-1,3,4-thiadiazole-2-thiol in various solvents. The key details of the reactions are summarized below (all other aspects of the reaction being conventional).

| Amt. of Cehphalosporanic acid | Amt. of Thiol | Solvent | Temperature | Time | % Yield | Analysis |
|---|---|---|---|---|---|---|
| 1.91 g | 0.86 g | acetonitrile (sieve dried) | reflux | 24 hours | 87 | 190° C |
| 0.96 g | 0.363 g | nitrobenzene | 85° C. and 100° C. | ~16 hours ~72 hours | 83 | 181° C. (dec.) |
| " | 0.5 g | 1:1 mixture of 1,2-dichloroethane and nitromethane | 85° C. | 14 hours | 88 | 182–183° C. (dec.) |
| " | " | nitroethane | 90° C. | 16 hours | 84 | 177° C. (dec.) |
| 3.82 g | 1.98 g | propylene carbonate | 95° C. | 8 hours | 68 | — |

-continued

| Amt. of Cehphalosporanic acid | Amt. of Thiol | Solvent | Temperature | Time | % Yield | Analysis |
|---|---|---|---|---|---|---|
| 1.91 g | 0.99 g | ethylene carbonate | 95° C. | 6 hours | 22 | — |
| 2.02 g* | 1.0 g | acetic acid | 85° C. | 5 hours | 55 | — |
| 1.92 g | 0.79 g | mixture of 52.5% nitromethane and 47.5% 2-nitropropane | 95° C. | 3 hours 50 mins. | 89 | — |

*as the sodium salt

EXAMPLE 85

PREPARATION OF LITHIUM 3-(((1-METHYL-1H-TETRAZOL-5-YL)THIO)METHYL)-7-(2-HYDROXY-2-PHENYLACETAMIDO)-3-CEPHEM-4-CARBOXYLATE IN GLACIAL ACETIC ACID 7-(2-Hydroxy-2-phenylacetamido)cephalosporanic acid (0.48 gram; 1 mmole) and 1-methyl-1H-tetrazole-5-thiol (0.5 gram; 4.3 mmole) were reacted in 15 ml. of glacial acetic acid at 84°-86° C. for 8 hours. The reaction mixture was cooled to room temperature and iodine (0.4 gram; 1.6 mmole) added to convert unreacted thiol to the disulfide. The mixture was stirred 20 minutes at room temperature, then poured into 100 ml. of ethyl acetate and 50 ml. of water and excess $I_2$ removed by addition of sodium sulfite. The layers were separated and the ethyl acetate layer washed with two 100 ml. portions of water and one 50 ml. portion of 20% NaCl solution and dried over anhydrous sodium sulfate. Ethyl acetate was removed on a rotary evaporator, and the residue dissolved in 10 ml. of methanol. Lithium acetate dihydrate (0.21 gram; 2 mmole) was added and the mixture stirred for 20 minutes at room temperature. The product crystallized and was separated by filtration, washed with 5 ml. of methanol and dried, yielding 0.34 gram of white cyrstals (69.4% yield). The identity of the product was confirmed by NMR: $\delta$ 3.50 (ABq, J $\simeq$ 17 Hz), 3.92 (s, —$CH_3$ of tetrazole), 4.20 (s, 3—$\underline{CH_2}$S—), 5.04 (d, $C_6$-H, J = 5 Hz), 5.24 (s, $\phi$CHCONH—), 5.64 (d, $C_7$-$\underline{H}$, J = 5 Hz), and 7.44 (s, $\phi$-$\underline{H}$). The NMR spectrum was identical with an NMR spectrum on an authentic sample of the product prepared by aqueous displacement.

EXAMPLE 86

7-(2-(o-(tert-Butoxycarbonylaminomethyl)phenyl-)acetamido)cephalosporanic acid (0.2 gram; 0.386 mmole) and 1-methyl-1H-tetrazole-5-thiol (0.047 gram; 0.405 mmole) were reacted in 5 ml. of nitromethane at 85° C., under nitrogen, for 12 hours, yielding 3-(((1-methyl-1H-tetrazol-5-yl)thio)methyl)-7-(2-(o-(tert-butoxycarbonylaminomethyl)phenyl)-acetamido)-3-cephem-4-carboxylic acid. Identity of the product was confirmed by NMR, $\delta$ 1.45 (s, 9, —$C(\underline{CH_3})_3$, 3.65 (s, 4, 2—$\underline{CH_2}$ and —$\underline{CH_2}$CONH—), 3.85 (s, 3, —$\underline{CH_3}$ of tetrazole), 4.3 (m, 4, 3—$\underline{CH_2}$S— and —$\underline{CH_2}$NHCOO-tert-$C_4H_9$), 5.0 (d, 2, $C_6$-$\underline{H}$, J = 4 Hz), 5.7 (q, 1, $C_7$-$\underline{H}$), 7.25 (s, 5, phenyl —$\underline{H}$ and —CON$\underline{H}$—), and 8.9 (s, 1, —COO$\underline{H}$).

EXAMPLE 87

7-(2-Ureido-2-phenylacetamido)cephalosporanic acid (0.224 gram; 0.5 mmole) and 1-methyl-1H-tetrazole-5-thiol (0.061 gram; 0.525 mmole) were reacted in 8 ml. of nitromethane at 85° C., for 12 hours, yielding 3-(((1-methyl-1H-tetrazol-5-yl)thio)methyl)-7-(2-ureido-2-phenylacetamido)-3-cephem-4-carboxylic acid. Identity of the product was confirmed by NMR, $\delta$ 3.5 (d, 2, 2—$\underline{CH_2}$, J = 3 Hz), 3.83 (s, 3, —$\underline{CH_3}$ of tetrazole), 4.17 (d, 2, 3—$\underline{CH_2}$S—, J = 3 Hz), 4.9 (d, 1, $C_6$-$\underline{H}$, J = 5 Hz), 5.4 (d, 1, —$\underline{CH_2}$CONH—, $\underline{J}$ = 8 Hz) 5.6 (m, 3, $C_7$-$\underline{H}$ and —N$\underline{H_2}$), 6.7 (d, 1,

$\underline{J}$ = 8 Hz), 7.25 (m, 5 phenyl $\underline{H}$), and 9.2 (d, 1, —$CH_2$CON$\underline{H}$—, $\underline{J}$ = 8 Hz).

EXAMPLE 88

7-(2-Cyanoacetamido)cephalosporanic acid (0.339 gram; 1 mmole) and 1-methyl-1H-tetrazole-5-thiol (0.122 gram; 1.05 mmole were reacted in 10 ml. of nitromethane at 85° C., under nitrogen, for 12 hours, yielding 3-(((1-methyl-1H-tetrazol-5-yl)thio)methyl)-7-(2-cyanoacetamido)-3-cephem-4-carboxylic acid. Identity of the product was confirmed by NMR, $\delta$ 3.5 (s, 2, 2—$\underline{CH_2}$), 3.65 (s, 2 CN$CH_2$CONH—), 3.95 (s, 3, —$\underline{CH_3}$ of tetrazole), 5.35 (s, 2, 3—$\underline{CH_2}$S—), 5.1 (d, 1, $C_6$-$\underline{H}$, $\underline{J}$ = 6 Hz), 5.75 (q, 1, $C_7$-$\underline{H}$, $\underline{J}$ = 4 Hz, 7.8 (s, 1, —COO$\underline{H}$), and 8.7 (d, 1, —$CH_2$CON$\underline{H}$—, $\underline{J}$ = 9 Hz).

EXAMPLE 89

7-(2-(m-Chlorophenylthio)acetamido)cephalosporanic acid (0.390 gram; 0.855 mmole) and 1-methyl-1H-tetrazole-5-thiol (0.104 gram; 0.9 mmole) were reacted in 10 ml. of nitromethane at 85° C., under nitrogen, for 12 hours, yielding 3-(((1-methyl-1H-tetrazol-5-yl)thio)-methyl)-7-(2-(m-chlorophenylthio)acetamido)-3-cephem-4-carboxylic acid. Identity of the product was confirmed by NMR $\delta$ 3.6 (s, 2, 2—$\underline{CH_2}$, 3.75 (s, 2, —$\underline{CH_2}$CONH—), 3.9 (s, 3, —$\underline{CH_3}$ of tetrazole), 4.4 (s, 2, 3—$\underline{CH_2}$S-), 5.0 (d, 1, $C_6$-$\underline{H}$, $\underline{J}$ = 5 Hz), 5.8 (q, 1, $C_7$-$\underline{H}$, $\underline{J}$ = 4 Hz), 7.15 (m, 4, pehnyl-$\underline{H}$), 7.7 (d, 1, —$CH_2$CON$\underline{H}$—, $\underline{J}$ = 8 Hz), and 8.5 (s, 1, COO$\underline{H}$).

EXAMPLE 90

7-(2-Phenylthio)acetamido)cephalosporanic acid (0.422 gram; 1 mmole) and 1-methyl-1H-tetrazole-5-thiol (0.122 gram; 1.05 mmole) were reacted in 10 ml. of nitromethane at 85° C., under nitrogen, for 12 hours, yielding 3-(((1-methyl-1H-tetrazol-5-yl)thio)methyl-7-(2-(phenylthio)acetamido)-3-cephem-4-carboxylic acid. Identity of the product was confirmed by NMR, $\delta$ 3.7 (s, 4, —$\underline{CH_2}$CONH— and 2—$\underline{CH_2}$), 3.9 (s, 3, —$\underline{CH_3}$ of tetrazole), 4.35 (s, 2, 3—$\underline{CH_2}$S—), 4.9 (d, 1, $C_6$-$\underline{H}$, J = 6 Hz), 5.8 (q, 1, $C_7$-$\underline{H}$, $\underline{J}$ = 4 Hz), 7.25 (s, 5, phenyl-$\underline{H}$), 7.7 (d, 1, —$CH_2$CON$\underline{H}$—, $\underline{J}$ = 8 Hz), and 9.4 (s, 1, —COO$\underline{H}$).

EXAMPLE 91

7-(2-(2-Thienyl)acetamido)cephalosporanic acid (3.96 gram; 10 mmole) and 1-methyl-1H-tetrazole-5-thiol (1.28 gram, 11 mmole) were reacted in 98 ml. of n-butyl formate at 84°–86° C. for 48 hours, yielding 3-(((1-methyl-1H-tetrazol-5-yl)thio)methyl)-7-(2-(2-thienyl)acetamido)-3-cephem-4-carboxylic acid, m.p. 167.5°–168° C., yield 79.9%. The NMR spectrum on the product was identical with the NMR spectrum on the product of Example 5.

EXAMPLE 92

The reaction reported in Example 91 was repeated on the same scale but in 150 ml. of toluene at 84°–86° C., for 136 hours. The product melted at 163°–163.5° C. and was obtained in 88.5% yield. The NMR spectrum on the product was identical with the NMR spectrum on the product of Example 5.

EXAMPLE 93

7-(tert-Butoxycarbonylamino)cephalosporanic acid (0.372 gram; 1 mmole) and 1-methyl-1H-tetrazole-5-thiol (0.122 gram; 1.05 mmole) were reacted in 10 ml. of nitromethane at 80° C. for 12 hours, yielding 3-(((1-methyl-1H-tetrazol-5-yl)thio)methyl)-7-(tert-butoxycarbonylamino)-3-cephem-4-carboxylic acid. The identity of the product was confirmed by NMR, δ 1.45 (s, 9, —C(C$\underline{H}_3$)$_3$), 3.7 (s, 2, 2—C$\underline{H}_2$), 3.95 (s, 3, —C$\underline{H}_3$ of tetrazole), 4.4 (s, 2, 3—C$\underline{H}_2$S—), 5.0 (s, 1, C$_6$-H), 5.6 (s, 2, C$_7$-$\underline{H}$ and —CH$_2$CON$\underline{H}$), and 13 (s, 1, —COO$\underline{H}$).

EXAMPLE 94

7-(2-(4-Ethyl-2,3-dioxopiperazinylcarbonylamino)-2-(p-hydroxyphenyl)acetamido)cephalosporanic acid (0.180 gram; 0.306 mmole) and 1-methyl-1H-tetrazole-5-thiol (0.0374 gram; 0.322 mmole) were reacted in 6 ml. of nitromethane at 80° C. for 12 hours, yielding 3-(((1-methyl-1H-tetrazol-5-yl)thio)methyl)-7-(2-(4-ethyl-2,3-dioxopiperazinylcarbonylamino)-2-(p-hydroxyphenyl)acetamido)-3-cephem-4-carboxylic acid. The identity of the product was confirmed by NMR, δ 1.2 (t, 3, >N—CH$_2$C$\underline{H}_3$), 3.6 (m, 6, 2—C$\underline{H}_2$, piperazinyl 6-$\underline{H}$ and >N—C$\underline{H}_2$CH$_3$), 3.9 (m, 2, piperazinyl 5-$\underline{H}$), 3.95 (s, 3, —C$\underline{H}_3$ of tetrazole), 4.4 (s, 2, 3—C$\underline{H}_2$S—), 5.0 (d, 1, C$_6$-$\underline{H}$, $\underline{J}$ = 6 Hz), 5.6 (d, 1, C$_7$-$\underline{H}$, $\underline{J}$ = 6 Hz), 5.8 (d, 1,

$\underline{J}$ = 8 Hz), 6.8 (d, 2, phenyl-$\underline{H}$, $\underline{J}$ = 8 Hz), 7.3 (d, 2, phenyl-$\underline{H}$, $\underline{J}$ = 8 Hz), 8.3 (d, 1,

$\underline{J}$ = 8 Hz), and 9.9 (d, 1,

$\underline{J}$ = 6 Hz.

EXAMPLE 95

7-(2-(1H-Tetrazol-1-yl)acetamido)cephalosporanic acid (0.38 gram; 1 mmole) and 1,3,4-thiadiazole-2-thiol (0.15 gram; 1.27 mmole) were reacted in 15 ml. of autonitrile at reflux, under nitrogen, for 24 hours, yielding 3-(((1,3,4-thiadiazol-2-yl)thio)methyl)-7-(2-(1H-tetrazol-1-yl)acetamido)-3-cephem-4-carboxylic acid. The identity of the product was confirmed by NMR, δ 3.74 (m, 2, 2—C$\underline{H}_2$—), 4.48 (q, 2, 3—C$\underline{H}_2$S—, J$_{AB}$ = 14), 5.16 (d, 1, C$_6$-$\underline{H}$, $\underline{J}$ = 5), 5.42 (s, 2, —C$\underline{H}_3$ of tetrazolyl), 5.76 (q, 1, C$_7$-$\underline{H}$, $\underline{J}_{6,7}$ = 5, J$_{7NH}$ = 8), 8.87 (s, 1, tetrazole ring), 9.40 (s, 1, thiadiazolethiol starting material), 9.53 (d, 1, —CH$_2$CON$\underline{H}$—, $\underline{J}$ = 8 Hz), and 9.57 (s, 1, thiadiazole ring).

EXAMPLE 96

7-(5-Carbomethoxy-5-(2,4-dichlorobenzamido)-valeramido)cephalosporanic acid (0.3 gram; 0.5 mmole) and 5-methyl-1,3,4-thiadiazole-2-thiol (0.1 gram; 0.75 mmole) were reacted in 1,2-dichloroethane at reflux for 16½ hours, yielding 3-(((5-methyl-1,3,4-thiadiazol-2-yl)thio)methyl)-9-(5-carbomethoxy-5-(2,4-dichlorobenzamido)valeramido)-3-cephem-4-carboxylic acid.

EXAMPLE 97

7-(2-(1H-Tetrazol-1-yl)acetamido)cephalosporanic acid (1.91 grams; 5 mmole) and 1-methyl-1H-tetrazole-5-thiol (0.7 gram; 6 mmole) in 50 ml. of acetonitrile were refluxed for 24 hours and cooled to room temperature. Solvent was removed on a rotary evaporator, to about 10 ml. Ethanol (40 ml.) was added; followed by a solution of 0.3 gram of lithium hydroxide in 10 ml. of methanol. The product, lithium 3-(((1-methyl-1H-tetrazol-5-yl)thio)methyl)-7-(2-(1H-tetrazol-1-yl)acetamido)-3-cephem-4-carboxylate, crystallized. After the reaction mixture was stirred for 45 minutes at room temperature, the product was separated by filtration, washed with ethanol, and vacuum dried at 40° C., 1.60 grams (72% yield). The identity of the product was confirmed by NMR.

EXAMPLE 98

7-(2-Formyloxy-2-phenylacetamido)cephalosporanic acid (4.6 grams; 8.8 mmole) and 5-methyl-1,3,4-thiadiazole-2-thiol (1.52 grams; 11.5 mmole) in 50 ml. of 1,2-dichloroethane were refluxed for 12 hours and cooled to room temperature. The product, 3-(((5-methyl-1,3,4-thiadiazol-2-yl)thio)methyl)-7-(2-formyloxy-2-phenylacetamido)-3-cephem-4-carboxylic acid, precipitated as a thick paste. The mixture was diluted with an additional 50 ml. of 1,2-dichloroethane and stirred 4 hours at room temperature. The product was then separated by filtration, washed with 1,2-dichloroethane until the filtrate was clear, and vacuum dried at 40°–45° C., 2.8 grams (63% yield). The identity of the product was confirmed by NMR.

EXAMPLE 99

7-(2-(1H-Tetrazol-1-yl)acetamido)cephalosporanic acid (8.9 grams; 23.2 mmole) and 4,5-dihydro-6-hydroxy-4-methyl-5-oxo-1,2,4-triazine-3-thiol (4.1 grams; 25.8 mmole) in 200 ml. of acetonitrile were refluxed 23 hours then cooled to room temperature. Product had crystallized during the course of the reaction and was separated by filtration, washed with 50 ml. of acetonitrile, and vacuum dried at 40°–50° C., 9.70 grams (86.6% yield). The identity of the product 3-(((4,5-dihydro-6-hydroxy-4-methyl-5-oxo-1,2,4-triazin-3-yl)thio)-methyl)-7-(2-(1H-tetrazol-1-yl)acetamido)cephalosporanic acid, was confirmed by NMR.

EXAMPLES 100–121

Yet other reactions in accordance with the present process can be conducted as follows:

7-(2-Sulfo-2-phenylacetamido)cephalosporanic acid, sodium salt, is reacted with 1-methyl-1H-tetrazole-5-thiol, yielding 3-(((1-methyl-1H-tetrazol-5-yl)thio)methyl)-7-(2-sulfo-2-phenylacetamido)-3-cephem-4-carboxylic acid, sodium salt.

7-(2-(4-pyridylthio)acetamido)cephalosporanic acid is reacted with 1-methyl-1H-tetrazole-5-thiol, yielding 3-(((1-methyl-1H-tetrazol-5-yl)thio)methyl)-7-(2-(4-pyridylthio)acetamido)-3-cephem-4-carboxylic acid.

7-(5-Carbo-n-butoxy-5-(2,4-dichlorobenzamido)-valeramido)cephalosporanic acid and 5-methyl-1,3,4-thiadiazole-2-thiol are reacted, yielding 7-(((5-methyl-1,3,4-thiadiazol-2-yl)thio)methyl)-7-(5-carbo-n-butoxy-5-(2,4-dichlorobenzamido)valeramido)-3-cephem-4-carboxylic acid.

7-(5-Carbo-n-butoxy-5-(2,4-dichlorobenzamido)-valeramido)cephalosporanic acid and 1-methyl-1H-tetrazole-5-thiol are reacted yielding 3-(((1-methyl-1H-tetrazol-5-yl)thio)methyl)-7-(5-carbo-n-butoxy-5-(2,4-dichlorobenzamido)-3-cephem-4-carboxylic acid.

7-(2-(2-(p-nitrobenzyloxycarbonylamino)thiazol-4-yl)-2-methoxyimino)acetamido)cephalosporanic acid is reacted with 1-methyl-1H-tetrazole-5-thiol, yielding 3-(((1-methyl-1H-tetrazol-5-yl)thio)methyl)-7-(2-(2-(p-nitrobenzyloxycarbonylamino)thiazol-4-yl)-2-(methoxyimino)acetamido)-3-cephem-4-carboxylic acid.

7-(2-(2-(p-nitrobenzyloxycarbonylamino)thiazol-4-yl)acetamido)cephalosporanic acid is reacted with 1-methyl-1H-tetrazole-5-thiol yielding 3-(((1-methyl-1H-tetrazol-5-yl)thio)methyl)-7-(2-(2-(p-nitrobenzyloxycarbonylamino)thiazol-4-yl)acetamido)-3-cephem-4-carboxylic acid.

7-((2,2,2-Trichloroethoxy)carbonylamino)cephalosporanic acid is reacted with 6-hydroxypyridazine-3-thiol, yielding 3-(((6-hydroxypyridazin-3-yl)thio)methyl)-7-((2,2,2-trichloroethoxy)carbonylamino)-3-cephem-4-carboxylic acid.

7-(2-(2-Thienylacetamido)cephalosporanic acid is reacted with 6-hydroxypyridazine-3-thiol, yielding 3-(((6-hydroxypyridazin-3-yl)thio)methyl)-7-(2-(2-thienyl)acetamido)-3-cephem-4-carboxylic acid.

7-((2,2,2-Trichloroethoxy)carbonylamino)cephalosporanic acid is reacted with tetrazolo[1,5-b]pyridazine-6-thiol, yielding 3-(((tetrazolo[1,5-b]pyridazin-6-yl)thio)methyl)-7-((2,2,2-trichloroethoxy)carbonylamino)-3-cephem-4-carboxylic acid.

7-(2-(2-Thienyl)acetamido)cephalosporanic acid is reacted with tetrazolo[1,5-b]pyridazine-6-thiol, yielding 3-(((tetrazolo[1,5-b]pyridazin-6-yl)thio)methyl)-7-(2-(2-thienyl)acetamido-3-cephem-4-carboxylic acid.

7-((2,2,2-Trichloroethoxy)carbonylamino)cephalosporanic acid is reacted with 1-(sulfomethyl)-1H-tetrazole-5-thiol, sodium salt, yielding 3-(((1-(sulfomethyl)-1H-tetrazol-5-yl)thio)methyl)-7-((2,2,2-trichloroethoxy)carbonylamino)-3-cephem-4-carboxylic acid, sodium salt.

7-(2-(2-Thienyl)acetamido)cephalosporanic acid is reacted with 1-(sulfomethyl)-1H-tetrazole-5-thiol, sodium salt, yielding 3-(((1-(sulfomethyl)-1H-tetrazol-5-yl)thio)methyl)-7-(2-(2-thienyl)acetamido)-3-cephem-4-carboxylic acid, sodium salt.

7-((2,2,2-Trichloroethoxy)carbonylamino)cephalosporanic acid is reacted with 1-(2-(dimethylamino)ethyl)-1H-tetrazole-5-thiol, yielding 3-(((1-(2-(dimethylamino)ethyl)-1H-tetrazol-5-yl)thio)methyl)-7-((2,2,2-trichloroethoxy)carbonylamino)-3-cephem-4-carboxylic acid.

7-(2-(2-Thienyl)acetamido)cephalosporanic acid is reacted with 1-(2-(dimethylamino)ethyl)-1H-tetrazole-5-thiol, yielding 3-(((1-(2-(dimethylamino)ethyl)-1H-tetrazol-5-yl)thio)methyl)-7-(2-(2-thienyl)acetamido)-3-cephem-4-carboxylic acid.

7-(2-(2-Thienyl)acetamido)cephalosporanic acid is reacted with p-methoxybenzenethiol, yielding 3-(((p-methoxyphenyl)thio)methyl)-7-(2-(2-thienyl)acetamido)-3-cephem-4-carboxylic acid.

7-(2-(2-Thienyl)acetamido)cephalosporanic acid is reacted with p-chlorobenzenethiol, yielding 3-(((p-chlorophenyl)thio)methyl)-7-(2-(2-thienyl)acetamido)-3-cephem-4-carboxylic acid.

7-(2-(2-Thienyl)acetamido)cephalosporanic acid is reacted with o-toluenethiol, yielding 3-(((o-tolyl)thio)methyl)-7-(2-(2-thienyl)acetamido)-3-cephem-4-carboxylic acid.

7-(2-(1H-Tetrazol-1-yl)acetamido)cephalosporanic acid is reacted with 1,3,4-thiadiazole-2-thiol, yielding 3-(((1,3,4-thiadiazol-2-yl)thio)methyl)-7-(2-(1H-tetrazol-1-yl)acetamido)-3-cephem-4-carboxylic acid.

7-Phthalimidocephalosporanic acid is reacted with 5-methyl-1,3,4-thiadiazole-2-thiol, yielding 3-(((5-methyl-1,3,4-thiadiazol-2-yl)thio)methyl)-7-phthalimido-3-cephem-4-carboxylic acid.

7-(2-Hydroxy-2-phenylacetamido)cephalosporanic acid is reacted with 5-methyl-1,3,4-thiadiazole-2-thiol, yielding 3-(((5-methyl-1,3,4-thiadiazol-2-yl)thio)methyl)-7-(2-hydroxy-2-phenylacetamido)-3-cephem-4-carboxylic acid.

7-(2-Acetoxy-2-phenylacetamido)cephalosporanic acid is reacted with 5-methyl-1,3,4-thiadiazole-2-thiol, yielding 3-(((5-methyl-1,3,4-thiadiazol-2-yl)thio)methyl)-7-(2-acetoxy-2-phenylacetamido)-3-cephem-4-carboxylic acid.

7-(2-(Trifluoromethylthio)acetamido)cephalosporanic acid is reacted with 1-methyl-1H-tetrazole-5-thiol, yielding 3-(((1-methyl-1H-tetrazol-5-yl)thio)methyl)-7-(2-(trifluoromethylthio)acetamido)-3-cephem-4-carboxylic acid.

7-(2-(2-(p-nitrobenzyloxycarbonylamino)thiazol-4-yl)-2-(methoxyimino)acetamido)cephalosporanic acid is reacted with 4,5-dihydro-6-hydroxy-4-methyl-5-oxo-1,2,4-triazine-3-thiol, yielding 3-(((4,5-dihydro-6-hydroxy-4-methyl-5-oxo-1,2,4-triazin-3-yl)thio)methyl)-7-(2-(2-(p-nitrobenzyloxycarbonylamino)-3-cephem-4-carboxylic acid.

7-(2-(2-(p-nitrobenzyloxycarbonylamino)thiazol-4-yl)acetamido)cephalosporanic acid is reacted with 1-(2-(dimethylamino)ethyl)-1H-tetrazole-5-thiol, yielding 3-(((1-(2-(dimethylamino)ethyl)-1H-tetrazol-5-yl)thio)methyl)-7-(2-(2-(p-nitrobenzyloxycarbonylamino)thiazol-4-yl)acetamido)-3-cephem-4-carboxylic acid.

7-(2-(o-(tert-butoxycarbonylaminomethyl)phenyl)acetamido)cephalosporanic acid is reacted with tetrazolo[1,5-b]pyridazine-6-thiol, yielding 3-(((tetrazolo[1,5-b]pyridazin-6-yl)thio)methyl)-7-(2-(o-(tert-butoxycarbonylaminomethyl)phenyl)acetamido)-3-cephem-4-carboxylic acid.

7-(2-formyloxy-2-phenylacetamido)cephalosporanic acid is reacted with 1-(sulfomethyl)-1H-tetrazole-5-thiol, sodium salt, yielding 3-(((1-(sulfomethyl)-1H-tetrazol-5-yl)thio)methyl)-7-(2-formyloxy-2-phenylacetamido)-3-cephem-4-carboxylic acid.

I claim:

1. A method for the displacement of the 3-acyloxy of a 3-(acyloxymethyl)cephalosporin by a sulfur nucleophile, which comprises reacting, in an organic solvent and under essentially anhydrous conditions, a 3-(acyloxymethyl)cephalosporin compound of the formula

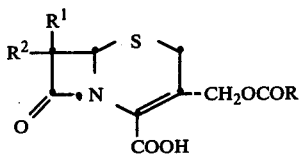

with a sulfur nucleophile of the formula:

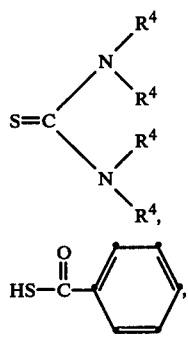 (1)

HS—C₁—C₄ alkyl, (3)

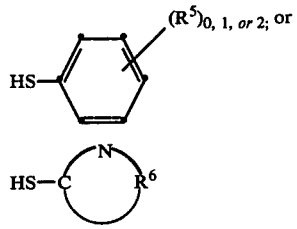 (4)

$HS-C\overset{N}{\underset{R^6}{\diagdown}}$ (5)

and obtaining a reaction product of the formula

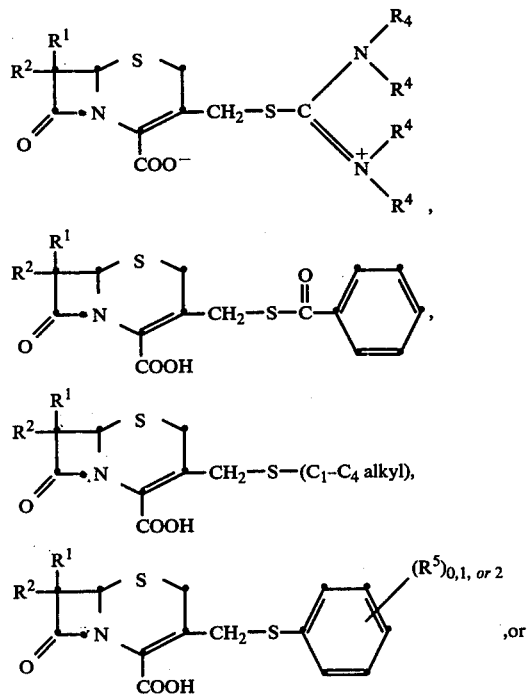

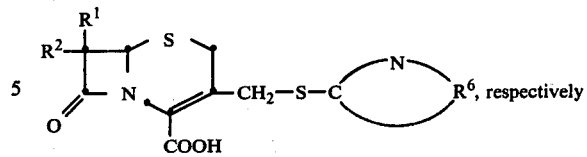, respectively

R is
(1) $C_1$-$C_3$ alkyl,
(2) $C_4$-$C_6$ cycloalkyl,
(3) amino,
(4) mono- or di($C_1$-$C_3$ alkyl)amino,

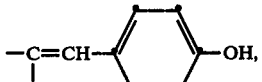 (5)

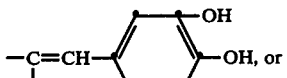 (6)

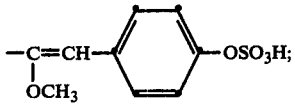 (7)

$R^1$ is hydrogen or methoxy;
$R^2$ is phthalimido, succinimido, a radical of the formula

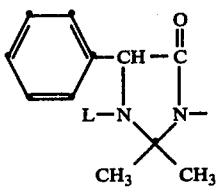

wherein L is hydrogen or nitroso, or a radical of the formula

$R^3$ is
(1) hydrogen,
(2) $C_1$-$C_6$ alkyl,
(3) —$CH_2$—($C_1$-$C_3$ chloroalkyl),
(4) —$CH_2$—($C_1$-$C_3$ fluoroalkyl),
(5) $C_1$-$C_4$ cyanoalkyl,
(6) $C_1$-$C_4$ hydroxyalkyl,
(7) p-nitrobenzyloxy,
(8) tert-butoxy,
(9) (2,2,2-trichloroethoxy),
(10) a protected 4-amino-4-carboxybutyl radical of the formula

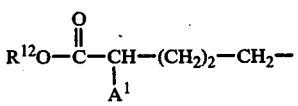

wherein $A^1$ is a protected amino group and $R^{12}$ is hydrogen or $C_1$-$C_4$ alkyl;
(11) 4-oxo-4-carboxybutyl;

(12) 3-carboxypropyl;
(13) a radical of the formula $$\underset{a^1}{\overset{a}{\text{[phenyl ring]}}}-(Z)_m-CH_2-$$

in which each of a and $a^1$ is independently hydrogen, $C_1$-$C_4$ alkyl, $C_1$-$C_4$ alkoxy, halogen, hydroxy, or $A^1CH_2$— wherein $A^1$ is, as above, protected amino; Z is O or S; and m is 0 or 1;

(14) a radical of the formula $$\text{P}-\underset{Q}{\overset{}{\text{CH}}}-$$

wherein P is
(a) 2-thienyl,
(b) 3-thienyl, or
(c) a phenyl group of the formula $$\underset{a^1}{\overset{a}{\text{[phenyl ring]}}}$$

in which a and $a^1$ are as defined above; and wherein Q is
(a) hydroxy,
(b) formyloxy,
(c) acetoxy,
(d) carboxy of the formula $$-\overset{O}{\underset{}{\text{C}}}-O-A^2$$

wherein $A^2$ is diphenylmethyl, p-nitrobenzyl, benzyl, 2,2,2-trichloroethyl, tert-butyl, or p-methoxybenzyl;
(e) (alkali metal oxysulfonyl),
(f) a protected amino group,
(g) an acylated amino group of the formula $$-NH-\overset{O}{\underset{}{\text{C}}}-T$$

wherein T represents amino, $$-NH-\overset{NH}{\underset{}{\text{C}}}-NH_2, \quad -\overset{R^7}{\underset{}{\text{N}}}-\overset{O}{\underset{}{\text{C}}}-R^8,$$

$$-\overset{R^7}{\underset{}{\text{N}}}-\overset{O}{\underset{}{\text{C}}}-CH=CHR^9, \quad \text{[piperazinedione ring with } R^{10}\text{]},$$

[ring with $R^{11}$, N, N–$R^{10}$, C=O], [phenyl]—$(OH)_{2 \text{ or } 3}$; or

[thiopyranone ring]

wherein $R^7$ is hydrogen or $C_1$-$C_3$ alkyl; $R^8$ is phenyl, halophenyl, furyl, monomethylamino, dimethylamino, monoethylamino, diethylamino, methylethylamino, propylamino, dipropylamino, diisopropylamino, phenylamino, or diphenylamino; $R^9$ is hydrogen, $C_1$-$C_4$ alkyl, or phenyl; $R^{10}$ is hydrogen, $C_1$-$C_3$ alkyl, or methylsulfonyl; and $R^{11}$ is ethylene, trimethylene, or vinylene;

(15) a radical of the formula $$P'-\overset{N-OH}{\underset{}{\text{C}}}-\overset{O}{\underset{}{\text{C}}}-, \quad -OCH_3, \quad -O\overset{O}{\underset{}{\text{C}}}CH_3$$

wherein P' is P as defined above, protected 2-amino-4-thiazolyl, or 2-furyl;

(16) a radical of the formula V-S(O)$_n$—CH$_2$— wherein V represents —CF$_3$ or —CH$_2$-X wherein X represents hydrogen, methyl, CF$_3$, CN, or N$_3$, and n represents 0, 1, or 2; or

(17) a radical of the formula Y—CH$_2$— in which Y is
(a) 2-thienyl,
(b) 3-thienyl,
(c) 2-furyl,
(d) 2-oxazolyl,
(e) 2-thiazolyl,
(f) 1-tetrazolyl,
(g) 1-benzotriazolyl,
(h) 2-oxazolylthio,
(i) 2-thiazolylthio,
(j) 1,2,3-triazol-5-ylthio,
(k) 1,3,4-triazol-2-ylthio,
(l) 1,3,4-thiadiazol-2-ylthio,
(m) protected 5-amino-1,3,4-thiadiazol-2-ylthio,
(n) 5-methyl-1,3,4-thiadiazol-2-ylthio,
(o) 1,2,4-thiadiazol-5-ylthio,
(p) 3-methyl-1,2,4-thiadiazol-5-ylthio,
(q) 1,2,5-thiadiazol-3-ylthio,
(r) 1,3,4-oxadiazol-2-ylthio,
(s) 5-methyl-1,3,4-oxadiazol-2-ylthio,
(t) 1-methyl-5-tetrazolylthio,
(u) pyridylthio,
(v) 4-cyano-1,2,3-triazol-1-yl,
(w) 3-cyano-1,2,4-triazol-1-yl, or
(x) protected 2-amino-4-thiazolyl;

each $R^4$ is independently
(1) hydrogen,
(2) $C_1$-$C_4$ alkyl,
(3) $C_2$-$C_3$ alkenyl,
(4) cyclohexyl, or
(5) phenyl;

each $R^5$ is independently $C_1$-$C_4$ alkyl, $C_1$-$C_4$ alkoxy, halo, hydroxy, nitro, cyano, methanesulfonamido, or trifluoromethyl; and $R^6$ is (1) a unit which with the

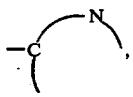

comprises an unsubstituted or substituted, five or six-membered, heteroaromatic ring having a total of from 1 to 4 hetero atoms selected from the following combinations:
1 nitrogen and 0 or 1 oxygen or sulfur,
2 nitrogens and 0 or 1 oxygen or sulfur,
3 nitrogens, and 0 or 1 oxygen, or
4 nitrogens,
all other ring atoms being carbon; or (2) a unit which with the

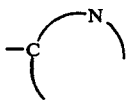

comprises 2-benzimidazolyl, 2-benzothiazolyl, 2-benzoxazolyl, or a radical of the formula

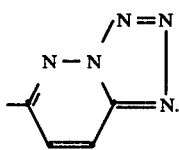

2. The method of claim 1 wherein the 3-(acyloxymethyl)cephalosporin is a 3-(acetoxymethyl)cephalosporin.

3. The method of claim 2 wherein the 3-(acetoxymethyl)cephalosporin is 7-(2-(2-thienyl)acetamido)cephalosporanic acid.

4. The method of claim 3 wherein the sulfur nucleophile is thiourea.

5. The method of claim 3 wherein the sulfur nucleophile is a heteroarylthiol of the formula

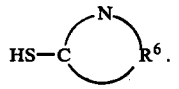

6. The method of claim 5 wherein the heteroarylthiol is 1-methyl-1H-tetrazole-5-thiol.

7. The method of claim 5 wherein the heteroarylthiol is 4,5-dihydro-6-hydroxy-4-methyl-5-oxo-1,2,4-triazine-3-thiol.

8. The method of claim 5 wherein the heteroarylthio is 5-methyl-1,3,4-oxadiazole-2-thiol.

9. The method of claim 5 wherein the heteroarylthio is 5-methyl-1,3,4-thiadiazole-2-thiol.

10. The method of claim 5 wherein the heteroarylthiol is 2-mercaptobenzothiazole.

11. The method of claim 5 wherein the heteroarylthio is 5-(N-methylacetamido)-1,3,4-thiadiazole-2-thiol.

12. The method of claim 5 wherein the heteroarylthiol is 3-methyl-1,2,4-oxadiazole-5-thiol.

13. The method of claim 5 wherein the heteroarylthiol is 3-methyl-1,2,4-thiadiazole-5-thiol.

14. The method of claim 5 wherein the heteroarylthiol is 2-mercaptopyrimidine.

15. The method of claim 5 wherein the heteroarylthiol is 2-oxazolethiol.

16. The method of claim 5 wherein the heteroarylthiol is 4-phenyl-2-thiazolethiol.

17. The method of claim 5 wherein the heteroarylthiol is a protected 3-(aminomethyl)-1,2,4-triazole-5-thiol.

18. The method of claim 5 wherein the heteroarylthiol is 1-(carboxymethyl)-1H-tetrazole-5-thiol.

19. The method of claim 2 wherein the 3-(acetoxymethyl)cephalosporin is 7-(2-(1H-tetrazol-1-yl)acetamido)cephalosporanic acid.

20. The method of claim 19 wherein the sulfur nucleophile is 5-methyl-1,3,4-thiadiazole-2-thiol.

21. The method of claim 20 wherein the organic solvent is nitromethane.

22. The method of claim 20 wherein the organic solvent is propionitrile.

23. The method of claim 20 wherein the organic solvent is acetonitrile.

24. The method of claim 20 wherein the organic solvent is acetic acid.

25. The method of claim 19 wherein the sulfur nucleophile is 1,3,4-thiadiazole-2-thiol.

26. The method of claim 19 wherein the sulfur nucleophile is 1-methyl-1H-tetrazole-5-thiol.

27. The method of claim 19 wherein the sulfur nucleophile is 2-oxazolethiol.

28. The method of claim 19 wherein the sulfur nucleophile is 1,3,4-triazole-5-thiol.

29. The method of claim 2 wherein the 3-(acetoxymethyl)cephalosporin is 7-(2-hydroxy-2-phenylacetamido)cephalosporanic acid.

30. The method of claim 29 wherein the sulfur nucleophile is 1-methyl-1H-tetrazole-5-thiol.

31. The method of claim 29 wherein the sulfur nucleophile is 1-(alkali metaloxysulfonylmethyl)-1H-tetrazole-5-thiol.

32. The method of claim 2 wherein the 3-(acetoxymethyl)cephalosporin is 7-(2-formyloxy-2-phenylacetamido)cephalosporanic acid.

33. The method of claim 32 wherein the sulfur nucleophile is 1-methyl-1H-tetrazole-5-thiol.

34. The method of claim 33 wherein the organic solvent is 1,2-dichloroethane.

35. The method of claim 33 wherein the organic solvent is acetonitrile.

36. The method of claim 32 wherein the sulfur nucleophile is 2-oxazolethiol.

37. The method of claim 32 wherein the sulfur nucleophile is 1-(carboxymethyl)-1H-tetrazole-5-thiol.

38. The method of claim 32 wherein the sulfur nucleophile is 1-(alkali metal oxysulfonylmethyl)-1H-tetrazole-5-thiol.

39. The method of claim 2 wherein the 3-(acetoxymethyl)cephalosporin is 7-formamidocephalosporanic acid.

40. The method of claim 2 wherein the 3-(acetoxymethyl)cephalosporanic acid is 7-acetamidocephalosporanic acid.

41. The method of claim 2 wherein the 3-(acetoxymethyl)cephalosporanic acid is 7-(2-phenylacetamido)cephalosporanic acid.

42. The method of claim 41 wherein the sulfur nucleophile is 5-methyl-1,3,4-thiadiazole-2-thiol.

43. The method of claim 2 wherein the 3-(acetoxymethyl)cephalosporin is 7-methoxy-7-(2-phenylacetamido)cephalosporanic acid.

44. The method of claim 2 wherein the 3-(acetoxymethyl)cephalosporin is 7-(2-phenoxyacetamido)cephalosporanic acid.

45. The method of claim 2 wherein the 3-(acetoxymethyl)cephalosporin is 7-(2-(trifluoromethylthio)acetamido)cephalosporanic acid.

46. The method of claim 45 wherein the sulfur nucleophile is 1-methyl-1H-tetrazole-5-thiol.

47. The method of claim 2 wherein the 3-(acetoxymethyl)cephalosporin is 7-(2-(cyanomethylthio)acetamido)cephalosporanic acid.

48. The method of claim 47 wherein the sulfur nucleophile is 1-methyl-1H-tetrazole-5-thiol.

49. The method of claim 2 wherein the 3-(acetoxymethyl)cephalosporin is 7-methoxy-7-(2-(cyanomethylthio)acetamido)cephalosporanic acid.

50. The method of claim 49 wherein the sulfur nucleophile is 1-methyl-1H-tetrazole-5-thiol.

51. The method of claim 2 wherein the 3-(acetoxymethyl)cephalosporin is a protected 7-(2-(o-(aminomethyl)phenyl)acetamido)cephalosporanic acid.

52. The method of claim 51 wherein the sulfur nucleophile is 1-(carboxymethyl)-1H-tetrazole-5-thiol.

53. The method of claim 51 wherein the sulfur nucleophile is tetrazolo[1,5-b]pyridazin-6-thiol.

54. The method of claim 2 wherein the 3-(acetoxymethyl)cephalosporin is a protected 7-(2-amino-2-phenylacetamido)cephalosporanic acid.

55. The method of claim 54 wherein the sulfur nucleophile is 1-methyl-1H-tetrazole-5-thiol.

56. The method of claim 2 wherein the 3-(acetoxymethyl)cephalosporin is a protected 7-(2-amino-2-(p-hydroxyphenyl)acetamido)cephalosporanic acid.

57. The method of claim 56 wherein the sulfur nucleophile is 1-methyl-1H-tetrazole-5-thiol.

58. The method of claim 2 wherein the 3-(acetoxymethyl)cephalosporin is a

7-(2-(C—O—A$^2$)-2-phenylacetamido)cephalosporanic acid.

59. The method of claim 58 wherein the sulfur nucleophile is 1-methyl-1H-tetrazole-5-thiol.

60. The method of claim 2 wherein the 3-(acetoxymethyl)cephalosporin is 7-(2-ureido-2-thienylacetamido)cephalosporanic acid.

61. The method of claim 60 wherein the sulfur nucleophile is 1-methyl-1H-tetrazole-5-thiol.

62. The method of claim 2 wherein the 3-(acetoxymethyl)cephalosporin is 7-(N-((1,3-dimethylureido)carbonyl)-2-phenylglycylamido)cephalosporanic acid.

63. The method of claim 62 wherein the sulfur nucleophile is 1-methyl-1H-tetrazole-5-thiol.

64. The method of claim 2 wherein the 3-(acetoxymethyl)cephalosporin is a protected 7-(2-(2-amino-4-thiazolyl)acetamido)cephalosporanic acid.

65. The method of claim 64 wherein the sulfur nucleophile is 1-(2-dimethylamino)ethyl)-1H-tetrazole-5-thiol.

66. The method of claim 2 wherein the 3-(acetoxymethyl)cephalosporin is a protected 7-(2-(methoxyimino)-2-(2-amino-4-thiazolyl)acetamido)cephalosporanic acid.

67. The method of claim 66 wherein the sulfur nucleophile is 4,5-dihydro-6-hydroxy-4-methyl-5-oxo-1,2,4-triazine-3-thiol.

68. The method of claim 2 wherein the 3-(acetoxymethyl)cephalosporin is a protected 7-(5-amino-5-COOR$^{12}$-valeramido)cephalosporanic acid.

69. The method of claim 68 wherein the sulfur nucleophile is 1-methyl-1H-tetrazole-5-thiol.

70. The method of claim 68 wherein the sulfur nucleophile is 5-methyl-1,3,4-thiadiazole-2-thiol.

71. The method of claim 68 wherein the sulfur nucleophile is 4,5-dihydro-6-hydroxy-4-methyl-5-oxo-1,2,4-triazine-3-thiol.

72. The method of claim 68 wherein the sulfur nucleophile is 1-methyl-1H-1,2,3-triazole-5-thiol.

73. The method of claim 68 wherein the sulfur nucleophile is 1-(carboxymethyl)-1H-tetrazole-5-thiol.

74. The method of claim 68 wherein the sulfur nucleophile is 5-methyl-1,3,4-oxadiazole-2-thiol.

75. The method of claim 68 wherein the sulfur nucleophile is 1-benzyl-1H-tetrazole-5-thiol.

76. The method of claim 68 wherein the sulfur nucleophile is thiourea.

77. The method of claim 2 wherein the 3-(acetoxymethyl)cephalosporin is a protected 7-methoxy-7-(5-amino-5-COOR$^{12}$-valeramido)cephalosporanic acid.

78. The method of claim 77 wherein the sulfur nucleophile is 1-methyl-1H-tetrazole-5-thiol.

79. The method of claim 77 wherein the sulfur nucleophile is 5-methyl-1,3,4-thiadiazole-2-thiol.

80. The method of claim 77 wherein the sulfur nucleophile is 4,5-dihydro-6-hydroxy-4-methyl-5-oxo-1,2,4-triazine-3-thiol.

81. The method of claim 77 wherein the sulfur nucleophile is thiourea.

82. The method of claim 2 wherein the 3-(acetoxymethyl)cephalosporin is 7-(2-((4-ethyl-2,3-dioxo-1-piperazinyl)carbonylamino)-2-(p-hydroxyphenyl)acetamido)cephalosporanic acid.

83. The method of claim 82 wherein the sulfur nucleophile is 1-methyl-1H-tetrazole-5-thiol.

84. The method of claim 2 wherein the 3-(acetoxymethyl)cephalosporin is 7-methoxy-7-(2-(1H-tetrazol-1-yl)acetamido)cephalosporanic acid.

85. The method of claim 84 wherein the sulfur nucleophile is 1-methyl-1H-tetrazole-5-thiol.

86. The method of claim 1 wherein the 3-(acyloxymethyl)cephalosporin is a 3-(carbamoyloxymethyl)-3-cephem-4-carboxylic acid.

87. The method of claim 86 wherein the 3(carbamoyloxymethyl)-3-cephem-4-carboxylic acid is a protected 7-(5-amino-5-COOR$^{12}$-valeramido)-3-(carbamoyloxymethyl)-3-cephem-4-carboxylic acid.

88. The method of claim 87 wherein the sulfur nucleophile is thiourea.

89. The method of claim 87 wherein the sulfur nucleophile is 1-methyl-1H-tetrazole-5-thiol.

90. The method of claim 87 wherein the sulfur nucleophile is 5-methyl-1,3,4-thiadiazole-2-thiol.

91. The method of claim 87 wherein the sulfur nucleophile is 1-(carboxymethyl)-1H-tetrazole-5-thiol.

92. The method of claim 86 wherein the 3-(carbamoyloxymethyl)-3-cephem-4-carboxylic acid is a protected 7-methoxy-7-(5-amino-5-COOR$^{12}$-valeramido)-3-(carbamoyloxymethyl)-3-cephem-4-carboxylic acid.

93. The method of claim 1 wherein the sulfur nucleophile is of the formula

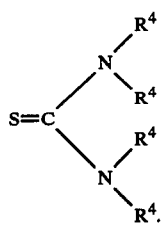

94. The method of claim 93 wherein the sulfur nucleophile is thiourea.

95. The method of claim 1 wherein the sulfur nucleophile is a heteroarylthiol of the formula

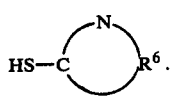

96. The method of claim 95 wherein the heteroarylthiol is a 1H-tetrazole-5-thiol.

97. The method of claim 96 wherein the heteroarylthiol is 1-methyl-1H-tetrazole-5-thiol.

98. The method of claim 96 wherein the heteroarylthiol is 1-(carboxymethyl)-1H-tetrazole-5-thiol.

99. The method of claim 95 wherein the heteroarylthiol is a 1,3,4-thiadiazole-5-thiol.

100. The method of claim 99 wherein the heteroarylthiol is 5-methyl-1,3,4-thiadiazole-2-thiol.

101. The method of claim 95 wherein the heteroarylthiol is a triazole.

102. The method of claim 95 wherein the heteroarylthiol is 4,5-dihydro-6-hydroxy-4-methyl-5-oxo-1,2,4-triazine-3-thiol.

103. The method of claim 95 wherein the heteroarylthiol is

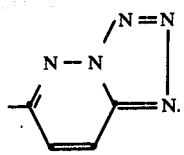

104. The method of claim 1 wherein the organic solvent is a hydrocarbon, halogenated hydrocarbon, ketone, carboxylic acid, carboxylic acid ester, nitro compound, nitrile, or thioether, and the reaction is carried out at temperatures from about 70° to 120° C.

105. The method of claim 104 wherein the 3-(acyloxymethyl)cephalosporin is 7-(2-(1H-tetrazol-1-yl)acetamido)cephalosporanic acid.

106. The method of claim 104 wherein the 3-(acyloxymethyl)cephalosporin is 7-(2-formyloxy-2-phenylacetamido)cephalosporanic acid.

107. The method of claim 104 wherein the 3-(acyloxymethyl)cephalosporin is a protected 7-(2-amino-2-(p-hydroxyphenyl)acetamido)cephalosporanic acid.

108. The method of claim 104 wherein the 3-(acyloxymethyl)cephalosporin is a protected 7-(2-amino-2-phenylacetamido)cephalosporanic acid.

109. The method of claim 104 wherein the 3-(acyloxymethyl)cephalosporin is a protected 7-(2-(o-(aminomethyl)phenyl)acetamido)cephalosporanic acid.

110. The method of claim 104 wherein the 3-(acyloxymethyl)cephalosporin is 7-(2-trifluoromethylthio)acetamido)cephalosporanic acid.

111. The method of claim 104 wherein the 3-(acyloxymethyl)cephalosporin is 7-methoxy-7-(2-cyanomethylthio)acetamido)cephalosporanic acid.

112. The method of claim 104 wherein the sulfur nucleophile is 1-methyl-1H-tetrazole-5-thiol.

113. The method of claim 112 wherein the 3-(acyloxymethyl)cephalosporin is 7-(2-formyloxy-2-phenylacetamido)cephalosporanic acid.

114. The method of claim 104 wherein the sulfur nucleophile is 5-methyl-1,3,4-thiadiazole-2-thiol.

115. The method of claim 104 wherein the 3-(acyloxymethyl)cephalosporin is 7-(2-1H-tetrazol-1-yl)acetamido)cephalosporanic acid.

* * * * *